United States Patent
Malafa et al.

(10) Patent No.: US 12,129,522 B2
(45) Date of Patent: *Oct. 29, 2024

(54) MICRORNA ASSAY FOR DETECTION AND MANAGEMENT OF PANCREATIC CANCER PRECURSORS

(71) Applicant: H. Lee Moffitt Cancer Center and Research Institute, Inc., Tampa, FL (US)

(72) Inventors: Mokenge P. Malafa, Tampa, FL (US); Jennifer Permuth, Tampa, FL (US); Dung-Tsa Chen, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/816,087

(22) Filed: Jul. 29, 2022

(65) Prior Publication Data
US 2023/0046649 A1 Feb. 16, 2023

Related U.S. Application Data

(63) Continuation of application No. 17/554,476, filed on Dec. 17, 2021, which is a continuation of application (Continued)

(51) Int. Cl.
*C12Q 1/6886* (2018.01)
(52) U.S. Cl.
CPC ...... *C12Q 1/6886* (2013.01); *C12Q 2600/118* (2013.01); *C12Q 2600/158* (2013.01); *C12Q 2600/178* (2013.01)
(58) Field of Classification Search
CPC ............ C12Q 1/6886; C12Q 2600/18; C12Q 2600/158; C12Q 2600/178
See application file for complete search history.

(56) References Cited

U.S. PATENT DOCUMENTS

| 7,919,237 B2 | 4/2011 | Dimitrov et al. |
| 8,415,102 B2 | 4/2013 | Geiss et al. |
| | (Continued) | |

OTHER PUBLICATIONS

Harvey V. Fineberg (JAMA, 2013 vol. 310:85-90).*
(Continued)

*Primary Examiner* — Terra C Gibbs
(74) *Attorney, Agent, or Firm* — Meunier Carlin & Curfman LLC

(57) ABSTRACT

The current invention pertains to miRNAs that are differentially expressed in samples of an individual having pancreatic cancer, or having a high risk of developing pancreatic cancer, as compared to the corresponding sample of an individual not having pancreatic cancer, or having low risk of developing pancreatic cancer, respectively. In certain embodiments, the miRNAs are differentially expressed in a tissue sample or blood plasma sample of an individual having a pancreatic lesion and having a high risk of developing pancreatic cancer as compared to the corresponding tissue sample or blood sample of an individual having the pancreatic lesion and having no risk or low risk of developing pancreatic cancer. These differentially expressed miRNAs can be used as biomarkers for diagnosis, treatment, and/or prevention of pancreatic cancer, particularly, in a subject having a pancreatic lesion. Microarray containing miRNAs indicative of the presence of pancreatic cancer, or having a high risk of pancreatic cancer development, particularly, in a subject having a pancreatic lesion, and methods of use of the microarrays are also provided.

4 Claims, 26 Drawing Sheets

Specification includes a Sequence Listing.

Related U.S. Application Data

No. 17/233,855, filed on Apr. 19, 2021, now abandoned, which is a continuation of application No. 16/362,623, filed on Mar. 23, 2019, now abandoned, which is a continuation of application No. 15/300,808, filed as application No. PCT/US2015/023702 on Mar. 31, 2015, now Pat. No. 10,240,208.

(60) Provisional application No. 61/973,068, filed on Mar. 31, 2014.

(56) References Cited

U.S. PATENT DOCUMENTS

| 8,519,115 B2 | 8/2013 | Webster et al. | |
|---|---|---|---|
| 10,240,208 B2* | 3/2019 | Malafa | C12Q 1/6886 |
| 2013/0324589 A1 | 12/2013 | Croce et al. | |

OTHER PUBLICATIONS

The American Cancer Society. Pancreatic Cancer Causes, Risk Factors, and Prevention. Downloaded from https://www.cancer.org/content/dam/CRC/PDF/Public/8779.00.pdf on Sep. 11, 2023.*
Lubezky et al. (Surgery, vol. 153:663-672 Epub Jan. 7, 2013).*
Gagner and Palermo (J. Hepatobiliary Pancreatic Surgery, 2009 vol. 16:726-730).*
Bauer et al. (PLOS One, 2012 vol. 7: Issue 4, e34151, plus Supplementary Information).*
Abdalla, M. et al., "Effect of RNA Isolation Method on microRNA Quantity and Quality in Plasma: A Comparative Study," Norgen Biotek Corporation Application Note 49: RNA Sample Preparation, 2011, pp. 1-4.
Bergmann, U. et al., "Increased expression of insulin receptor substrate-1 in human pancreatic cancer," Biochem. Biophys. Res. Commun., 1996, vol. 220, No. 3, pp. 886-890, abstract.
Blondal, T. et al., "Assessing sample and miRNA profile quality in serum and plasma or other biofluids," Methods, 2013, vol. 59, No. 1, pp. S1-S6.
Canto, M.I. et al., "International Cancer of the Pancreas Screening (CAPS) Consortium summit on the management of patients with increased risk for familial pancreatic cancer," Gut, 2013, vol. 62, No. 3, oo. 339-347.
Chen, D.T. et al., "Prognostic and predictive value of a malignancy-risk gene signature in early-stage non-small cell lung cancer," J. Natl. Cancer Inst., 2011, vol. 103, No. 24, pp. 1859-1870.
Chen, D.T. et al., "Proliferative genes dominate malignancy-risk gene signature in histologically-normal breast tissue," Breast Cancer Res. Treat., 2010, vol. 119, No. 2, pp. 335-346.
Chiyomaru, T. et al., "Genistein up-regulates tumor suppressor microRNA-574-3p in prostate cancer," PLOS ONE, 2013, vol. 8, No. 3, e58929.
Farina, N.H. et al., "Standardizing analysis of circulating microRNA: clinical and biological relevance," J. Cell. Biochem., 2014, vol. 115, No. 5, pp. 805-811.
Fineberg, H. "The paradox of disease prevention celebrated in principle, resisted in practice" JAMA, 2013, vol. 310, No. 1, pp. 85-90.
Fourie, N.H. et al., "Elevated circulating miR-150 and miR-342-3p in patients with irritable bowel syndrome," Exp. Mo/. Pathol., 2014, vol. 96, No. 3, pp. 422-425.
Frampton, A.E. et al., "Loss of miR-126 is crucial to pancreatic cancer progression," Expert Rev. Anticancer Ther., 2012, vol. 12, No. 7, pp. 881-884, abstract.
Gagner, M. and Palermo, M. "Laparoscopic Whipple procedure: review of the literature" J. Hepatobiliary Pancreatic Surgery, 2009, vol. 16, pp. 726-730.
Ganepola, G.A. et al., "Novel blood-based microRNA biomarker panel for early diagnosis of pancreatic cancer," World J. Gastrointestinal Onco., 2014, vol. 6, pp. 22-33.
Gao, L. et al., "miR-335 functions as a tumor suppressor in pancreatic cancer by targeting OCT4," Tumour Biology, 2014, vol. 35, No. 8, pp. 8309-8318, abstract.
Geiss, G.K. et al., "Direct multiplexed measurement of gene expression with color-coded probe pairs," Nat. Biotechnol., 2008, vol. 26, No. 3, pp. 317-325, abstract.
Greenbaum, D. et al., "Comparing protein abundance and mRNA expression levels on a genomic scale," Genome Biol., 2003, vol. 4, No. 9, p. 117.
Henry, J.C. et al., "MicroRNA from Pancreatic Duct Aspirate Differentiates Cystic Lesions of the Pancreas," Ann. Surg. Oneal., 2013, vol. 20, No. Suppl. 3, pp. S661-S666, abstract.
Hirata, H. et al., "Genistein downregulates onco-miR-1260b and upregulates SFRP1 and Smad4 via demethylation and histone modification in prostate cancer cells," Br. J. Cancer, 2014, vol. 110, No. 6, pp. 1645-1654.
Hruban, R.H. et al., "Precursors to pancreatic cancer," Gastroenterol. Clin. North. Am., 2007, vol. 36, No. 4, pp. 831-849.
Hu, J. et al., "Human miR-1228 as a stable endogenous control for the quantification of circulating microRNAs in cancer patients," Int. J. Cancer, 2014, vol. 135, No. 5, pp. 1187-1194.
Jiao, L.R. et al., "MicroRNAs targeting oncogenes are downregulated in pancreatic malignant transformation from benign tumors," PLOS ONE, 2012, vol. 7, No. 2, e32068.
Kapoor, S., "miR-145 and its influence on tumor growth in systemic malignancies," Eur. J. Cancer Prev., 2014, vol. 23, No. 3, p. 233, abstract.
Kirschner, M.B. et al., "The Impact of Hemolysis on Cell-Free microRNA Biomarkers," Front Genet., 2013, vol. 4, Article 94, pp. 1-13.
Lee, L.S. et al. "Investigating microRNA expression profiles in pancreatic cystic neoplasms," Clinical and Translational Gastroenterology, 2014, vol. 5, e47, pp. 1-6.
Li, A. et al., "Pancreatic cancers epigenetically silence SIP1 and hypomethylate and overexpress miR-200a/200b in association with elevated circulating miR-200a and miR-200b levels," Cancer Res., 2010, vol. 70, No. 13, pp. 5226-5237.
Li, A. et al., "MicroRNA Array Analysis Finds Elevated Serum miR-1290 Accurately Distinguishes Patients with Low-Stage Pancreatic Cancer from Healthy and Disease Controls," Clin. Cancer Res., 2013, vol. 19, No. 13, pp. 3600-3610.
Li, B.H. et al., "Reduced miR-100 expression in cervical cancer and precursors and its carcinogenic effect through targeting PLK1 protein," Eur. J. Cancer, 2011, vol. 47, No. 14, pp. 2166-2174, abstract.
Liu, J. et al., "MicroRNA-100 is a potential molecular marker of non-small cell lung cancer and functions as a tumor suppressor by targeting polo-like kinase 1," BMC Cancer, 2012, vol. 12, p. 519.
Liu, R. et al., "Serum microRNA expression profile as a biomarker in the diagnosis and prognosis of pancreatic cancer," Clin. Chem., 2012, vol. 58, No. 3, pp. 610-618.
Lubezky, N. et al., "MicroRNA expression signatures in intraductal papillary mucinous neoplasm of the pancreas," Surgery, 2013, vol. 153, pp. 663-672.
Matthaei, H. et al., "miRNA biomarkers in cyst fluid augment the diagnosis and management of pancreatic cysts," Clin. Cancer Res., 2012, vol. 18, No. 17, pp. 4713-4724.
Mitchell, P.S. et al., "Circulating microRNAs as stable blood-based markers for cancer detection," Proc. Natl. Acad. Sci. USA, 2008, vol. 105, No. 30, pp. 10513-10518.
Nissim, S. et al., "Genetic markers of malignant transformation in intraductal papillary mucinous neoplasm of the pancreas: a meta-analysis," Pancreas, 2012, vol. 41, No. 8, pp. 1195-1205.
Permuth-Wey, J. et al., "A genome-wide investigation of microRNA expression identifies biologically-meaningful microRNAs that distinguish between high-risk and low-risk intraductal papillary mucinous neoplasms of the pancreas," PIOS ONE, 2015, vol. 10,No. 1, e0116869.
Permuth-Wey, J. et al., "Tackling a clinical challenge: Using microRNAs to differentiate between low-and high-risk Pancreatic Cysts," Cancer Res, 2013, vol. 73, No. 8 Suppl., Abstract No. LB-70.
Permuth-Wey, J. et al., "Tackling a clinical challenge: Using microRNAs to differentiate between low-and high-risk Pancreatic Cysts," poster

(56) References Cited

OTHER PUBLICATIONS presented at Proceedings of the 104th Annual Meeting of the American Association for Cancer Research, Apr. 6-10, 2013, Washington, D.C.
Pritchard, C.C. et al., "Blood cell origin of circulating microRNAs: a cautionary note for cancer biomarker studies," Cancer Prev. Res. (Phi/a.), 2012, vol. 5, No. 3, pp. 492-497.
Sachs, T. et al., "The incidental asymptomatic pancreatic lesion: nuisance or threat?" J. Gastrointest. Surg., 2009, vol. 13, No. 3, pp. 405-415, abstract.
Schultz, N.A. et al., "MicroRNA biomarkers in whole blood for detection of pancreatic cancer," JAMA, 2014, vol. 311, No. 4, pp. 392-404, abstract.
Su, Y. et al., "Aberrant expression of microRNAs in gastric cancer and biological significance of miR-574-3p," International Immunopharmaco/ogy, 2012, vol. 13, No. 4, pp. 468-475.
Sun, D. et al., "miR-99 family of MicroRNAs suppresses the expression of prostate-specific antigen and prostate cancer cell proliferation," Cancer Res., 2011, vol. 71, No. 4,00. 1313-1324.
Suryawanshi, S. et al., "Plasma microRNAs as novel biomarkers for endometriosis and endometriosis-associated ovarian cancer," Clin. Cancer Res., 2013, vol. 19, No. 5, pp. 1213-1224.
Tanaka, M. et al., "International consensus guidelines 2012 for the management of IPMN and MCN of the pancreas," Pancreatology, 2012, vol. 12, No. 3, pp. 183-197.
Tang, S. et al., "Sweating the small stuff: microRNAs and genetic changes define pancreatic cancer," Pancreas, 2013, vol. 42, No. 5, pp. 740-759.
The American Cancer Society, "Can Pancreatic Cancer Be Prevented?" Last Revised: Jun. 9, 2020, accessible at https://www.cancer.org/cancer/types/pancreatic-cancer/causes-risks-prevention/prevention.html.
Wang, H. et al., "MicroRNA-342 inhibits colorectal cancer cell proliferation and invasion by directly targeting DNA methyltransferase 1," Carcinogenesis, 2011, vol. 32, No. 7, pp. 1033-1042.
Wang, J. et al., "MicroRNAs in plasma of pancreatic ductal adenocarcinoma patients as novel blood-based biomarkers of disease," Cancer Prev. Res. (Phi/a.), 2009, vol. 2, No. 9,00. 807-813.
Weichert, W. et al., "Overexpression of Polo-like kinase 1 is a common and early event in pancreatic cancer," Pancreatology, 2005, vol. 5, Nos. 2-3, pp. 259-265, abstract.
Wu, J. et al., "Recurrent GNAS mutations define an unexpected pathway for pancreatic cyst development," Sci. Transl. Med., 2011, vol. 3, No. 92, 92ra66.
Yachida, S. et al., "Distant metastasis occurs late during the genetic evolution of pancreatic cancer," Nature, 2010, vol. 467, No. 7319, pp. 1114-1117.
Zhang, D.X. et al., "Prognostic factors in patients with pancreatic cancer," Exp. Ther. Med., 2012, vol. 3, No. 3, pp. 423-432.
Zhang, J.J. et al., "Association of increased DNA methyltransferase expression with carcinogenesis and poor prognosis in pancreatic ductal adenocarcinoma," Clin. Transl. Oneal., 2012, vol. 14, No. 2, pp. 116-124.
Metcalf, "MicroRNAs: circulating biomarkers for the early detection of imperceptible cancers via biosensor and machine-learning advances," Oncogene, doi: 10.1038/s441388-024-030763, pp. 1-8 (2024).

* cited by examiner

* 8 of these IPMNs had tissue evaluated in the discovery or validation phase.

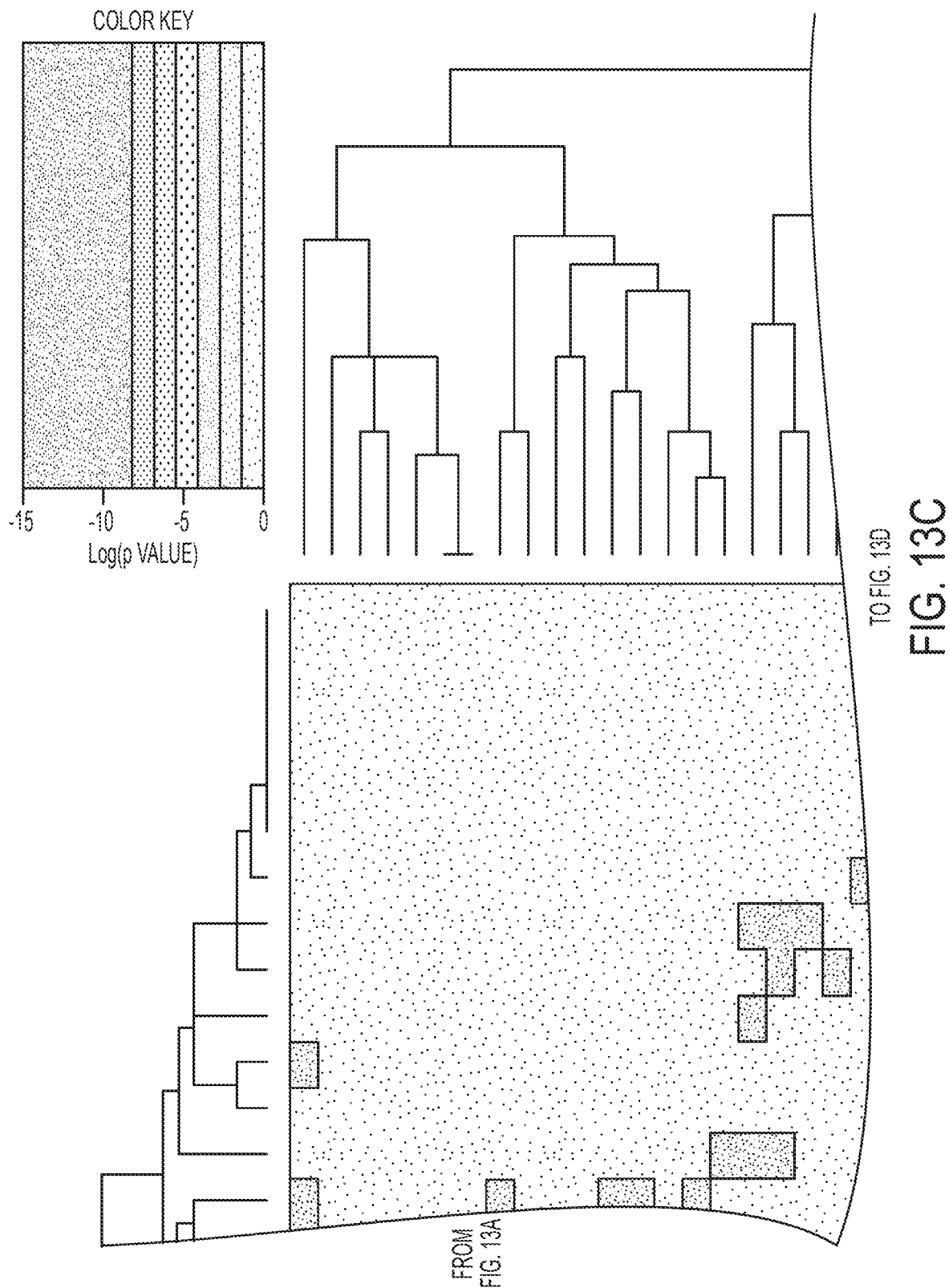

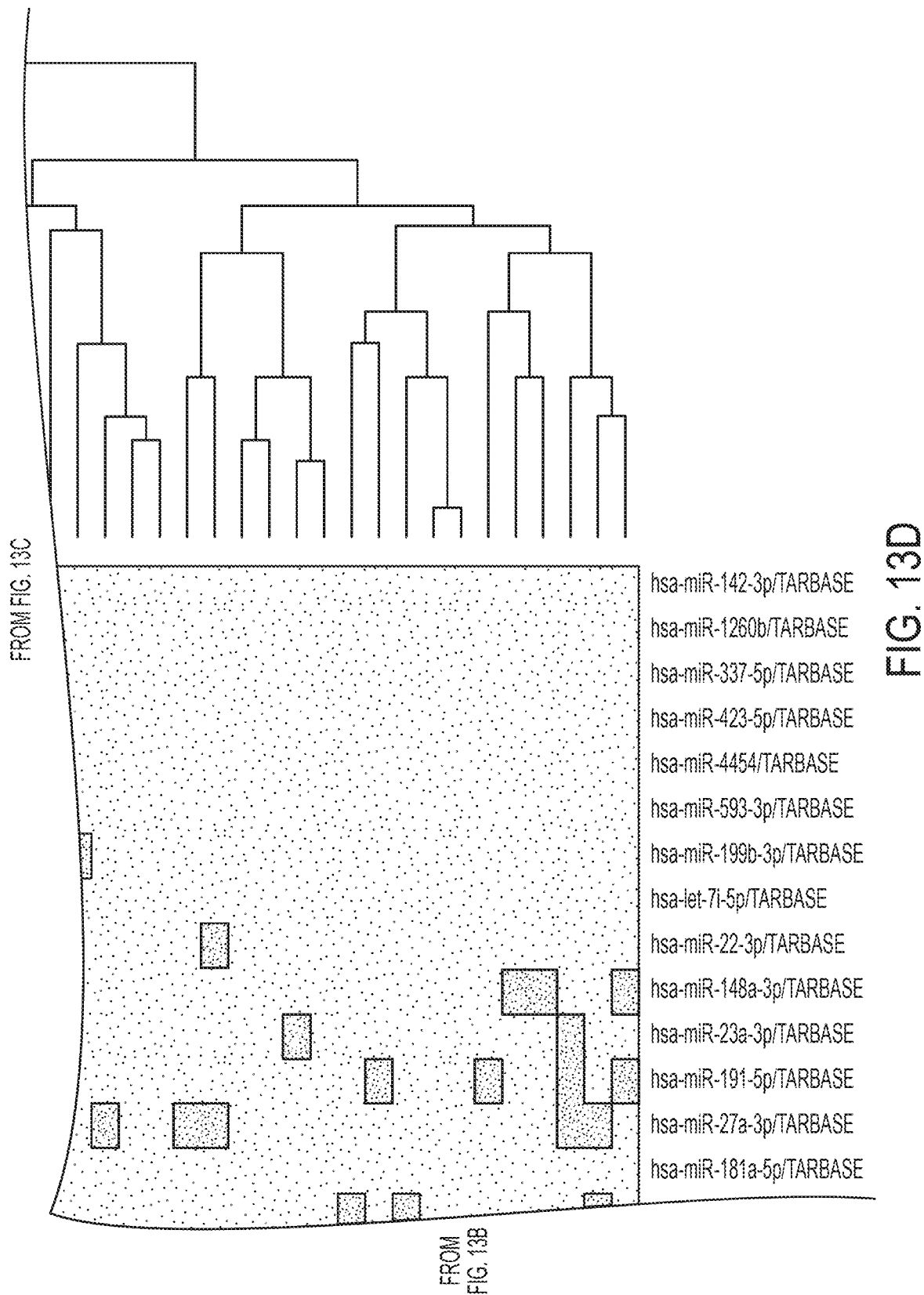

SEQUENCE LISTING

```
Sequence total quantity: 78
SEQ ID NO: 1           moltype = RNA  length = 80
FEATURE                Location/Qualifiers
source                 1..80
                       mol_type = other RNA
                       organism = Homo sapiens
SEQUENCE: 1
cctgttgcca caaacccgta gatccgaact tgtggtatta gtccgcacaa gcttgtatct   60
ataggtatgt gtctgttagg                                               80

SEQ ID NO: 2           moltype = RNA  length = 80
FEATURE                Location/Qualifiers
source                 1..80
                       mol_type = other RNA
                       organism = Homo sapiens
SEQUENCE: 2
cctgttgcca caaacccgta gatccgaact tgtggtatta gtccgcacaa gcttgtatct   60
ataggtatgt gtctgttagg                                               80

SEQ ID NO: 3           moltype = RNA  length = 70
FEATURE                Location/Qualifiers
source                 1..70
                       mol_type = other RNA
                       organism = Homo sapiens
SEQUENCE: 3
ggcacccacc cgtagaaccg accttgcggg gccttcgccg cacacaagct cgtgtctgtg   60
ggtccgtgtc                                                          70

SEQ ID NO: 4           moltype = RNA  length = 70
FEATURE                Location/Qualifiers
source                 1..70
                       mol_type = other RNA
                       organism = Homo sapiens
SEQUENCE: 4
ggcacccacc cgtagaaccg accttgcggg gccttcgccg cacacaagct cgtgtctgtg   60
ggtccgtgtc                                                          70

SEQ ID NO: 5           moltype = RNA  length = 81
FEATURE                Location/Qualifiers
source                 1..81
```

```
                    mol_type = other RNA
                    organism = Homo sapiens
SEQUENCE: 5
cccattggca taaacccgta gatccgatct tgtggtgaag tggaccgcac aagctcgctt    60
ctatgggtct gtgtcagtgt g                                              81

SEQ ID NO: 6            moltype = RNA   length = 81
FEATURE                 Location/Qualifiers
source                  1..81
                        mol_type = other RNA
                        organism = Homo sapiens
SEQUENCE: 6
cccattggca taaacccgta gatccgatct tgtggtgaag tggaccgcac aagctcgctt    60
ctatgggtct gtgtcagtgt g                                              81

SEQ ID NO: 7            moltype = RNA   length = 99
FEATURE                 Location/Qualifiers
source                  1..99
                        mol_type = other RNA
                        organism = Homo sapiens
SEQUENCE: 7
gaaactgggc tcaaggtgag gggtgctatc tgtgattgag ggacatggtt aatggaattg    60
tctcacacag aaatcgcacc cgtcaccttg gcctactta                           99

SEQ ID NO: 8            moltype = RNA   length = 85
FEATURE                 Location/Qualifiers
source                  1..85
                        mol_type = other RNA
                        organism = Homo sapiens
SEQUENCE: 8
cgctggcgac gggacattat tactttggt acgcgctgtg acacttcaaa ctcgtaccgt     60
gagtaataat gcgccgtcca cggca                                          85

SEQ ID NO: 9            moltype = RNA   length = 85
FEATURE                 Location/Qualifiers
source                  1..85
                        mol_type = other RNA
                        organism = Homo sapiens
SEQUENCE: 9
cgctggcgac gggacattat tactttggt acgcgctgtg acacttcaaa ctcgtaccgt     60
gagtaataat gcgccgtcca cggca                                          85

SEQ ID NO: 10           moltype = RNA   length = 89
FEATURE                 Location/Qualifiers
source                  1..89
                        mol_type = other RNA
                        organism = Homo sapiens
SEQUENCE: 10
tgctgctggc cagagctctt ttcacattgt gctactgtct gcacctgtca ctagcagtgc    60
aatgttaaaa gggcattggc cgtgtagtg                                      89

SEQ ID NO: 11           moltype = RNA   length = 89
FEATURE                 Location/Qualifiers
source                  1..89
                        mol_type = other RNA
                        organism = Homo sapiens
SEQUENCE: 11
tgctgctggc cagagctctt ttcacattgt gctactgtct gcacctgtca ctagcagtgc    60
aatgttaaaa gggcattggc cgtgtagtg                                      89

SEQ ID NO: 12           moltype = RNA   length = 77
FEATURE                 Location/Qualifiers
source                  1..77
                        mol_type = other RNA
                        organism = Homo sapiens
SEQUENCE: 12
ggcagtgctc tactcaaaaa gctgtcagtc acttagatta catgtgactg acacctcttt    60
gggtgaagga aggctca                                                   77

SEQ ID NO: 13           moltype = RNA   length = 77
FEATURE                 Location/Qualifiers
source                  1..77
                        mol_type = other RNA
                        organism = Homo sapiens
SEQUENCE: 13
ggcagtgctc tactcaaaaa gctgtcagtc acttagatta catgtgactg acacctcttt    60
gggtgaagga aggctca                                                   77

SEQ ID NO: 14           moltype = RNA   length = 84
```

```
FEATURE                 Location/Qualifiers
source                  1..84
                        mol_type = other RNA
                        organism = Homo sapiens
SEQUENCE: 14
gcatccgggt tgaggtagta ggttgtatgg tttagagtta caccctggga gttaactgta    60
caaccttcta gctttccttg gagc                                          84

SEQ ID NO: 15           moltype = RNA  length = 84
FEATURE                 Location/Qualifiers
source                  1..84
                        mol_type = other RNA
                        organism = Homo sapiens
SEQUENCE: 15
gcatccgggt tgaggtagta ggttgtatgg tttagagtta caccctggga gttaactgta    60
caaccttcta gctttccttg gagc                                          84

SEQ ID NO: 16           moltype = RNA  length = 84
FEATURE                 Location/Qualifiers
source                  1..84
                        mol_type = other RNA
                        organism = Homo sapiens
SEQUENCE: 16
ctccccatgg ccctgtctcc caaccttgt accagtgctg ggctcagacc ctggtacagg     60
cctggggac agggacctgg ggac                                           84

SEQ ID NO: 17           moltype = RNA  length = 84
FEATURE                 Location/Qualifiers
source                  1..84
                        mol_type = other RNA
                        organism = Homo sapiens
SEQUENCE: 17
ctccccatgg ccctgtctcc caaccttgt accagtgctg ggctcagacc ctggtacagg     60
cctggggac agggacctgg ggac                                           84

SEQ ID NO: 18           moltype = RNA  length = 80
FEATURE                 Location/Qualifiers
source                  1..80
                        mol_type = other RNA
                        organism = Homo sapiens
SEQUENCE: 18
aggacccttc cagagggccc ccctcaatc ctgttgtgcc taattcagag ggttgggtgg     60
aggctctcct gaagggctct                                               80

SEQ ID NO: 19           moltype = RNA  length = 80
FEATURE                 Location/Qualifiers
source                  1..80
                        mol_type = other RNA
                        organism = Homo sapiens
SEQUENCE: 19
aggacccttc cagagggccc ccctcaatc ctgttgtgcc taattcagag ggttgggtgg     60
aggctctcct gaagggctct                                               80

SEQ ID NO: 20           moltype = RNA  length = 71
FEATURE                 Location/Qualifiers
source                  1..71
                        mol_type = other RNA
                        organism = Homo sapiens
SEQUENCE: 20
gccaacccag tgttcagact acctgttcag gaggctctca atgtgtacag tagtctgcac    60
attggttagg c                                                        71

SEQ ID NO: 21           moltype = RNA  length = 71
FEATURE                 Location/Qualifiers
source                  1..71
                        mol_type = other RNA
                        organism = Homo sapiens
SEQUENCE: 21
gccaacccag tgttcagact acctgttcag gaggctctca atgtgtacag tagtctgcac    60
attggttagg c                                                        71

SEQ ID NO: 22           moltype = RNA  length = 69
FEATURE                 Location/Qualifiers
source                  1..69
                        mol_type = other RNA
                        organism = Homo sapiens
SEQUENCE: 22
ccaccactta aacgtggatg tacttgcttt gaaactaaag aagtaagtgc ttccatgttt    60
tggtgatgg                                                           69
```

```
SEQ ID NO: 23          moltype = RNA   length = 69
FEATURE                Location/Qualifiers
source                 1..69
                       mol_type = other RNA
                       organism = Homo sapiens
SEQUENCE: 23
ccaccactta aacgtggatg tacttgcttt gaaactaaag aagtaagtgc ttccatgttt    60
tggtgatgg                                                            69

SEQ ID NO: 24          moltype = RNA   length = 22
FEATURE                Location/Qualifiers
source                 1..22
                       mol_type = other RNA
                       organism = Homo sapiens
SEQUENCE: 24
aacccgtaga tccgaacttg tg                                             22

SEQ ID NO: 25          moltype = RNA   length = 22
FEATURE                Location/Qualifiers
source                 1..22
                       mol_type = other RNA
                       organism = Homo sapiens
SEQUENCE: 25
caagcttgta tctataggta tg                                             22

SEQ ID NO: 26          moltype = RNA   length = 22
FEATURE                Location/Qualifiers
source                 1..22
                       mol_type = other RNA
                       organism = Homo sapiens
SEQUENCE: 26
cacccgtaga accgaccttg cg                                             22

SEQ ID NO: 27          moltype = RNA   length = 22
FEATURE                Location/Qualifiers
source                 1..22
                       mol_type = other RNA
                       organism = Homo sapiens
SEQUENCE: 27
caagctcgtg tctgtgggtc cg                                             22

SEQ ID NO: 28          moltype = RNA   length = 22
FEATURE                Location/Qualifiers
source                 1..22
                       mol_type = other RNA
                       organism = Homo sapiens
SEQUENCE: 28
aacccgtaga tccgatcttg tg                                             22

SEQ ID NO: 29          moltype = RNA   length = 22
FEATURE                Location/Qualifiers
source                 1..22
                       mol_type = other RNA
                       organism = Homo sapiens
SEQUENCE: 29
caagctcgct tctatgggtc tg                                             22

SEQ ID NO: 30          moltype = RNA   length = 23
FEATURE                Location/Qualifiers
source                 1..23
                       mol_type = other RNA
                       organism = Homo sapiens
SEQUENCE: 30
tctcacacag aaatcgcacc cgt                                            23

SEQ ID NO: 31          moltype = RNA   length = 21
FEATURE                Location/Qualifiers
source                 1..21
                       mol_type = other RNA
                       organism = Homo sapiens
SEQUENCE: 31
cattattact tttggtacgc g                                              21

SEQ ID NO: 32          moltype = RNA   length = 22
FEATURE                Location/Qualifiers
source                 1..22
                       mol_type = other RNA
                       organism = Homo sapiens
```

```
SEQUENCE: 32
tcgtaccgtg agtaataatg cg                                              22

SEQ ID NO: 33           moltype = RNA   length = 22
FEATURE                 Location/Qualifiers
source                  1..22
                        mol_type = other RNA
                        organism = Homo sapiens
SEQUENCE: 33
ttcacattgt gctactgtct gc                                              22

SEQ ID NO: 34           moltype = RNA   length = 22
FEATURE                 Location/Qualifiers
source                  1..22
                        mol_type = other RNA
                        organism = Homo sapiens
SEQUENCE: 34
cagtgcaatg ttaaaagggc at                                              22

SEQ ID NO: 35           moltype = RNA   length = 21
FEATURE                 Location/Qualifiers
source                  1..21
                        mol_type = other RNA
                        organism = Homo sapiens
SEQUENCE: 35
tactcaaaaa gctgtcagtc a                                               21

SEQ ID NO: 36           moltype = RNA   length = 22
FEATURE                 Location/Qualifiers
source                  1..22
                        mol_type = other RNA
                        organism = Homo sapiens
SEQUENCE: 36
gactgacacc tctttgggtg aa                                              22

SEQ ID NO: 37           moltype = RNA   length = 22
FEATURE                 Location/Qualifiers
source                  1..22
                        mol_type = other RNA
                        organism = Homo sapiens
SEQUENCE: 37
tgaggtagta ggttgtatgg tt                                              22

SEQ ID NO: 38           moltype = RNA   length = 22
FEATURE                 Location/Qualifiers
source                  1..22
                        mol_type = other RNA
                        organism = Homo sapiens
SEQUENCE: 38
ctgtacaacc ttctagcttt cc                                              22

SEQ ID NO: 39           moltype = RNA   length = 22
FEATURE                 Location/Qualifiers
source                  1..22
                        mol_type = other RNA
                        organism = Homo sapiens
SEQUENCE: 39
tctcccaacc cttgtaccag tg                                              22

SEQ ID NO: 40           moltype = RNA   length = 22
FEATURE                 Location/Qualifiers
source                  1..22
                        mol_type = other RNA
                        organism = Homo sapiens
SEQUENCE: 40
ctggtacagg cctgggggac ag                                              22

SEQ ID NO: 41           moltype = RNA   length = 21
FEATURE                 Location/Qualifiers
source                  1..21
                        mol_type = other RNA
                        organism = Homo sapiens
SEQUENCE: 41
agggccccca ctcaatcctg t                                               21

SEQ ID NO: 42           moltype = RNA   length = 22
FEATURE                 Location/Qualifiers
source                  1..22
                        mol_type = other RNA
```

-continued

```
                        organism = Homo sapiens
SEQUENCE: 42
gagggttggg tggaggctct cc                                              22

SEQ ID NO: 43           moltype = RNA   length = 23
FEATURE                 Location/Qualifiers
source                  1..23
                        mol_type = other RNA
                        organism = Homo sapiens
SEQUENCE: 43
cccagtgttc agactacctg ttc                                             23

SEQ ID NO: 44           moltype = RNA   length = 22
FEATURE                 Location/Qualifiers
source                  1..22
                        mol_type = other RNA
                        organism = Homo sapiens
SEQUENCE: 44
acagtagtct gcacattggt ta                                              22

SEQ ID NO: 45           moltype = RNA   length = 23
FEATURE                 Location/Qualifiers
source                  1..23
                        mol_type = other RNA
                        organism = Homo sapiens
SEQUENCE: 45
acttaaacgt ggatgtactt gct                                             23

SEQ ID NO: 46           moltype = RNA   length = 23
FEATURE                 Location/Qualifiers
source                  1..23
                        mol_type = other RNA
                        organism = Homo sapiens
SEQUENCE: 46
taagtgcttc catgttttgg tga                                             23

SEQ ID NO: 47           moltype = RNA   length = 22
FEATURE                 Location/Qualifiers
source                  1..22
                        mol_type = other RNA
                        organism = Homo sapiens
SEQUENCE: 47
agaggtagta ggttgcatag tt                                              22

SEQ ID NO: 48           moltype = RNA   length = 22
FEATURE                 Location/Qualifiers
source                  1..22
                        mol_type = other RNA
                        organism = Homo sapiens
SEQUENCE: 48
tgaggtagta gattgtatag tt                                              22

SEQ ID NO: 49           moltype = RNA   length = 22
FEATURE                 Location/Qualifiers
source                  1..22
                        mol_type = other RNA
                        organism = Homo sapiens
SEQUENCE: 49
tgaggtagta gtttgtacag tt                                              22

SEQ ID NO: 50           moltype = RNA   length = 22
FEATURE                 Location/Qualifiers
source                  1..22
                        mol_type = other RNA
                        organism = Homo sapiens
SEQUENCE: 50
tgaggtagta gtttgtgctg tt                                              22

SEQ ID NO: 51           moltype = RNA   length = 22
FEATURE                 Location/Qualifiers
source                  1..22
                        mol_type = other RNA
                        organism = Homo sapiens
SEQUENCE: 51
tagcagcaca tcatggttta ca                                              22

SEQ ID NO: 52           moltype = RNA   length = 23
FEATURE                 Location/Qualifiers
source                  1..23
```

```
                        mol_type = other RNA
                        organism = Homo sapiens
SEQUENCE: 52
taaagtgctt atagtgcagg tag                                              23

SEQ ID NO: 53           moltype = RNA  length = 23
FEATURE                 Location/Qualifiers
source                  1..23
                        mol_type = other RNA
                        organism = Homo sapiens
SEQUENCE: 53
caaagtgctc atagtgcagg tag                                              23

SEQ ID NO: 54           moltype = RNA  length = 22
FEATURE                 Location/Qualifiers
source                  1..22
                        mol_type = other RNA
                        organism = Homo sapiens
SEQUENCE: 54
aagctgccag ttgaagaact gt                                               22

SEQ ID NO: 55           moltype = RNA  length = 21
FEATURE                 Location/Qualifiers
source                  1..21
                        mol_type = other RNA
                        organism = Homo sapiens
SEQUENCE: 55
atcacattgc cagggatttc c                                                21

SEQ ID NO: 56           moltype = RNA  length = 22
FEATURE                 Location/Qualifiers
source                  1..22
                        mol_type = other RNA
                        organism = Homo sapiens
SEQUENCE: 56
tggctcagtt cagcaggaac ag                                               22

SEQ ID NO: 57           moltype = RNA  length = 22
FEATURE                 Location/Qualifiers
source                  1..22
                        mol_type = other RNA
                        organism = Homo sapiens
SEQUENCE: 57
ttcaagtaat ccaggatagg ct                                               22

SEQ ID NO: 58           moltype = RNA  length = 21
FEATURE                 Location/Qualifiers
source                  1..21
                        mol_type = other RNA
                        organism = Homo sapiens
SEQUENCE: 58
ttcacagtgg ctaagttccg c                                                21

SEQ ID NO: 59           moltype = RNA  length = 22
FEATURE                 Location/Qualifiers
source                  1..22
                        mol_type = other RNA
                        organism = Homo sapiens
SEQUENCE: 59
tagcaccatt tgaaatcggt ta                                               22

SEQ ID NO: 60           moltype = RNA  length = 21
FEATURE                 Location/Qualifiers
source                  1..21
                        mol_type = other RNA
                        organism = Homo sapiens
SEQUENCE: 60
gtgcattgta gttgcattgc a                                                21

SEQ ID NO: 61           moltype = RNA  length = 22
FEATURE                 Location/Qualifiers
source                  1..22
                        mol_type = other RNA
                        organism = Homo sapiens
SEQUENCE: 61
tgaggtagta agttgtattg tt                                               22

SEQ ID NO: 62           moltype = RNA  length = 23
FEATURE                 Location/Qualifiers
```

-continued

```
source                  1..23
                        mol_type = other RNA
                        organism = Homo sapiens
SEQUENCE: 62
agcagcattg tacagggcta tca                                              23

SEQ ID NO: 63           moltype = RNA   length = 23
FEATURE                 Location/Qualifiers
source                  1..23
                        mol_type = other RNA
                        organism = Homo sapiens
SEQUENCE: 63
tgtagtgttt cctactttat gga                                              23

SEQ ID NO: 64           moltype = RNA   length = 23
FEATURE                 Location/Qualifiers
source                  1..23
                        mol_type = other RNA
                        organism = Homo sapiens
SEQUENCE: 64
gtccagtttt cccaggaatc cct                                              23

SEQ ID NO: 65           moltype = RNA   length = 22
FEATURE                 Location/Qualifiers
source                  1..22
                        mol_type = other RNA
                        organism = Homo sapiens
SEQUENCE: 65
tgagaactga attccatggg tt                                               22

SEQ ID NO: 66           moltype = RNA   length = 22
FEATURE                 Location/Qualifiers
source                  1..22
                        mol_type = other RNA
                        organism = Homo sapiens
SEQUENCE: 66
tcagtgcact acagaacttt gt                                               22

SEQ ID NO: 67           moltype = RNA   length = 23
FEATURE                 Location/Qualifiers
source                  1..23
                        mol_type = other RNA
                        organism = Homo sapiens
SEQUENCE: 67
aacattcaac gctgtcggtg agt                                              23

SEQ ID NO: 68           moltype = RNA   length = 23
FEATURE                 Location/Qualifiers
source                  1..23
                        mol_type = other RNA
                        organism = Homo sapiens
SEQUENCE: 68
caacggaatc ccaaaagcag ctg                                              23

SEQ ID NO: 69           moltype = RNA   length = 22
FEATURE                 Location/Qualifiers
source                  1..22
                        mol_type = other RNA
                        organism = Homo sapiens
SEQUENCE: 69
taacactgtc tggtaacgat gt                                               22

SEQ ID NO: 70           moltype = RNA   length = 23
FEATURE                 Location/Qualifiers
source                  1..23
                        mol_type = other RNA
                        organism = Homo sapiens
SEQUENCE: 70
tcaagagcaa taacgaaaaa tgt                                              23

SEQ ID NO: 71           moltype = RNA   length = 22
FEATURE                 Location/Qualifiers
source                  1..22
                        mol_type = other RNA
                        organism = Homo sapiens
SEQUENCE: 71
ctcctatatg atgcctttct tc                                               22

SEQ ID NO: 72           moltype = RNA   length = 22
```

```
FEATURE              Location/Qualifiers
source               1..22
                     mol_type = other RNA
                     organism = Homo sapiens
SEQUENCE: 72
ttataaagca atgagactga tt                                                    22

SEQ ID NO: 73        moltype = RNA  length = 23
FEATURE              Location/Qualifiers
source               1..23
                     mol_type = other RNA
                     organism = Homo sapiens
SEQUENCE: 73
tgagggcag agagcgagac ttt                                                    23

SEQ ID NO: 74        moltype = RNA  length = 22
FEATURE              Location/Qualifiers
source               1..22
                     mol_type = other RNA
                     organism = Homo sapiens
SEQUENCE: 74
cacgctcatg cacacaccca ca                                                    22

SEQ ID NO: 75        moltype = RNA  length = 19
FEATURE              Location/Qualifiers
source               1..19
                     mol_type = other RNA
                     organism = Homo sapiens
SEQUENCE: 75
tgtctctgct ggggtttct                                                        19

SEQ ID NO: 76        moltype = RNA  length = 21
FEATURE              Location/Qualifiers
source               1..21
                     mol_type = other RNA
                     organism = Homo sapiens
SEQUENCE: 76
agaggatacc ctttgtatgt t                                                     21

SEQ ID NO: 77        moltype = RNA  length = 19
FEATURE              Location/Qualifiers
source               1..19
                     mol_type = other RNA
                     organism = Homo sapiens
SEQUENCE: 77
atcccaccac tgccaccat                                                        19

SEQ ID NO: 78        moltype = RNA  length = 20
FEATURE              Location/Qualifiers
source               1..20
                     mol_type = other RNA
                     organism = Homo sapiens
SEQUENCE: 78
ggatccgagt cacggcacca                                                       20
```

MICRORNA ASSAY FOR DETECTION AND MANAGEMENT OF PANCREATIC CANCER PRECURSORS

CROSS-REFERENCE TO RELATED APPLICATIONS

The present application is a continuation of U.S. application Ser. No. 17/554,476, filed Dec. 17, 2021, which is a continuation of U.S. application Ser. No. 17/233,855, filed Apr. 19, 2021, which is a continuation of U.S. application Ser. No. 16/362,623, filed Mar. 23, 2019, which is a continuation of U.S. application Ser. No. 15/300,808, filed Sep. 30, 2016, now U.S. Pat. No. 10,240,208, which is the National Stage of International Application Number PCT/US2015/023702, filed Mar. 31, 2015, which claims the benefit of U.S. Provisional Application Serial No. 61/973,068, filed Mar. 31, 2014, each of which is hereby incorporated by reference herein in its entirety, including any figures, tables, nucleic acid sequences, amino acid sequences, or drawings.

GOVERNMENT SUPPORT

This invention was made with government support under grant numbers CA076292 and CA129227 awarded by the National Institutes of Health. The government has certain rights in the invention.

SEQUENCE LISTING

The Sequence Listing for this application is labeled "2SN9055.TXT" which was created on Dec. 16, 2021 and is 13.5 KB. The entire contents of the sequence listing is incorporated herein by reference in its entirety.

BACKGROUND OF THE INVENTION

Intraductal papillary mucinous neoplasms (IPMN) are incidentally-detected pancreatic cysts that are challenging to manage due to the inability to predict which cysts can be safely monitored, which are likely to progress to invasive pancreatic cancer, and which may have an associated invasive component. Differentiating between high-risk and low-risk intraductal papillary mucinous neoplasms (IPMNs) of the pancreas is a significant clinical problem.

Pancreatic ductal adenocarcinoma (PDAC) is the fourth leading cause of cancer mortality in the United States, claiming the lives of nearly 40,000 individuals each year. Surgical resection offers the best chance for improved survival, but 80-85% of cases are unresectable at diagnosis. These statistics underscore the urgent need to develop strategies to detect PDAC at an early, operable stage.

It is established that PDAC does not arise de novo, but instead marks the end of progression from one of three types of non-invasive precursor lesions arising within exocrine pancreatic ducts: pancreatic intraepithelial neoplasia (PanIN), mucinous cystic neoplasms (MCNs), and intraductal papillary mucinous neoplasms (IPMNs). While PanINs are microscopic lesions in ducts <5 mm in diameter, MCNs and IPMNs are macroscopic mucinous cysts accounting for over half of the estimated 150,000 asymptomatic pancreatic cysts detected incidentally in the general population each year due to increased computed tomography and magnetic resonance imaging. Although improvements in imaging, cytology, and molecular studies have enabled proper classification and management of some benign non-neoplastic pancreatic cysts, mucinous cysts such as IPMNs are challenging for the patient and clinical team to manage due to the inability to accurately predict which lesions can be monitored, which are likely to progress to invasion, and which may have an associated invasive component. Since data highlight a two-decade window of opportunity for early detection efforts in PDAC, IPMNs represent prime targets for the early detection and prevention of progression to invasive, fatal disease.

IPMNs present within the main pancreatic duct (MD-IPMN), side branch ducts (BD-IPMN), or both (mixed-IPMN), and are further classified based on the degree of dysplasia which ranges from adenoma (low-grade dysplasia, LG) and borderline (moderate-grade dysplasia, MG) to carcinoma in situ (high-grade dysplasia, HG) and invasive carcinoma (2) (FIGS. 4A-4D). MD-IPMNs are associated with a higher grade and faster growth compared to BD-IPMNs, with the 5-year risk of developing HG or invasive disease from an adenoma to be ~63% for MD-IPMNs and 15% for BD-IPMNs. Other predictors of malignant potential include main duct dilation (>5 mm), mural nodules, cyst size (>3 cm), and symptoms such as jaundice and abdominal pain. Consensus guidelines recommend resection for surgically-fit patients with MD-IPMNs and careful observation for asymptomatic BD-IPMNs measuring <3 cm in the absence of mural nodules, main-duct dilation, or positive cytology. However, these guidelines do not reliably predict the degree of dysplasia. To date, the only way to treat IPMNs and accurately identify the grade of dysplasia is through surgical resection and pathological evaluation, but the risks of morbidity (i.e. long-term diabetes) and mortality associated with a Whipple procedure or a distal or total pancreatectomy may outweigh the benefits, especially for patients with LG disease. Alternatively, taking a 'watch and wait' approach could lead to a missed opportunity to cure a patient harboring occult invasive disease.

Although many DNA-, RNA- and protein-based markers are under investigation as markers of early pancreatic neoplasia, most require further validation. MicroRNAs (miRNAs) are small non-coding RNAs that regulate nearly one-third of all protein-coding genes by binding to the 3' untranslated region of the targeted messenger RNA (mRNA). Their ability to regulate (and serve as) tumor suppressors and oncogenes, their remarkable stability in formalin-fixed paraffin-embedded (FFPE) tissue and biofluids, and their dysregulated expression in PDACs compared to normal pancreas tissue makes miRNAs excellent candidate biomarkers of early progression to pancreatic malignancy. Indeed, early studies of small numbers of miRNAs supported a role for altered miRNA expression in PanINs and IPMNs. Since over 1,000 miRNAs exist (21), we sought to conduct the first genome-wide investigation of miRNAs to be followed by both a replication and a functional follow-up phase (FIG. 5), with the goal of discovering miRNAs that accurately differentiate high-risk (HG and invasive) IPMNs that may require resection from low-risk (LG and MG) IPMNs that can be monitored.

BRIEF SUMMARY OF THE INVENTION

Certain embodiments of the current invention provide miRNAs that are differentially expressed in a sample of an individual having pancreatic cancer, or having a high risk of developing pancreatic cancer, as compared to the corresponding sample of an individual not having pancreatic cancer, or having low risk of developing pancreatic cancer. In one embodiment, each of the individuals having high risk of developing pancreatic cancer and the individual having low risk of developing pancreatic cancer have a non-invasive precursor lesion arising within exocrine pancreatic ducts (hereinafter, pancreatic lesion), for example, pancreatic intraepithelial neoplasia (PanIN), mucinous cystic neoplasms (MCNs), and intraductal papillary mucinous neoplasms (IPMNs). The miRNAs that are differentially expressed in a sample of an individual having pancreatic cancer, or having a high risk of developing pancreatic cancer, can be used as biomarkers for diagnosis, treatment, and/or prevention of pancreatic cancer.

The miRNAs identified herein can be used to identify subjects that have pancreatic cancer to distinguish them from subjects that do not have pancreatic cancer, or to identify subjects having a higher risk of developing pancreatic cancer to distinguish them from subjects that have a lower risk of developing pancreatic cancer, or to identify subjects having a pancreatic cancer precursor (such as intraductal papillary mucinous neoplasm (IPMN)) versus a non-IPMN, or to identify subjects that have a malignant IPMN versus a benign IPMN. Thus, these miRNAs can be used as an adjunctive tool to guide decisions regarding monitoring, treatment, and management of pancreatic cancer.

Certain other embodiments of the current invention provide microarrays of oligonucleotides corresponding to the miRNAs that are differentially expressed in a sample of an individual having pancreatic cancer, or having a high risk of developing pancreatic cancer, for example, when the individual has a pancreatic lesion. In one embodiment, the sample is a cell sample, such as a blood cell, and accordingly, the current invention also provides a blood-based minimally-invasive miRNA assay that can be used in an individual having a pancreatic lesion to assess histologic severity. In another embodiment, the miRNAs indicative of pancreatic cancer are detected in cell-free samples from a subject, for example, body fluid samples from a subject, such as whole blood, plasma, serum, urine, or pancreatic cyst fluid. As such, the current invention provides miRNAs that can be used to differentiate between the presence or absence of pancreatic cancer, high-risk or low-risk pancreatic lesions, for example, IPMNs, that warrant treatment (such as surgical resection, pancreatoduodenectomy (Whipple procedure), immunotherapy, radition, or chemotherapy) and low-risk pancreatic lesions, for example, IPMNs, that can be monitored. Monitoring and confirmation of the presence of pancreatic cancer or lesions can be carried out, for example, by imaging (e.g., endoscopic ultrasound, MM, or CT scan).

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIG. 2A: The heatmap is supervised, and is ordered by the type of IPMN, and shows the expression for the 25 most deregulated miRNAs. FIG. 2B: Unsupervised hierarchical clustering for the 6 most differentially expressed miRNAs. Expression values for the miRNAs are represented in a matrix format, with columns representing samples and rows representing miRNAs.

FIG. 6A: Discovery phase; FIG. 6B: Replication phase. On each boxplot, the central mark is the median, and the edges of the box are the 25th and 75th percentiles. The whiskers extend to the most extreme data points within 1.5 of the interquartile range above the $75^{th}$ or below the $25^{th}$ percentiles. Data points beyond the whiskers, displayed using "o", are potential outliers.

FIG. 10A: Percentage of variation explained in the first 5 principal components using the 30 miRNA signature. FIG. 10B: Association of the 30-miRNA signature with case-control status. Box plots were used to display the distribution of the IPMN-risk malignancy score within each group. Two-sample t-tests were used to determine associations between the continuous PC1 score and case-control status. FIG. 10C: Receiver operating characteristic (ROC) curve analysis using miRNA expression to discriminate IPMN cases from healthy controls. The 30-miRNA signature PC1 yielded an area underneath the curve (AUC) value of 74.4 (95% CI: 62.3-86.5) in differentiating between groups.

FIG. 12A: Box plot reveals miR-145-5p expression is higher in cases versus controls. FIG. 12B: ROC analysis reveals that miR-145-5p expression can differentiate between groups with an AUC=79.3 (95% CI: 68.3-90.3).

FIGS. 13A-13D. Heatmap of the KEGG pathways enriched for genes targeted by the 30 differentially expressed miRNAs.

FIG. 14A: Percentage of variation explained in the 5 principal components using the 5 miRNA signature. FIG. 14B: Association of the 5-miRNA signature with IPMN malignancy status. Box plots were used to display the distribution of the IPMN-risk malignancy score within each group. Two-sample t-tests were used to determine associations between the continuous PC1 score and IPMN malignancy status. FIG. 14C: ROC curve analysis of the 5-miRNA signature yielded an AUC of 73.2 (95% CI: 57.6-88.9) in differentiating between groups.

BRIEF DESCRIPTION OF THE SEQUENCES

Figures 1A, 1B:
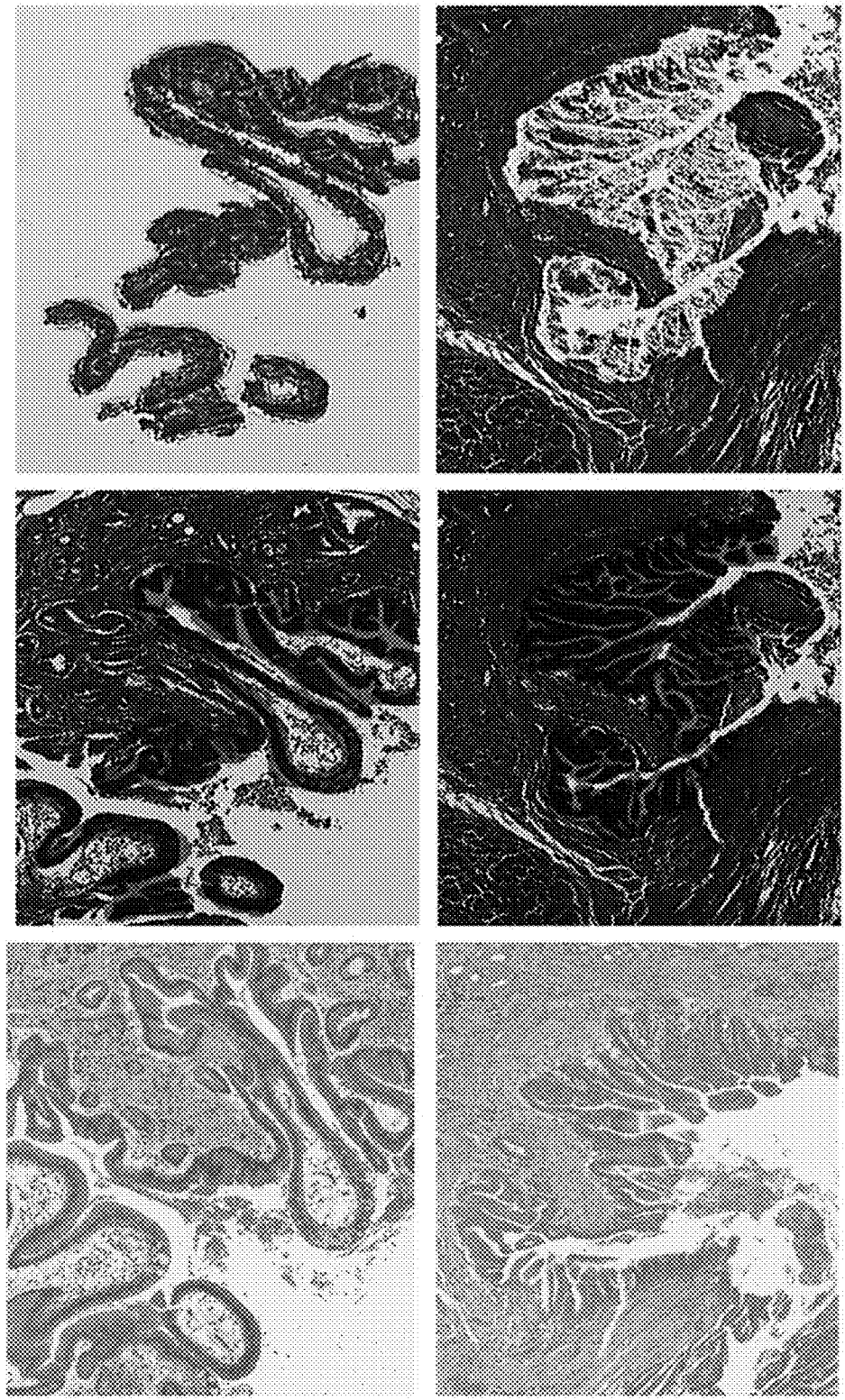
FIGS. 1A and 1B. Laser capture microdissection (LCM) of epithelium from low-grade IPMN tissue (FIG. 1A) and high-grade IPMN tissue (FIG. 1B). Left Panel: Hematoxylin (H&E) stained slide (×4). Middle Panel: H&E stained slide before LCM (×4), with the red area representing cells of interest marked for capture. Right Panel: Cap showing adherent cells.

| miRNA | SEQ ID NO: | Pre-miRNA | SEQ ID NO: | Mature miRNA |
|---|---|---|---|---|
| hsa-miR-100-5p | 1 | CCUGUUGCCACAAACCCGUAGAUCCGAA CUUGUGGUAUUAGUCCGCACAAGCUUG UAUCUAUAGGUAUGUGUCUGUUAGG | 24 | AACCCGUAGAUCCGA ACUUGUG |
| hsa-miR-100-3p | 2 | CCUGUUGCCACAAACCCGUAGAUCCGAA CUUGUGGUAUUAGUCCGCACAAGCUUG UAUCUAUAGGUAUGUGUCUGUUAGG | 25 | CAAGCUUGUAUCUA UAGGUAUG |
| hsa-miR-99b-5p | 3 | GGCACCCACCCGUAGAACCGACCUUGCG GGGCCUUCGCCGCACACAAGCUCGUGUC UGUGGGUCCGUGUC | 26 | CACCCGUAGAACCGA CCUUGCG |
| hsa-miR-99b-3p | 4 | GGCACCCACCCGUAGAACCGACCUUGCG GGGCCUUCGCCGCACACAAGCUCGUGUC UGUGGGUCCGUGUC | 27 | CAAGCUCGUGUCUG UGGGUCCG |
| hsa-miR-99a-5p | 5 | CCCAUUGGCAUAAACCCGUAGAUCCGAU CUUGUGGUGAAGUGGACCGCACAAGCU CGCUUCUAUGGGUCUGUGUCAGUGUG | 28 | AACCCGUAGAUCCGA UCUUGUG |
| hsa-miR-99a-5p | 6 | CCCAUUGGCAUAAACCCGUAGAUCCGAU CUUGUGGUGAAGUGGACCGCACAAGCU CGCUUCUAUGGGUCUGUGUCAGUGUG | 29 | CAAGCUCGCUUCUA UGGGUCUG |
| hsa-miR-342-3p | 7 | GAAACUGGGCUCAAGGUGAGGGGUGCU AUCUGUGAUUGAGGGACAUGGUUAAUG GAAUUGUCUCACACAGAAAUCGCACCCG UCACCUUGGCCUACUUA | 30 | UCUCACACAGAAAUC GCACCCGU |
| hsa-miR-126-5p | 8 | CGCUGGCGACGGGACAUUAUUACUUUU GGUACGCGCUGUGACACUUCAAACUCG UACCGUGAGUAAUAAUGCGCCGUCCACG GCA | 31 | CAUUAUUACUUUUG GUACGCG |
| hsa-miR-126-3p | 9 | CGCUGGCGACGGGACAUUAUUACUUUU GGUACGCGCUGUGACACUUCAAACUCG UACCGUGAGUAAUAAUGCGCCGUCCACG GCA | 32 | UCGUACCGUGAGUA AUAAUGCG |
| hsa-miR-130a-5p | 10 | UGCUGCUGGCCAGAGCUCUUUUCACAU UGUGCUACUGUCUGCACCUGUCACUAG CAGUGCAAUGUUAAAAGGGCAUUGGCC GUGUAGUG | 33 | UUCACAUUGUGCUA CUGUCUGC |
| hsa-miR-130a-3p | 11 | UGCUGCUGGCCAGAGCUCUUUUCACAU UGUGCUACUGUCUGCACCUGUCACUAG CAGUGCAAUGUUAAAAGGGCAUUGGCC GUGUAGUG | 34 | CAGUGCAAUGUUAA AAGGGCAU |
| hsa-miR-888-5p | 12 | GGCAGUGCUCUACUCAAAAAGCUGUCA GUCACUUAGAUUACAUGUGACUGACAC CUCUUUGGGUGAAGGAAGGCUCA | 35 | UACUCAAAAAGCUG UCAGUCA |
| hsa-miR-888-3p | 13 | GGCAGUGCUCUACUCAAAAAGCUGUCA GUCACUUAGAUUACAUGUGACUGACAC CUCUUUGGGUGAAGGAAGGCUCA | 36 | GACUGACACCUCUU UGGGUGAA |

-continued

| miRNA | SEQ ID NO: | Pre-miRNA | SEQ. ID NO: | Mature miRNA |
|---|---|---|---|---|
| hsa-let-7c-5p | 14 | GCAUCCGGGUUGAGGUAGUAGGUUGUAUGGUUUAGAGUUACACCCUGGGAGUUAACUGUACAACCUUCUAGCUUUCCUUGGAGC | 37 | UGAGGUAGUAGGUUGUAUGGUU |
| hsa-let-7c-3p | 15 | GCAUCCGGGUUGAGGUAGUAGGUUGUAUGGUUUAGAGUUACACCCUGGGAGUUAACUGUACAACCUUCUAGCUUUCCUUGGAGC | 38 | CUGUACAACCUUCUAGCUUUCC |
| hsa-miR-150-5p | 16 | CUCCCCAUGGCCCUGUCUCCCAACCCUUGUACCAGUGCUGGGCUCAGACCCUGGUACAGGCCUGGGGGACAGGGACCUGGGGAC | 39 | UCUCCCAACCCUUGUACCAGUG |
| hsa-miR-150-3p | 17 | CUCCCCAUGGCCCUGUCUCCCAACCCUUGUACCAGUGCUGGGCUCAGACCCUGGUACAGGCCUGGGGGACAGGGACCUGGGGAC | 40 | CUGGUACAGGCCUGGGGACAG |
| hsa-miR-296-5p | 18 | AGGACCCUUCCAGAGGGCCCCCCCUCAAUCCUGUUGUGCCUAAUUCAGAGGGUUGGGUGGAGGCUCUCCUGAAGGGCUCU | 41 | AGGGCCCCCCCUCAAUCCUGU |
| hsa-miR-296-3p | 19 | AGGACCCUUCCAGAGGGCCCCCCCUCAAUCCUGUUGUGCCUAAUUCAGAGGGUUGGGUGGAGGCUCUCCUGAAGGGCUCU | 42 | GAGGGUUGGGUGGAGGCUCUCC |
| hsa-miR-199a-5p | 20 | GCCAACCCAGUGUUCAGACUACCUGUUCAGGAGGCUCUCAAUGUGUACAGUAGUCUGCACAUUGGUUAGGC | 43 | CCCAGUGUUCAGACUACCUGUUC |
| hsa-miR-199a-3p | 21 | GCCAACCCAGUGUUCAGACUACCUGUUCAGGAGGCUCUCAAUGUGUACAGUAGUCUGCACAUUGGUUAGGC | 44 | ACAGUAGUCUGCACAUUGGUUA |
| hsa-miR-302a-5p | 22 | CCACCACUUAAACGUGGAUGUACUUGCUUUGAAACUAAAGAAGUAAGUGCUUCCAUGUUUUGGUGAUGG | 45 | ACUUAAACGUGGAUGUACUUGCU |
| hsa-miR-302a-5p | 23 | CCACCACUUAAACGUGGAUGUACUUGCUUUGAAACUAAAGAAGUAAGUGCUUCCAUGUUUUGGUGAUGG | 46 | UAAGUGCUUCCAUGUUUUGGUGA |

| SEQ ID NO. | miRNA | Accession | Target Sequence |
|---|---|---|---|
| 47 | hsa-let-7d-5p | MIMAT0000065 | AGAGGUAGUAGGUUGCAUAGUU |
| 48 | hsa-let-7f-5p | MIMAT0000067 | UGAGGUAGUAGAUUGUAUAGUU |
| 49 | hsa-let-7g-5p | MIMAT0000414 | UGAGGUAGUAGUUUGUACAGUU |
| 50 | hsa-let-7i-5p | MIMAT0000415 | UGAGGUAGUAGUUUGUGCUGUU |
| 51 | hsa-miR-15b-5p | MIMAT0000417 | UAGCAGCACAUCAUGGUUUACA |
| 52 | hsa-miR-20a-5p*[2] | MIMAT0000075 | UAAAGUGCUUAUAGUGCAGGUAG |
| 53 | hsa-miR-20b-5p*[2] | MIMAT0001413 | CAAAGUGCUCAUAGUGCAGGUAG |
| 54 | hsa-miR-22-3p | MIMAT0000077 | AAGCUGCCAGUUGAAGAACUGU |
| 55 | hsa-miR-23a-3p | MIMAT0000078 | AUCACAUUGCCAGGGAUUUCC |
| 56 | hsa-miR-24-3p | MIMAT0000080 | UGGCUCAGUUCAGCAGGAACAG |
| 57 | hsa-miR-26a-5p | MIMAT0000082 | UUCAAGUAAUCCAGGAUAGGCU |
| 58 | hsa-miR-27a-3p | MIMAT0000084 | UUCACAGUGGCUAAGUUCCGC |
| 59 | hsa-miR-29c-3p | MIMAT0000681 | UAGCACCAUUUGAAAUCGGUUA |
| 60 | hsa-miR-33a-5p | MIMAT0000091 | GUGCAUUGUAGUUGCAUUGCA |

-continued

| SEQ ID NO. | miRNA | Accession | Target Sequence |
|---|---|---|---|
| 61 | hsa-miR-98 | MIMAT0000096 | UGAGGUAGUAAGUUGUAUUGUU |
| 62 | hsa-miR-107 | MIMAT0000104 | AGCAGCAUUGUACAGGGCUAUCA |
| 63 | hsa-miR-142-3p | MIMAT0000434 | UGUAGUGUUUCCUACUUUAUGGA |
| 64 | hsa-miR-145-5p | MIMAT0000437 | GUCCAGUUUUCCCAGGAAUCCCU |
| 65 | hsa-miR-146a-5p | MIMAT0000449 | UGAGAACUGAAUUCCAUGGGUU |
| 66 | hsa-miR-148a-3p | MIMAT0000243 | UCAGUGCACUACAGAACUUUGU |
| 67 | hsa-miR-181a-5p | MIMAT0000256 | AACAUUCAACGCUGUCGGUGAGU |
| 68 | hsa-miR-191-5p | MIMAT0000440 | CAACGGAAUCCCAAAAGCAGCUG |
| 44 | hsa-miR-199a-3p*[4] | MIMAT0000232 | ACAGUAGUCUGCACAUUGGUUA |
| 69 | hsa-miR-200a-3p | MIMAT0000682 | UAACACUGUCUGGUAACGAUGU |
| 70 | hsa-miR-335-5p | MIMAT0000765 | UCAAGAGCAAUAACGAAAAAUGU |
| 71 | hsa-miR-337-3p | MIMAT0000754 | CUCCUAUAUGAUGCCUUUCUUC |
| 72 | hsa-miR-340-5p | MIMAT0004692 | UUAUAAAGCAAUGAGACUGAUU |
| 73 | hsa-miR-423-5p | MIMAT0004748 | UGAGGGGCAGAGAGCGAGACUUU |
| 74 | hsa-miR-574-3p | MIMAT0003239 | CACGCUCAUGCACACACCCACA |
| 75 | hsa-miR-593-3p | MIMAT0004802 | UGUCUCUGCUGGGGUUUCU |
| 76 | hsa-miR-1185-5p | MIMAT0005798 | AGAGGAUACCCUUUGUAUGUU |
| 77 | hsa-miR-1260b | MIMAT0015041 | AUCCCACCACUGCCACCAU |
| 78 | hsa-miR-4454 | MIMAT0018976 | GGAUCCGAGUCACGGCACCA |

*miRNA species identified with an asterisk are targeted by a non-unique probe. All species targeted by the same probe share the same number after the asterisk.

DETAILED DESCRIPTION OF THE INVENTION

The term "about" is used in this patent application to describe some quantitative aspects of the invention, for example, length of a polynucleotide in terms of the number of nucleotides or base pairs. It should be understood that absolute accuracy is not required with respect to those aspects for the invention to operate. When the term "about" is used to describe a quantitative aspect of the invention the relevant aspect may be varied by ±10%. For example, a miRNA about 20 nucleotides long means a polynucleotide between 18 to 22 nucleotides long.

The phrase "one or more miRNAs" in the context of detecting the level of expression of miRNAs means that the level of at least one of the recited miRNAs is measured using an assay effective in measuring miRNA expression in the sample from the subject. For example, detecting the level of expression of one or more mRNAs selected from among miR-200a-3p, miR-1185-5p, miR-33a-5p, miR-574-3p, and miR-663b encompasses measuring the level of expression of one, two, three, four, or all five of the recited miRNAs, and may encompass detecting the level of expression of further unrecited miRNAs or only the recited miRNAs.

The current invention provides miRNAs that are indicative of the presence of pancreatic cancer, or high risk of developing pancreatic cancer, in a subject, particularly, when the subject has a pancreatic lesion. For the purposes of this invention, a "high risk of developing pancreatic cancer" indicates that the person has an increased risk of developing pancreatic cancer in the near future compared to an individual who is free from pancreatic cancer and has low risk of developing pancreatic cancer in the near future. For the purposes of this invention, the term "near future" refers to a duration of about 1 month to about 2 years, about 6 months to about 18 months, or about 1 year.

The pancreatic cancer may be of any category (e.g., TX, T0, Tis, T1, T2, T3, T4); any category (e.g., NX, N0, N1, M0, M1); any stage (Stage 0 (Tis, N0, M0), Stage IA (T1, N0, M0), Stage IIA (T3, N0, M0), Stage IIB (T1-3, N1, M0), Stage III (T4, Any N, M0), Stage IV (Any T, Any N, M1)); resectable; locally advanced (unresectable); or metastatic.

The miRNAs that are indicative of the presence of pancreatic cancer, or high risk of developing pancreatic cancer, in a subject can be used for diagnosing, treating, and/or preventing pancreatic cancer as early as possible, particularly, when the subject has a pancreatic lesion. The current invention also provides kits and microRNA microarrays (e.g., chips) that can be used in the diagnosis of pancreatic cancer or assessing the risk of developing pancreatic cancer in a subject, particularly, when the subject has a pancreatic lesion.

A miRNA is a small non-coding RNA molecule of about 20-25 nucleotides found in plants and animals. A miRNA functions in transcriptional and post-transcriptional regulation of gene expression. Encoded by eukaryotic nuclear DNA, miRNA functions via base-pairing with complementary sequences within mRNA molecules, usually resulting in gene silencing via translational repression or target degradation. miRNAs are transcribed by RNA polymerase II as large RNA precursors called pri-miRNAs. The pri-miRNAs are processed further in the nucleus to produce pre-miRNAs. Pre-miRNAs are about 70-nucleotides in length and are folded into imperfect stem-loop structures. The pre-miRNAs are then exported into the cytoplasm and undergo additional processing to generate miRNA. A miRNA profile of a sample indicates expression levels of various miRNAs in the sample.

A differentially expressed miRNA is the miRNA which is either over-expressed/up-regulated or under-expressed/down-regulated in a sample (e.g., test cell of a tissue sample compared to a control cell, or a cellular or acellular fluid sample, or a reference expression level (a reference value)). A reference expression level may reflect that of a "normal" state (lacking the disease) or the corresponding diseased state of interest in a relevant population (e.g., an epidemiologically relevant population), for example. In some embodiments, for the purposes of this invention, a miRNA is identified as a "differentially expressed miRNA" if the miRNA is expressed in the sample at least about 1.8 fold higher or lower than the corresponding miRNA in the control sample, or reference expression level, or the difference in the expression level between the sample and the control sample or reference expression level has statistical significance (p value) of less than 0.05. In some embodiments, miRNA is identified as a "differentially expressed miRNA" if the miRNA is expressed in the sample at about 2- to 4-fold higher or lower than the corresponding miRNA in the control sample or reference expression sample.

A profile of differentially expressed miRNAs represents a set of miRNAs that are differentially expressed in a fluid or tissue sample compared to a control/reference level. The profile of differentially expressed miRNAs comprises a profile of down-regulated/under-expressed miRNAs and a profile of up-regulated/over-expressed miRNAs.

Certain embodiments of the current invention provide miRNAs that are differentially expressed in a sample of an individual having high risk of developing pancreatic cancer as compared to the corresponding sample of an individual having low risk of developing pancreatic cancer. In one embodiment, each of the individual having high risk of developing pancreatic cancer and the individual having low risk of developing pancreatic cancer have a pancreatic lesion, for example, PanIN, MCNs, or IPMNs. The miRNAs that are differentially expressed in a cell of an individual having high risk of developing or having pancreatic cancer can be used as biomarkers for diagnosis and/or prevention of pancreatic cancer. For example, miRNAs differentially expressed in a cell of an individual having high risk of developing pancreatic cancer as compared to the corresponding cell of an individual having low risk of developing pancreatic cancer comprises one or more of, miR-100, miR-99b, miR-99a, miR-342-3p, miR-126, miR-888, miR-130a, let-7c, miR-150, miR-296, miR-199a, miR-199a-3p, and miR-302a, preferably, one or more of miR-100, miR-99b, miR-99a, miR-342-3p, miR-126, and miR-130a.

Various embodiments provide a profile of differentially expressed miRNAs in a sample of an individual having pancreatic cancer, or having high risk of developing pancreatic cancer, particularly, when the individual has a pancreatic lesion. The profile of differentially expressed miRNAs in a sample of an individual having pancreatic cancer, or having a high risk of developing pancreatic cancer, comprises use of a profile of up-regulated/over-expressed miRNAs and a profile of down-regulated/under-expressed miRNAs.

In some embodiments, the method for detecting in a subject the presence of pancreatic cancer, or a high risk of developing pancreatic cancer, comprises:

(a) detecting the level of expression of one or more miRNAs in a sample from the subject; and (b) comparing the detected expression level to a reference expression level, wherein a differential expression of the one or more miRNAs in the sample, as compared to the reference expression level, is indicative of the presence of pancreatic cancer, or a higher risk of developing pancreatic cancer, versus the absence of pancreatic cancer, or a lower risk of developing pancreatic cancer, respectively.

The differential expression of the one or more miRNAs in the sample, as compared to the reference expression level, may be indicative of a pancreatic cancer precursor (such as intraductal papillary mucinous neoplasm (IPMN)) versus non-IPMN (normal cells).

The differential expression of the one or more miRNAs in the sample, as compared to the reference expression level, may be indicative of a malignant intraductal papillary mucinous neoplasm (IPMN) versus a benign IPMN.

In some embodiments, the sample is a tissue sample, and the one or more miRNAs belong to a profile of miRNAs that are differentially expressed in a cell of an individual having a higher risk of developing pancreatic cancer as compared to the corresponding cell of an individual having lower risk of developing pancreatic cancer.

In some embodiments, the subject has a pancreatic lesion and the one or more miRNAs belong to a profile of differentially expressed miRNAs in a sample of an individual having a pancreatic lesion and having higher risk of developing pancreatic cancer compared to the corresponding sample of an individual having a pancreatic lesion and having lower risk of developing pancreatic cancer.

Various methods may be used for detecting the expression level of one or more miRNAs in a sample. For example, measurement of miRNA can be carried out by barcode-based assay, miRNA microarray analysis (e.g., chip), digital polymerase chain reaction (PCR), real-time PCR, quantitative reverse transcription PCR (qRT-PCR), semi-quantitative PCR, Northern blot, or in situ hybridization. Typically, the mature miRNA is measured, for example, using an in vitro assay.

In some embodiments, a profile of differentially expressed miRNAs comprise of one or more (optionally, all) of miR-100, miR-99b, miR-99a, miR-342-3p, miR-126, miR-888, miR-130a, let-7c, miR-150, miR-296, miR-199a, miR-199a-3p, and miR-302a. In some embodiments, the sample is a tissue sample.

In some embodiments, a profile of differentially expressed miRNAs comprise of one or more (optionally, all) of let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199a-3p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, and miR-98, which is useful in distinguishing IPMN from non-IPMN. If higher expression of one or more (optionally, all) of these miRNA markers is detected relative to the reference expression level, it suggests a precursor legion is present. Optionally, a confirmatory test may be administered, such as imaging. In some embodiments using these miRNAs, the sample is a fluid sample, such as whole blood, serum, plasma, urine, or pancreatic cyst fluid.

In some embodiments, a profile of differentially expressed miRNAs comprise of one or more (optionally, all) of miR-200a-3p, miR-1185-5p, miR-33a-5p, miR-574-3p, and miR-663b, which can distinguish malignant IPMN from benign IPMN. If lower expression of one or more (optionally, all) of these miRNA markers is detected relative to the reference expression level, it suggests the subject has a pancreatic malignancy, and therapeutic treatment should be administered such as a surgical intervention (e.g., resection or Whipple procedure), or administration of an anti-cancer agent (e.g., chemotherapeutic or immunotherapy), or radiation. In some embodiments using these miRNAs, the sample is a fluid sample, such as whole blood, serum, plasma, urine, or pancreatic cyst fluid.

Various samples can be used for practicing the methods of the current invention. Non-limiting examples of the tissues or cell samples that can be used to practice the methods of the current invention include brain, eyes, Pineal gland, Pituitary gland, Thyroid gland, Parathyroid glands, thorax, heart, lungs, esophagus, Thymus gland, pleura, Adrenal glands, Appendix, Gall bladder, urinary bladder, large intestine, small intestine, kidneys, liver, pancrease, spleen, stoma, Prostate gland, Testes, ovaries, or uterus. Also, samples of body fluids of a subject can be used to practice the methods of the current invention. Non-limiting examples of the body fluids that can be used to practice the methods of the current invention include amniotic fluid, aqueous humor, vitreous humor, bile, cerebrospinal fluid, chyle, endolymph, perilymph, female ejaculate, male ejaculate, lymph, mucus (including nasal drainage and phlegm), pericardial fluid, peritoneal fluid, pleural fluid, pus, rheum, saliva, sputum, synovial fluid, vaginal secretion, pancreatic juice or aspirate (20, 47), pancreatic cyst fluid (28), urine, serum, plasma, and blood. In some embodiments, the sample is a blood sample (whole blood, serum, or plasma). In one embodiment, blood cells are used to practice the methods of the current invention. Various processing steps known in the art may be carried out on a sample to obtain genetic material from the blood cells to determine the expression level of one or more miRNAs.

In another embodiment, the miRNAs indicative of pancreatic cancer, or a higher risk of developing pancreatic cancer, are detected in body fluids. In some embodiments, the body fluid is a cell-containing body fluid, such as whole blood. In some embodiments, the body fluid is a cell-free fluid such as plasma. The samples obtained from the subject can be appropriately treated to separate the fraction containing cells from the fraction containing the fluid. Non-limiting examples of such treatment includes filtration, centrifugation, etc. Tissue samples may be fresh frozen or formalin-fixed, paraffin-embedded, for example.

Various body fluids that can be used to practice these methods of the claimed invention include amniotic fluid, aqueous humor, vitreous humor, bile, cerebrospinal fluid, chyle, endolymph, perilymph, female ejaculate, male ejaculate, lymph, mucus (including nasal drainage and phlegm), pericardial fluid, peritoneal fluid, pleural fluid, pus, rheum, saliva, sputum, synovial fluid, vaginal secretion, pancreatic juice or aspirate (20, 47), pancreatic cyst fluid (28), serum, plasma, and blood. In some embodiments, the sample is a blood sample (whole blood, serum, or plasma). In some embodiments, the sample is an acellular body fluid, such as serum or blood plasma.

Certain other embodiments of the current invention provide microarrays of oligonucleotides corresponding to the miRNAs that are differentially expressed in a sample of an individual having pancreatic cancer, or having a high risk of developing pancreatic cancer, particularly, when the individual has a pancreatic lesion. In one embodiment, the cell is a blood cell and accordingly, the current invention also provides a blood-based minimally-invasive miRNA assay that can be used to identify in an individual having a pancreatic lesion the risk of developing pancreatic cancer. As such, the current invention provides microarrays that can be used to differentiate between high-risk pancreatic lesions that warrant resection and low-risk pancreatic lesions that can be monitored. In some embodiments, the microarrays of the current invention comprise oligonucleotides corresponding to one or more of miR-100, miR-99b, miR-99a, miR-342-3p, miR-126, miR-888, miR-130a, let-7c, miR-150, miR-296, miR-199a, miR-199a-3p, and miR-302a, preferably, one or more of miR-100, miR-99b, miR-99a, miR-342-3p, miR-126, and miR-130a.

In some embodiments, the microarrays of the current invention comprise oligonucleotides corresponding to one or more of let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199a-3p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-33'7-5p, miR-340-5p, miR-423-5p, miR-4454, miR-593-3p, and miR-98.

In some embodiments, the microarrays of the current invention comprise oligonucleotides corresponding to one or more of miR-200a-3p, miR-1185-5p, miR-33a-5p, miR-574-3p, and miR-663b.

In some embodiments, the microarrays of the current invention comprise oligonucleotides corresponding to one or more of miR-1185-5p, miR-33a-5p, miR-574-3p, and miR-663b.

Additional embodiments of the current invention provide microarray chips consisting essentially of oligonucleotides corresponding to miRNAs belonging to a profile of differentially expressed miRNAs in a sample of an individual having pancreatic cancer, or having a high risk of developing pancreatic cancer, particularly, when the individual has a pancreatic lesion. For the purposes of this invention, a microarray chip "consisting essentially of" oligonucleotides corresponding to miRNAs belonging to a profile of differentially expressed miRNAs in a sample of an individual having pancreatic cancer, or having a high risk of developing pancreatic cancer, indicates that the microarray chip contains only those miRNAs that are differentially expressed in the sample of an individual having pancreatic cancer, or having high risk of developing pancreatic cancer, and does not contain miRNA whose expression remains unchanged in the sample of an individual having pancreatic cancer, or high risk of developing pancreatic cancer.

In one embodiment of the current invention, a microarray chip consists essentially of oligonucleotides corresponding to one or more of, miR-100, miR-99b, miR-99a, miR-342-3p, miR-126, miR-888, miR-130a, let-7c, miR-150, miR-296, miR-199a, miR-199a-3p, and miR-302a, preferably, one or more of miR-100, miR-99b, miR-99a, miR-342-3p, miR-126, and miR-130a.

Certain embodiments of the current invention provide a method of screening a subject for having high risk of developing pancreatic cancer, the method comprising:

a) obtaining a test cell from the subject,
b) obtaining a reference cell, c) determining the expression of an miRNA in the test cell and the reference cell wherein the miRNA belongs to a profile of differentially expressed miRNAs in a cell of an individual having high risk of developing pancreatic cancer, d) comparing the expression of the miRNA in the test cell with the expression of the miRNA in the reference cell, e) determining the presence of high risk of developing pancreatic cancer in the subject if the miRNA is differentially expressed in the test cell as compared to the reference cell.

In one embodiment, the subject being screened for having high risk of developing pancreatic cancer has a pancreatic lesion and the miRNA belongs to a profile of differentially expressed miRNAs in a cell of an individual having a pancreatic lesion and having high risk of developing pancreatic cancer compared to the corresponding cell of an individual having the pancreatic lesion and having no risk or low risk of developing pancreatic cancer.

The reference sample can be obtained from an individual having no risk or low risk of developing pancreatic cancer. The reference sample can also be obtained from an individual who has a pancreatic lesion and who has no risk or low risk of developing pancreatic cancer. Additionally, the reference sample can be obtained from the subject (and stored for future use) when the subject was known to have no risk or low risk of developing pancreatic cancer, particularly, when the subject had a pancreatic lesion and had no risk or low risk of developing pancreatic cancer. The methods of the current invention can be practiced in a mammal, for example, a human, an ape, a pig, a bovine, a rodent, or a feline.

In some embodiments of the methods of the invention, the subject from which the sample is obtained has pancreatic cancer. In some embodiments of the methods of the invention, the subject from which the sample is obtained does not have pancreatic cancer.

The miRNA that can be tested according to the methods of the current invention can be one or more of miR-100, miR-99b, miR-99a, miR-342-3p, miR-126, miR-888, miR-130a, let-7c, miR-150, miR-296, miR-199a, miR-199a-3p, and miR-302a, preferably, one or more of miR-100, miR-99b, miR-99a, miR-342-3p, miR-126, and miR-130a.

In an embodiment, the method of screening a subject for having pancreatic cancer, or for having a high risk of developing pancreatic cancer comprises determining the expression of a plurality of miRNAs, wherein each miRNA belongs to the profile of differentially expressed miRNAs in a cell of an individual having high risk of developing pancreatic cancer. In one embodiment, the subject being screened for having high risk of developing pancreatic cancer has a pancreatic lesion and the plurality of miRNAs belong to a profile of differentially expressed miRNAs in a cell of an individual having a pancreatic lesion and having high risk of developing pancreatic cancer.

A plurality of miRNAs used in the method of screening a subject for having pancreatic cancer, or having a high risk of developing pancreatic cancer, can be selected from miR-100, miR-99b, miR-99a, miR-342-3p, miR-126, miR-888, miR-130a, let-7c, miR-150, miR-296, miR-199a, miR-199a-3p, and miR-302a, preferably, from miR-100, miR-99b, miR-99a, miR-342-3p, miR-126, and miR-130a.

In other embodiments, the miRNA is one or more of let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199a-3p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, and miR-98.

In other embodiments, the miRNAs are one or more of miR-200a-3p, miR-1185-5p, miR-33a-5p, miR-574-3p, and miR-663b.

In other embodiments, the miRNAs are one or more of miR-1185-5p, miR-33a-5p, miR-574-3p, and miR-663b.

Additional embodiments of the current invention provide kits for performing a barcode-based (e.g., NanoString™ based) assay to quantify expression of miRNAs belonging to a profile of differentially expressed miRNAs in a sample of an individual having pancreatic cancer, or having a high risk of developing pancreatic cancer, particularly, when the individual has a pancreatic lesion. NanoString™ based assays are described in the U.S. Pat. Nos. 8,415,102, 8,519,115, and 7,919,237, which are herein incorporated by reference in their entirety. NanoString's NCOUNTER technology is a variation on the DNA microarray. It uses molecular "barcodes" and microscoping imaging to detect and count up to several hundred unique transcripts in one hybridization reaction. Each color-coded barcode is attached to a single target-specific probe corresponding to a target of interest. The protocol typically includes hybridization (employing two ~50 base probes per mRNA that hybridize in solution; the reporter probe carries the signal, while the capture probe allows the complex to be immobilized for data collection); purification and immobilization (after hybridization, the excess probes are removed and the probe/target complexes are aligned and immobilized in the cartridge); and data collection (sample cartridges are placed in a digital analyzer instrument for data collection; color codes on the surface of the cartridge are counted and tabulated for each target molecule). The protocol is carried out with a prep station, which is an automated fluidic instrument that immobilizes code set complexes for data collection, and a digital analyzer, which derives data by counting fluorescent barcodes. Code set complexes are custom-made or pre-designed sets of color-coded probes pre-mixed with a set of system controls. A person of ordinary skill in the art can determine the sequences of various probes for barcode-based assay to practice the claimed invention and such embodiments are within the purview of the current invention.

In one embodiment of the current invention, the barcode-based assay kit consists essentially of oligonucleotide probes designed to quantify one or more of, miR-100, miR-99b, miR-99a, miR-342-3p, miR-126, miR-888, miR-130a, let-7c, miR-150, miR-296, miR-199a, miR-199a-3p, and miR-302a, preferably, one or more of miR-100, miR-99b, miR-99a, miR-342-3p, miR-126, and miR-130a.

In other embodiments, the miRNA is one or more of let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199a-3p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, and miR-98.

In other embodiments, the miRNAs are one or more of miR-200a-3p, miR-1185-5p, miR-33a-5p, miR-574-3p, and miR-663b.

In other embodiments, the miRNAs are one or more of miR-1185-5p, miR-33a-5p, miR-574-3p, and miR-663b.

For the purposes of this invention, a barcode-based (e.g., NanoString™ based) assay kit "consisting essentially of" oligonucleotide probes designed to quantify miRNAs belonging to a profile of differentially expressed miRNAs in a cell of an individual having pancreatic cancer, or a high risk of developing pancreatic cancer, indicates that the barcode-based assay kit contains oligonucleotide probes corresponding only those miRNAs that are differentially expressed in the sample of an individual having pancreatic cancer, or having a high risk of developing pancreatic cancer, and does not contain oligonucleotide probes corresponding to miRNA whose expression remains unchanged in the sample of an individual having pancreatic cancer, or having a high risk of developing pancreatic cancer.

Additional embodiments of the current invention provide methods of treating and/or preventing pancreatic cancer in a subject identified to be having high risk of developing pancreatic cancer, particularly, when the subject has a pancreatic lesion. The method of treating and/or preventing pancreatic cancer in the subject comprises administering a pharmaceutically effective amount of a pancreatic cancer therapeutic or administering one or more other therapies (for example, radiotherapy, chemotherapy, immunotherapy, another type of anti-cancer agent, surgery, or a combination of two or more of the foregoing), directed at treating and/or preventing pancreatic cancer. As used herein, the term "preventing" encompasses avoiding develop of the cancer, as well as delaying the onset of the cancer. In certain embodiments a combination of two or more therapies directed at treating pancreatic cancer are administered to the subject.

As used herein, the article "a" (such as "a cell") refers to one or more than one.

In one embodiment, the therapy directed at treating and/or preventing pancreatic cancer comprises a surgical resection of the pancreatic lesion from the subject, or a Whipple procedure, or other therapy for pancreatic cancer, such as administration of an anti-cancer agent (e.g., chemotherapeutic or immunotherapy).

Accordingly, the current invention provides a method of treating and/or preventing a pancreatic cancer in a subject, the method comprising:
(a) detecting the level of expression of one or more miRNAs in:
A) a test cell obtained from the subject, and
B) optionally, a control cell,
wherein a differential expression of the one or more miRNAs in the cell sample obtained from the subject as compared to the control cell, or a reference expression level, is indicative of the presence high risk of developing pancreatic cancer in the subject; and
(b) administering a therapy to the mammal to treat the pancreatic cancer,
wherein the one or more miRNAs are differentially expressed in a cell in an individual having high risk of developing pancreatic cancer as compared to the corresponding cell in an individual having low risk of developing pancreatic cancer.

In one embodiment, the subject being screened for having high risk of developing pancreatic cancer has a pancreatic lesion and the miRNA is differentially expressed in a cell of an individual having a pancreatic lesion and having high risk of developing pancreatic cancer compared to the corresponding cell of an individual having a pancreatic lesion and having no risk or low risk of developing pancreatic cancer.

In one embodiment, the cell sample obtained from the subject is a blood cell sample.

In another embodiment, the current invention also provides a method for predicting the existence of a pancreatic cancer in a subject, the method comprising:
a) obtaining a cell sample from the subject,
b) optionally, obtaining a control cell, and
c) detecting and quantifying the expression of one or more miRNAs that are differentially expressed in a cell of an individual having high risk of developing pancreatic cancer as compared to the corresponding cell of an individual having low risk of developing pancreatic cancer, wherein quantifying the expression of the one or more miRNAs is performed by northern blot analysis, micro-array based method, real-time quantitative PCR, or semi-quantitative RT-PCR.

In one embodiment of the method for predicting the existence of a pancreatic cancer in a subject, the subject being screened for having high risk of developing pancreatic cancer has a pancreatic lesion and the miRNA is differentially expressed in a cell of an individual having a pancreatic lesion and having high risk of developing pancreatic cancer compared to the corresponding cell of an individual having a pancreatic lesion and having no risk or low risk of developing pancreatic cancer.

In a further embodiment, the method of detecting the presence of pancreatic cancer, or detecting the high risk of developing pancreatic cancer, can be performed by a computer-assisted analytic device. In the computer assisted method, the computer-assisted analytical device detects the differential expression of miRNAs, determines the amounts of said detected miRNAs, and performs a comparison of the determined amount(s) obtained from the analyzing unit with a reference amount or reference amounts to provide output regarding the presence or absence of high risk of developing pancreatic cancer in the subject, particularly, when the subject has a pancreatic lesion. In certain embodiments, the computer-assisted analytical device detects differentially expressed miRNAs selected from one or more of miR-100, miR-99b, miR-99a, miR-342-3p, miR-126, miR-888, miR-130a, let-7c, miR-150, miR-296, miR-199a, miR-199a-3p, and miR-302a, particularly, one or more of miR-100, miR-99b, miR-99a, miR-342-3p, miR-126, miR-130a and determines the amounts of said detected miRNAs and performs a comparison of the determined amount(s) obtained from the analyzing unit with a reference amount or reference amounts to provide output regarding the presence or absence of high risk of developing pancreatic cancer in the subject.

Exemplified Embodiments

Embodiment 1: A method of treating and/or preventing the development of pancreatic cancer in a subject, the method comprising:
(a) detecting the level of expression of one or more miRNAs in a sample from the subject;
(b) comparing the detected expression level to a reference expression level, wherein a differential expression of the one or more miRNAs in the sample, as compared to the reference expression level, is indicative of the presence of pancreatic cancer, or a higher risk of developing pancreatic cancer, versus the absence of pancreatic cancer, or a lower risk of developing pancreatic cancer, respectively; and
(c) administering a therapy to treat and/or prevent the pancreatic cancer to the subject identified as having the pancreatic cancer, or at a higher risk of developing pancreatic cancer.

Embodiment 2: The method of embodiment 1, wherein a differential expression of the one or more miRNAs in the sample, as compared to the reference expression level, is indicative of a pancreatic cancer precursor (such as intraductal papillary mucinous neoplasm (IPMN)) versus non-IPMN (normal cells).

Embodiment 3: The method of embodiment 1, wherein a differential expression of the one or more miRNAs in the sample, as compared to the reference expression level, is indicative of a malignant intraductal papillary mucinous neoplasm (IPMN) versus a benign IPMN.

Embodiment 4: The method of embodiment 1, wherein the sample is a tissue sample, and wherein the one or more miRNAs belong to a profile of miRNAs that are differentially expressed in a cell of an individual having a higher risk of developing pancreatic cancer as compared to the corresponding cell of an individual having lower risk of developing pancreatic cancer.

Embodiment 5: The method of embodiment 1, wherein the subject has a pancreatic lesion and the one or more miRNAs belong to a profile of differentially expressed miRNAs in a sample of an individual having a pancreatic lesion and having higher risk of developing pancreatic cancer compared to the corresponding sample of an individual having a pancreatic lesion and having lower risk of developing pancreatic cancer.

Embodiment 6: The method of embodiment 1, wherein the sample obtained from the subject is a tissue sample.

Embodiment 7: The method of embodiment 6, wherein the tissue sample is fresh frozen or formalin-fixed, paraffin-embedded prior to said detecting.

Embodiment 8: The method of embodiment 1, wherein the sample obtained from the subject is a fluid sample.

Embodiment 9: The method of embodiment 1, wherein the sample obtained from the subject is whole blood, serum, or plasma.

Embodiment 10: The method of embodiment 1, wherein the pancreatic cancer is pancreatic ductal adenocarcinoma (PDAC).

Embodiment 11: The method of embodiment 3, wherein the pancreatic lesion is intraepithelial neoplasia (PanIN), mucinous cystic neoplasms (MCNs), or intraductal papillary mucinous neoplasms (IPMNs).

Embodiment 12: The method of embodiment 1, wherein the one or more miRNAs are selected from miR-100, miR-99b, miR-99a, miR-342-3p, miR-126, miR-888, miR-130a, let-7c, miR-150, miR-296, miR-199a, miR-199a-3p, and miR-302a.

Embodiment 13: The method of embodiment 12, wherein the sample obtained from the subject is a tissue sample.

Embodiment 14: The method of embodiment 1, wherein the one or more mRNAs are selected from among let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199a-3p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, and miR-98.

Embodiment 15: The method of embodiment 1, wherein the sample obtained from the subject is a plasma sample.

Embodiment 16: The method of embodiment 1, wherein the one or more mRNAs are selected from among miR-200a-3p, miR-1185-5p, miR-33a-5p, miR-574-3p, and miR-663b.

Embodiment 17: The method of embodiment 16, wherein the sample obtained from the subject is a plasma sample.

Embodiment 18: The method of embodiment 1, wherein the one or more mRNAs are selected from among miR-1185-5p, miR-33a-5p, miR-574-3p, and miR-663b.

Embodiment 19: The method of embodiment 1, wherein the sample obtained from the subject is a plasma sample.

Embodiment 20. The method of embodiment 1, wherein said detecting comprises measuring the expression of the one or more miRNAs by barcode-based assay, miRNA microarray analysis (e.g., chip), digital polymerase chain reaction (PCR), real-time PCR, quantitative reverse transcription PCR (qRT-PCR), semi-quantitative PCR, Northern blot, or in situ hybridization.

Embodiment 21: The method of any preceding embodiment, wherein the subject is a human.

Embodiment 22: The method of embodiment 1, wherein the therapy comprises a surgical resection of the pancreatic lesion or Whipple procedure.

Embodiment 23: The method of embodiment 1 or 22, wherein the therapy comprises administration of an anti-cancer agent (e.g., a chemotherapeutic or immunotherapy) to the subject.

Embodiment 24: A method of treating and/or preventing pancreatic cancer in a subject, comprising measuring the level of expression of one or more miRNAs in a sample obtained from the subject; and administering a treatment for the pancreatic cancer, wherein the one or more miRNAs comprise:

(a) one or more mRNAs selected from among miR-100, miR-99b, miR-99a, miR-342-3p, miR-126, miR-888, miR-130a, let-7c, miR-150, miR-296, miR-199a, miR-199a-3p, and miR-302a; or (b) one or more mRNAs selected from among let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199a-3p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-33'7-5p, miR-340-5p, miR-423-5p, miR-4454, miR-593-3p, and miR-98; or (c) one or more mRNAs selected from among miR-200a-3p, miR-1185-5p, miR-33a-5p, miR-574-3p, and miR-663b.

Embodiment 25: The method of embodiment 24, wherein the one or more miRNAs comprise one or more from among miR-1185-5p, miR-33a-5p, miR-574-3p, and miR-663b.

Embodiment 26: The method of embodiment 24, wherein said detecting comprises measuring the expression of the one or more miRNAs by barcode-based assay, miRNA microarray analysis (e.g., chip), digital polymerase chain reaction (PCR), real-time PCR, quantitative reverse transcription PCR (qRT-PCR), semi-quantitative PCR, Northern blot, or in situ hybridization.

Embodiment 27: A microarray chip corresponding to a profile of miRNAs that are differentially expressed in a sample of an individual having pancreatic cancer, or having a high risk of developing pancreatic cancer, as compared to the corresponding sample of an individual having no risk or low risk of developing pancreatic cancer, the microarray chip consisting essentially of oligonucleotides corresponding to one or more of miRNA selected from among miR-100, miR-99b, miR-99a, miR-342-3p, miR-126, miR-888, miR-130a, let-7c, miR-150, miR-296, miR-199a, miR-199a-3p, and miR-302a.

Embodiment 28: The microarray chip of embodiment 27, wherein the oligonucleotides correspond to each of miR-100, miR-99b, miR-99a, miR-342-3p, miR-126, miR-888, miR-130a, let-7c, miR-150, miR-296, miR-199a, miR-199a-3p, and miR-302a.

Embodiment 29: A microarray chip corresponding to a profile of miRNAs that are differentially expressed in a sample of an individual having a pancreatic lesion and having high risk of developing pancreatic cancer compared to the corresponding sample of an individual having the pancreatic lesion and having no risk or low risk of developing pancreatic cancer, the microarray chip consisting essentially of oligonucleotides corresponding to one or more selected from among miR-100, miR-99b, miR-99a, miR-342-3p, miR-126, miR-888, miR-130a, let-7c, miR-150, miR-296, miR-199a, miR-199a-3p, and miR-302a.

Embodiment 30: The microarray chip of embodiment 29, wherein the oligonucleotides correspond to each of miR-100, miR-99b, miR-99a, miR-342-3p, miR-126, miR-888, miR-130a, let-7c, miR-150, miR-296, miR-199a, miR-199a-3p, and miR-302a.

Embodiment 31: A microarray chip corresponding to a profile of miRNAs that are differentially expressed in a sample of an individual having a pancreatic cancer precursor (such as intraductal papillary mucinous neoplasm (IPMN)) as compared to a non-IPMN (normal cells), the microarray chip consisting essentially of oligonucleotides corresponding to one or more of miRNA selected from among one or more miRNA selected from among let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199a-3p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, and miR-98.

Embodiment 32: The microarray chip of embodiment 31, wherein the oligonucleotides correspond to each of let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199a-3p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, and miR-98.

Embodiment 33: A microarray chip corresponding to a profile of miRNAs that are differentially expressed in a sample of an individual having a malignant intraductal papillary mucinous neoplasm (IPMN)) as compared to a benign IPMN, the microarray chip consisting essentially of oligonucleotides corresponding to one or more of miRNA selected from among one or more miRNA selected from among miR-200a-3p, miR-1185-5p, miR-33a-5p, miR-5'74-3p, and miR-663b.

Embodiment 34: The microarray chip of embodiment 33, wherein the oligonucleotides correspond to each of miR-200a-3p, miR-1185-5p, miR-33a-5p, miR-574-3p, and miR-663b.

Embodiment 35: The microarray chip of embodiment 33, wherein the one or more miRNAs comprise one or more from among miR-1185-5p, miR-33a-5p, miR-574-3p, and miR-663b.

Embodiment 36: The microarray chip of embodiment 33, wherein the oligonucleotides correspond to each of miR-1185-5p, miR-33a-5p, miR-574-3p, and miR-663b.

Embodiment 37: A method for detecting in a subject the presence of pancreatic cancer, or a high risk of developing pancreatic cancer, the method comprising:
(a) detecting the level of expression of one or more miRNAs in a sample from the subject; and
(b) comparing the detected expression level to a reference expression level, wherein a differential expression of the one or more miRNAs in the sample, as compared to the reference expression level, is indicative of the presence of pancreatic cancer, or a higher risk of developing pancreatic cancer, versus the absence of pancreatic cancer, or a lower risk of developing pancreatic cancer, respectively.

Embodiment 38: The method of embodiment 37, wherein a differential expression of the one or more miRNAs in the sample, as compared to the reference expression level, is indicative of a pancreatic cancer precursor (such as intraductal papillary mucinous neoplasm (IPMN)) versus non-IPMN (normal cells).

Embodiment 39: The method of embodiment 37, wherein a differential expression of the one or more miRNAs in the sample, as compared to the reference expression level, is indicative of a malignant intraductal papillary mucinous neoplasm (IPMN) versus a benign IPMN.

Embodiment 40: The method of embodiment 37, wherein the sample is a tissue sample, and wherein the one or more miRNAs belong to a profile of miRNAs that are differentially expressed in a cell of an individual having a higher risk of developing pancreatic cancer as compared to the corresponding cell of an individual having lower risk of developing pancreatic cancer.

Embodiment 41: The method of embodiment 37, wherein the subject has a pancreatic lesion and the one or more miRNAs belong to a profile of differentially expressed miRNAs in a sample of an individual having a pancreatic lesion and having higher risk of developing pancreatic cancer compared to the corresponding sample of an individual having a pancreatic lesion and having lower risk of developing pancreatic cancer.

Embodiment 42: The method of embodiment 37, wherein the sample obtained from the subject is a tissue sample.

Embodiment 43: The method of embodiment 42, wherein the tissue sample is fresh frozen or formalin-fixed, paraffin-embedded prior to said detecting.

Embodiment 44: The method of embodiment 37, wherein the sample obtained from the subject is a fluid sample.

Embodiment 45: The method of embodiment 44, wherein the fluid sample obtained from the subject is whole blood, serum, plasma, urine, or pancreatic cyst fluid.

Embodiment 46: The method of embodiment 37, wherein the pancreatic cancer is pancreatic ductal adenocarcinoma (PDAC).

Embodiment 47: The method of embodiment 41, wherein the pancreatic lesion is intraepithelial neoplasia (PanIN), mucinous cystic neoplasms (MCNs), or intraductal papillary mucinous neoplasms (IPMNs).

Embodiment 48: The method of embodiment 37, wherein the one or more miRNAs are selected from miR-100, miR-99b, miR-99a, miR-342-3p, miR-126, miR-888, miR-130a, let-7c, miR-150, miR-296, miR-199a, miR-199a-3p, and miR-302a.

Embodiment 49: The method of embodiment 37, wherein the one or more miRNAs are each of miR-100, miR-99b, miR-99a, miR-342-3p, miR-126, miR-888, miR-130a, let-7c, miR-150, miR-296, miR-199a, miR-199a-3p, and miR-302a.

Embodiment 50: The method of embodiment 37, wherein the sample obtained from the subject is a tissue sample.

Embodiment 51: The method of embodiment 37, wherein the one or more mRNAs are selected from among let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199a-3p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, and miR-98.

Embodiment 52: The method of embodiment 37, wherein the one or more mRNAs are each of let-7a-5p, let-7d-5p, let-7f-5p, let-7g-5p, let-7i-5p, miR-107, miR-1260b, miR- 126-3p, miR-142-3p, miR-145-5p, miR-146a-5p, miR-148a-3p, miR-15b-5p, miR-181a-5p, miR-191-5p, miR-199a-3p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, and miR-98.

Embodiment 53: The method of embodiment 51 or 52, wherein the sample obtained from the subject is a plasma sample.

Embodiment 54: The method of embodiment 37, wherein the one or more mRNAs are selected from among miR-200a-3p, miR-1185-5p, miR-33a-5p, miR-574-3p, and miR-663b.

Embodiment 55: The method of embodiment 37, wherein the one or more mRNAs are each of miR-200a-3p, miR-1185-5p, miR-33a-5p, miR-574-3p, and miR-663b.

Embodiment 56: The method of embodiment 54 or 55, wherein the sample obtained from the subject is a plasma sample.

Embodiment 57: The method of embodiment 37, wherein the one or more mRNAs are selected from among miR-1185-5p, miR-33a-5p, miR-574-3p, and miR-663b.

Embodiment 58: The method of embodiment 37, wherein the one or more mRNAs are each of miR-1185-5p, miR-33a-5p, miR-574-3p, and miR-663b.

Embodiment 59: The method of embodiment 57 or 58, wherein the sample obtained from the subject is a plasma sample.

Embodiment 60: The method of embodiment 37, wherein said detecting comprises measuring the expression of the one or more miRNAs by barcode-based assay, miRNA microarray analysis (e.g., chip), digital polymerase chain reaction (PCR), real-time PCR, quantitative reverse transcription PCR (qRT-PCR), semi-quantitative PCR, Northern blot, or in situ hybridization.

Embodiment 61: The method of embodiment 37, wherein the subject is a human.

Embodiment 62: The method of embodiment 61, further comprising administering to the subject a therapy directed at preventing or treating pancreatic cancer.

Embodiment 63: The method of embodiment 62, wherein the therapy comprises surgical resection or pancreatoduodenectomy (Whipple procedure).

Embodiment 64: The method of embodiment 62 or 63, wherein the therapy comprises administration of an anti-cancer agent (e.g., a chemotherapeutic or immunotherapy) to the subject.

Embodiment 65: The method of embodiment 37, wherein the reference expression level is that of:
a. an organism belonging to the same species as the subject having no risk or a low risk of developing pancreatic cancer,
b. the subject when the subject had no risk or low risk of developing pancreatic cancer, or
c. an organism belonging to the same species as the subject having the pancreatic lesion and having no risk or low risk of developing pancreatic cancer.

Embodiment 66: A kit for performing a barcode-based assay to quantify expression of miRNAs belonging to a profile of differentially expressed miRNAs in a sample of an individual having high risk of developing pancreatic cancer, comprising vials containing different oligonucleotide probes designed to quantify one or more miRNAs in a sample, wherein the differential expression of the one or more miRNAs, as compared to the reference expression level, is indicative of a higher risk of developing pancreatic cancer versus a lower risk of developing pancreatic cancer.

Embodiment 67: The kit of embodiment 66, wherein the barcode-based assay kit consists essentially of oligonucleotide probes designed to quantify one or more of miR-100, miR-99b, miR-99a, miR-342-3p, miR-126, miR-888, miR-130a, let-7c, miR-150, miR-296, miR-199a, miR-199a-3p, and miR-302a, preferably, one or more of miR-100, miR-99b, miR-99a, miR-342-3p, miR-126, and miR-130a.

Embodiment 68: The kit of embodiment 66, wherein the barcode-based assay kit consists essentially of oligonucleotide probes designed to quantify each of miR-100, miR-99b, miR-99a, miR-342-3p, miR-126, miR-888, miR-130a, let-7c, miR-150, miR-296, miR-199a, miR-199a-3p, and miR-302a.

Embodiment 69: The kit of embodiment 66, wherein the barcode-based assay kit consists essentially of oligonucleotide probes designed to quantify one or more of let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199a-3p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, and miR-98.

Embodiment 70: The kit of embodiment 66, wherein the barcode-based assay kit consists essentially of oligonucleotide probes designed to quantify each of let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199a-3p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-33'7-5p, miR-340-5p, miR-423-5p, miR-4454, miR-593-3p, and miR-98.

Embodiment 71: The kit of embodiment 66, wherein the barcode-based assay kit consists essentially of oligonucleotide probes designed to quantify one or more of miR-200a-3p, miR-1185-5p, miR-33a-5p, miR-574-3p, and miR-663b.

Embodiment 72: The kit of embodiment 66, wherein the barcode-based assay kit consists essentially of oligonucleotide probes designed to quantify each of miR-200a-3p, miR-1185-5p, miR-33a-5p, miR-574-3p, and miR-663b.

Embodiment 73: The kit of embodiment 66, wherein the barcode-based assay kit consists essentially of oligonucleotide probes designed to quantify one or more of miR-1185-5p, miR-33a-5p, miR-574-3p, and miR-663b.

Embodiment 74: The kit of embodiment 66, wherein the barcode-based assay kit consists essentially of oligonucleotide probes designed to quantify each of miR-1185-5p, miR-33a-5p, miR-574-3p, and miR-663b.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Examples of certain embodiments of the invention include, but are not limited to:

Materials and Methods for Example 1

Study population and biospecimens. A prospectively maintained clinical database was retrospectively reviewed to identify individuals who underwent pancreatic resection for an IPMN between 1999 and 2011 at Moffitt Cancer Center and Research Institute (Moffitt) and had donated tissue for research through protocols approved by the Institutional Review Board (IRB) of the University of South Florida. A pathologist with expertise in PDAC and IPMN pathology (DC) used hematoxylin and eosin (H&E) stained slides from selected blocks to histologically confirm the diagnosis and degree of dysplasia using World Health Organization (WHO) guidelines (22), and consulted with another pancreatic pathologist (BC) as needed. The final diagnosis represented the most severe grade of dysplasia observed in the neoplastic epithelium of each resected lesion, and multiple representative areas of the corresponding grade were electronically marked on the H&Es. Examples of grades of IPMN dysplasia are shown in FIGS. 4A-4D.

Laser capture microdissection (LCM) and RNA isolation. Under RNAse-free conditions, four 8-micron sections were cut from the FFPE block corresponding to each respective H&E. Sections were placed in a water bath, mounted on uncharged and uncoated glass slides, air-dried overnight, and transferred to Moffitt's Analytic Microscopy Core for LCM. Sections were deparaffinized, hydrated, and stained using nuclease-free Histogene solution (Applied Biosystems (ABI), Austin, Tex.), dehydrated, and then air-dried before placement in an Autopix LCM instrument (Arcturus, Molecular Devices, Sunnyvale, Calif.). Locations of dysplasia were verified using the marked electronic images. Cells of interest were captured from each section using Macro LCM Caps (Arcturus CapSure, #09F10A). Caps of cells from each case were pooled and 50 µL of lysis buffer was added to stop RNA degradation. Qiagen's miRNeasy™ FFPE Isolation Kit was used for total RNA isolation, which included isolation of small non-coding RNAs, according to the manufacturer's procedures. RNA quantity and quality was assessed by Optical Density (OD) at 260 and 280 nm using a Nanodrop spectrophotometer. When RNA quantity was insufficient, additional tissue sections were processed. If RNA quality was poor, an ethanol precipitation was performed.

High throughput miRNA expression analysis. Genome-wide miRNA profiling was conducted using Taqman® MicroRNA Arrays, also known as Taqman Low Density Array (TLDA) 'Pool A' Card version 3.0. This 384-microfluidic array was designed to perform quantitative reverse transcriptase (qRTPCR) reactions simultaneously (Applied Biosystems, Austin, Tex., USA) on 378 mature miRNAs and 6 endogenous controls. Using 20 nanograms (ng) of total RNA as input, cDNA was synthesized with multiplexed Megaplex™ RT primers, preamplified with Megaplex™ PreAmp Primers, and mixed with TaqMan Universal PCR Master Mix (Applied Biosystems). Samples were loaded onto TLDA cards for expression analysis.

Individual qRT-PCR validation of miRNA candidates. The most deregulated miRNAs were evaluated in an independent set of 21 IPMNs (13 high-risk and 8 low-risk) as part of a replication phase. Total RNA was isolated from microdissected cells, and singleplex qRT-PCR assays were performed using 10 ng total RNA per reaction using pre-designed Taqman® MicroRNA Assays (Applied Biosystems, Foster City, Calif.). The expression level of the most stable and abundantly expressed endogenous control was used for normalization. All assays were carried out in triplicate to ensure reproducibility. Positive and negative control (nuclease free water) samples were used to evaluate reagent performance and contamination. PCR was run on the 7900HT instrument according to the manufacturer's instructions. For each sample, the threshold cycle (Ct) was calculated by the ABI Sequence Detection software v2.3.

Statistical Analyses. Descriptive statistics were determined using frequencies and percent for categorical variables and means and standard deviations (SD) for continuous variables. The distributions of covariates were compared across the low- versus high-risk IPMN groups using t-tests for continuous variables and Chi-squared or Fisher's exact tests for categorical variables, as appropriate. Relative miRNA expression levels were calculated using a method similar to the comparative Ct ($2-\Delta\Delta CT$) method. Briefly, $\Delta CT$ was calculated for each miRNA so that each miRNA was first normalized to the most stably expressed endogenous control, RNU44 (i.e. $\Delta CT=CT-RNU44$). Normalized CT values were further calculated as $\log_2[Max(\Delta CT)-\Delta CT]$.

Nonparametric tests (Wilcoxon rank sum tests) were performed to compare the normalized expression levels between groups for each miRNA. False discovery rates (FDR) adjusting for multiple comparisons were estimated using q-values. Correlations between expression of the most deregulated miRNAs and selected clinical and pathological factors were examined using Pearson correlations for continuous variables and ANOVA and logistic regression for categorical variables. Multivariable regression analysis was conducted to identify miRNAs associated with high-risk IPMN status independent of selected variables. To assess the accuracy and clinical utility of candidate miRNAs in differentiating between high-risk and low-risk IPMNs, receiver operating characteristic (ROC) curves were constructed using $\Delta CT$ values, with pathological diagnosis as the gold standard. Logistic regression models predicting risk status were fit using values from the discovery dataset, and ROC curves were used to predict low versus high-risk IPMN status in the replication dataset. p-value of <0.05 was used as the threshold for statistically significance in most analyses. All statistical analyses were performed using Matlab version 2009b and R version 2.13.1. To visualize miRNA expression patterns, we generated heatmaps and performed unsupervised, hierarchical clustering using Matlab.

Bioinformatics Analyses. To gain insight into mechanisms responsible for miRNA-mediated progression to pancreatic malignancy, publicly-available tools were used to identify genes and pathways controlled by the candidate miRNAs. We first determined experimentally-verified miRNA targets of the most deregulated miRNAs using the miRecords and TarBase databases and published literature. Using identified mRNAs as candidates, a pathway enrichment analysis was conducted using Gene Ontology's MetaCore database (see world wide website genego.com). Pathways related to PDAC and interaction hubs (genes with more than 5 interactions) were identified and overlapped with experimentally-verified targets to narrow down the number of biologically important genes.

Microarray gene expression analysis of IPMNs. Under an IRB-approved protocol, fresh-frozen tumor tissue from patients treated at Moffitt was previously arrayed on Affymetrix HuRSTA-2a520709 GeneChips (Affymetrix, Santa Clara, Calif.) which contained ~60,000 probe sets representing ~25,037 unique genes (Affymetrix HuRSTA-2a520709, GEO: see world wide website: ncbi.nlm.nih.gov/geo/query/acc.cgi?acc=GPL10379). Of 14,492 distinct solid tumors that were arrayed, twenty-three represented surgically-resected, pathologically-confirmed IPMNs (17 invasive and 6 non-invasive (1 LG, 1 MG, 4 HG)). For the 23 IPMNs that were arrayed, expression data for 21 candidate targets of interest (66 probe-sets) highlighted by bioinformatics analysis were normalized using Robust Multi-array Average (RMA) and then extracted. Due to small cell counts, the high-risk group represented all invasive IPMNs and was compared to a low-risk group that included all non-invasive IPMNs.

Nonparametric tests (rank sum tests) were used to compare expression between groups for each target gene. FDRs were estimated using q-values. Of the 23 IPMN cases with microarray data, 8 were evaluated as part of the current miRNA discovery (n=2; 1 LG, 1 HG) or replication phase (n=6; 1 MG, 3 HG, 2 invasive), which enabled preliminarily exploration of relationships between miRNA and target mRNA expression for paired samples using Pearson correlations.

Example 1—Identification of Tissue Mirnas Differentially Expressed in Subjects Having Pancreatic Cancer or Having High Risk of Developing Pancreatic Cancer A. Study Population Forty-nine IPMN cases contributed tissue for the discovery (n=28; 19 high-risk (all HG) and 9 low-risk (all LG)) or replication phase (n=21; 13 high-risk (11 HG, 2 invasive) and 8 low risk (4 LG and 4 MG)). Select clinical and pathologic characteristics of patients with IPMNs in the discovery phase (N=28) is shown in Table 1A and clinical and pathologic characteristics of the patients in discovery and replication phase (17 low-risk and 32 high-risk IPMN participants) are shown in Table 1B. Overall, characteristics were not significantly different between the high- and low-risk groups (Table 1B). Age at diagnosis was slightly older in individuals with high-risk IPMNs (69.1 years) compared to those with low-risk IPMNs (65.1 years). The predominant tumor location for 59% of the high-risk IPMNs was the pancreatic head, whereas most (65%) low-risk IPMNs occurred in the pancreatic body or tail. On endoscopic ultrasound (EUS), signs of malignant potential were observed more frequently among high-risk (72%) compared to low-risk IPMNs (47%) (P=0.09). Only 40% of high-risk IPMNs were observed to be >3 cm on EUS. High-risk IPMNs were significantly more likely to involve the main pancreatic duct upon pathological review compared to low-risk IPMNs (p=0.0007). The distribution of characteristics was similar among cases in each phase.

TABLE 1A

Select Clinical and Pathologic Characteristics of Patients with IPMNs (N = 28) in discovery phase.

| | Low-grade (n = 9) | High-grade (n = 19) | All IPMNs (N = 28) |
|---|---|---|---|
| Age at diagnosis, mean (yrs) | 66.4 | 68.4 | 67.8 |
| Gender | | | |
| Male | 5 (56) | 10 (53) | 15 (54) |
| Race | | | |
| White, Non-Hispanic | 8 (89) | 18 (95) | 26 (93) |
| Predominant tumor location in pancreas | | | |
| Head | 4 (44) | 14 (74) | 18 (64) |
| Body or Tail | 5 (56) | 5 (26) | 10 (36) |
| Signs of malignant potential[1] on EUS | 5 (56) | 15 (79) | 20 (71) |

TABLE 1A-continued

Select Clinical and Pathologic Characteristics of Patients with IPMNs (N = 28) in discovery phase.

| | Low-grade (n = 9) | High-grade (n = 19) | All IPMNs (N = 28) |
|---|---|---|---|
| Pancreatic duct involvement[2] | | | |
| Main duct | 1 (11) | 7 (37) | 8 (29) |
| Side branch duct | 4 (44) | 2 (11) | 6 (21) |
| Mixed | 3 (33) | 9 (47) | 12 (43) |
| Size of largest cyst | | | |
| <3 cm. | 7 (78) | 10 (53) | 17 (61) |
| >3 cm. | 2 (22) | 9 (47) | 11 (39) |
| Size of largest cyst[2], mean (SD) (cm) | 2.3 (1.5) | 2.7 (1.3) | 2.4 (1.1) |
| Asymptomatic | | | |
| Yes | 2 (22) | 2 (11) | 4 (14) |
| No | 7 (78) | 17 (89) | 24 (86) |
| Ever Smoker | | | |
| Yes | 8 (89) | 11 (58) | 19 (68) |
| No | 1 (11) | 8 (42) | 9 (32) |

Data represent counts (percentages) unless otherwise indicated. Counts may not add up to the total due to missing values, and percentages may not equal 100 due to rounding.
[1]Signs of malignant potential on endoscopic ultrasound (EUS) included main duct involvement, main duct dilation (>6 mm), presence of mural nodules, septation, wall thickness, or cyst size >3 cm.
[2]Based on pathology report.

TABLE 1B

Clinical and Pathologic Characteristics of Patients with IPMNs (N = 49) in discovery and replication phase.

| Variable | Low-risk[1] IPMNs (n = 17) | High-risk[2] IPMNs (n = 32) | P-value[3] |
|---|---|---|---|
| Age at diagnosis, mean (SD)(yrs) | 65.1 (9.6) | 69.1 (9.7) | 0.18 |
| Gender | | | |
| Male | 11 (65) | 18 (56) | 0.57 |
| Female | 6 (35) | 14 (44) | |
| Race | | | |
| White, Non-Hispanic | 15 (88) | 29 (91) | 0.79 |
| Other | 2 (12) | 3 (9) | |
| Year of Surgery | | | |
| 1999-2005 | 1 (6) | 5 (16) | 0.32 |
| 2006-2011 | 16 (94) | 27 (84) | |
| Predominant tumor location | | | |
| Pancreatic Head | 6 (35) | 19 (59) | 0.11 |
| Pancreatic Body or Tail | 11 (65) | 13 (41) | |
| Signs of malignant potential [4] on EUS | 8 (47) | 23 (72) | 0.09 |
| Size of largest cyst on EUS [4] | | | |
| <3 cm. | 14 (82) | 18 (60) | 0.11 |
| ≥3 cm. | 3 (18) | 12 (40) | |
| Size of largest cyst [4], mean (SD) (cm) | 2.0 (1.2) | 2.5 (1.3) | 0.21 |
| Pancreatic duct involvement [5] | | | |
| Main duct or mixed | 5 (29) | 25 (78) | $7 \times 10^{-4}$ |
| Side branch duct | 9 (53) | 4 (13) | |
| Asymptomatic | | | |
| Yes | 3 (18) | 4 (13) | 0.62 |
| No | 14 (82) | 28 (88) | |

TABLE 1B-continued

Clinical and Pathologic Characteristics of Patients with IPMNs (N = 49) in discovery and replication phase.

| Variable | Low-risk[1] IPMNs (n = 17) | High-risk[2] IPMNs (n = 32) | P-value[3] |
|---|---|---|---|
| Personal history of chronic pancreatitis | | | |
| Yes | 6 (35) | 16 (50) | 0.32 |
| No | 11 (65) | 16 (50) | |
| Family history of pancreatic cancer | | | |
| Yes | 1 (6) | 2 (6) | 0.97 |
| No | 15 (88) | 29 (91) | |
| Ever Smoker | | | |
| Yes | 11 (65) | 20 (63) | 0.88 |
| No | 6 (35) | 12 (38) | |

Data represent counts (percentages) unless otherwise indicated. Counts may not add up to the total due to missing values, and percentages may not equal 100 due to rounding.
[1] Low-risk IPMNs are represented by 12 low-grade and 5 moderate-grade IPMNs.
[2] High-risk IPMNs are represented by 30 high-grade and 2 invasive IPMNs.
[3] P-value for differences between low- and high-risk groups using chi-squared or Fisher's exact tests and t-tests for categorical and continuous variables, respectively. Values in bold are statistically significant (P < 0.05).
[4] Signs of malignant potential on endoscopic ultrasound (EUS) include main duct (MD) involvement, MD dilation (>5 mm), mural nodules, septation, wall thickness, or cyst size >3 cm.
[5] Based on pathological review post-resection.

B. Biospecimen Quality

Surgically-resected tissue was pathologically evaluated for 58 unique IPMNs. Tissue was not profiled for 6 cases due to an inconclusive grade of dysplasia (n=1), sparse regions of dysplasia (n=2), or technical issues during LCM (n=3). Representative examples of pre- and post-microdissection images of low- and high-grade IPMNs are shown in FIGS. 1A and 1B, respectively. The average total number of cells captured per case was 8,498 (range: 780-65,956), and the average total RNA recovery was 139 ng (range: 48-591 ng). The quality of RNA was appropriate for most cases as evidenced by optical density 260/280 readings in the range of 1.8-2.0. Sub-optimal RNA quantity or quality was observed for 3 cases, leaving 49 cases with adequate tissue for miRNA expression analyses.

C. miRNA Expression Analysis in the Discovery and Replication Phase

Figure 2A:
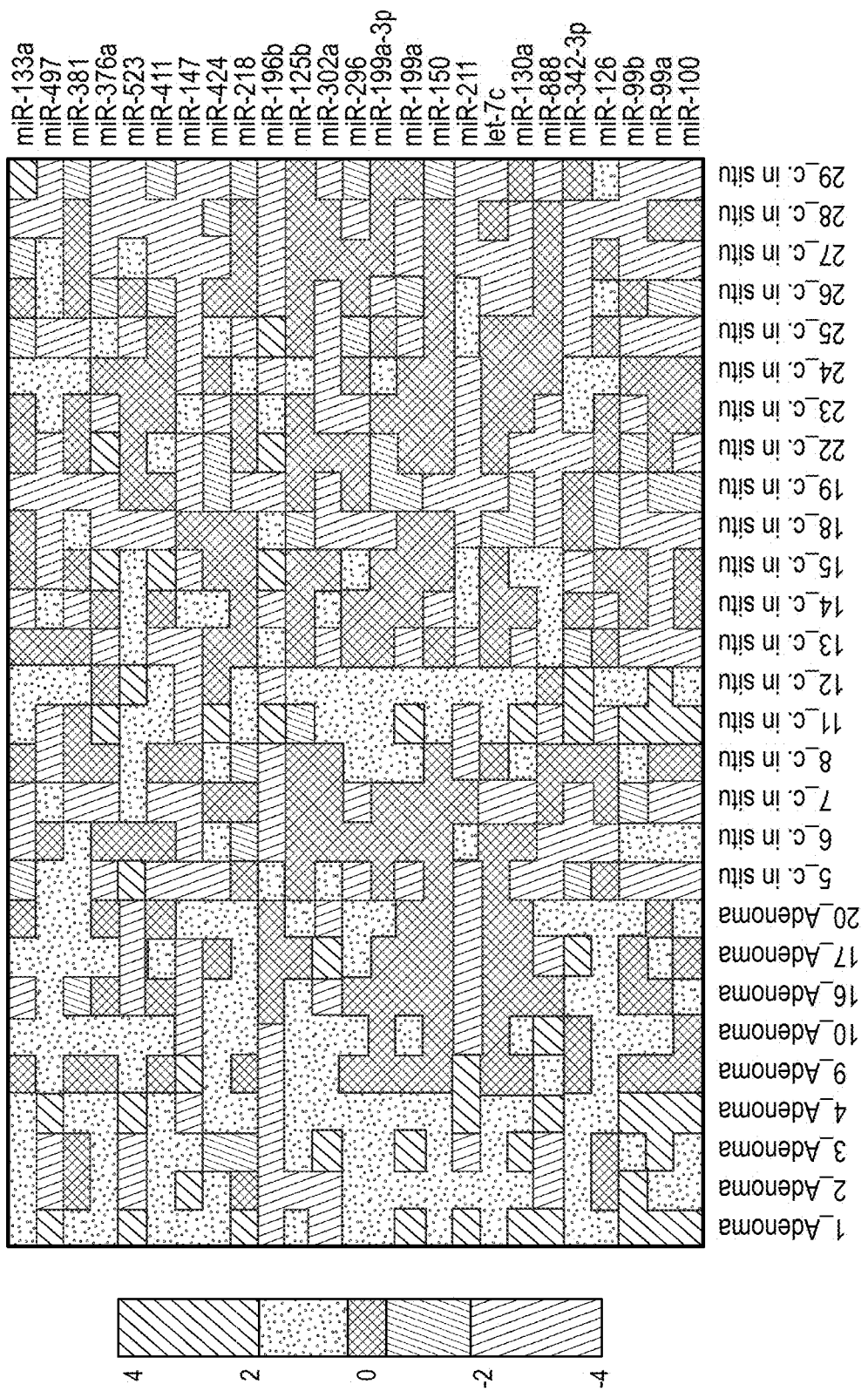
FIGS. 2A and 2B. Heatmap and unsupervised hierarchical clustering of low-risk (adenoma) and high-risk (carcinoma-in-situ) IPMN samples according to the expression of the most differentially expressed miRNAs.

In the discovery phase, 236 of 378 miRNAs evaluated (62.4%) were detectable in at least half of the 28 samples evaluated and were included in subsequent analyses. This percentage is comparable to other studies (28). Thirty-five miRNA probes were significantly deregulated in high-risk compared to low-risk IPMNs (rank sum P<0.05, Table 2). The top deregulated miRNAs separated most low-risk from high-risk IPMNs as shown in the heatmap (FIG. 2A), though outliers existed, consistent with other studies (29). Several outliers may be explained by focal areas of dysplasia available for sampling and/or inter-sample heterogeneity.

TABLE 2

The top 35 most differentially expressed miRNAs between high-risk (N = 19) and low-risk IPMNs (N = 9).

| miRNA probe | mean fold-change | median fold-change | P-value rank-sum test | False discovery rate | N[a] High-risk | N[a] Low-risk |
|---|---|---|---|---|---|---|
| hsa-miR-100-000437 | 4.90 | 5.86 | 0.0016 | 0.0929 | 19 | 9 |
| hsa-miR-99a-000435 | 4.66 | 4.77 | 0.0027 | 0.0929 | 19 | 9 |
| hsa-miR-99b-000436 | 3.75 | 4.74 | 0.0027 | 0.0929 | 19 | 9 |
| hsa-miR-126-002228 | 6.73 | 3.09 | 0.0037 | 0.0929 | 19 | 9 |
| hsa-miR-342-3p-002260 | 3.34 | 4.85 | 0.0037 | 0.0929 | 19 | 9 |
| hsa-miR-888-002212 | 69.52 | 63.47 | 0.0057 | 0.0929 | 14 | 6 |
| hsa-miR-130a-000454 | 5.01 | 4.72 | 0.0059 | 0.0929 | 19 | 9 |
| hsa-let-7c-000379 | 3.59 | 2.66 | 0.0059 | 0.0929 | 18 | 9 |
| hsa-miR-150-000473 | 3.49 | 2.78 | 0.0081 | 0.0929 | 18 | 9 |
| hsa-miR-199a-000498 | 4.42 | 3.14 | 0.0081 | 0.0929 | 18 | 9 |
| hsa-miR-199a-3p-002304 | 3.77 | 4.78 | 0.0081 | 0.0929 | 18 | 9 |
| hsa-miR-296-000527 | 3.69 | 5.29 | 0.0081 | 0.0929 | 18 | 9 |
| hsa-miR-302a-000529 | 36.30 | 6.42 | 0.0094 | 0.0995 | 12 | 5 |
| hsa-miR-125b-000449 | 4.59 | 5.14 | 0.0113 | 0.1114 | 17 | 9 |
| hsa-miR-218-000521 | 6.84 | 7.56 | 0.0131 | 0.1208 | 16 | 8 |
| hsa-miR-424-000604 | 3.72 | 2.51 | 0.0156 | 0.1343 | 16 | 8 |
| hsa-miR-411-001610 | 3.70 | 4.31 | 0.0168 | 0.1361 | 18 | 9 |
| hsa-miR-523-002386 | 5.09 | 3.15 | 0.0196 | 0.1503 | 15 | 4 |
| hsa-miR-376a-000565 | 3.41 | 6.76 | 0.0208 | 0.1509 | 19 | 9 |
| hsa-miR-381-000571 | 4.35 | 6.96 | 0.0240 | 0.1535 | 19 | 8 |
| hsa-miR-494-002365 | 3.57 | 3.36 | 0.0268 | 0.1535 | 11 | 7 |
| hsa-miR-133a-002246 | 4.66 | 8.79 | 0.0269 | 0.1535 | 19 | 9 |
| hsa-miR-139-5p-002289 | 3.37 | 4.63 | 0.0269 | 0.1535 | 19 | 9 |
| hsa-miR-149-002255 | 8.29 | 12.69 | 0.0276 | 0.1535 | 11 | 9 |
| hsa-miR-146b-3p-002361 | 11.48 | 22.42 | 0.0280 | 0.1535 | 10 | 5 |
| hsa-miR-193a-5p-002281 | 2.25 | 1.85 | 0.0289 | 0.1535 | 17 | 8 |
| hsa-miR-410-001274 | 3.12 | 3.98 | 0.0311 | 0.1589 | 17 | 9 |
| hsa-miR-214-002306 | 3.96 | 5.68 | 0.0338 | 0.1637 | 16 | 9 |
| hsa-miR-152-000475 | 2.15 | 3.12 | 0.0344 | 0.1637 | 19 | 9 |
| hsa-miR-142-3p-000464 | 4.25 | 3.31 | 0.0368 | 0.1693 | 18 | 7 |
| hsa-miR-30c-000419 | 2.73 | 3.27 | 0.0388 | 0.1728 | 19 | 9 |
| mmu-miR-153-001191 | 0.09 | 0.05 | 0.0415 | 0.1789 | 12 | 6 |
| hsa-miR-502-001109 | 4.63 | 7.01 | 0.0490 | 0.1936 | 15 | 8 |
| hsa-miR-138-002284 | 3.70 | 3.96 | 0.0491 | 0.1936 | 19 | 9 |
| hsa-miR-204-000508 | 6.44 | 9.55 | 0.0491 | 0.1936 | 19 | 9 |

[a] Number of IPMNs in which the miRNA was detectable.

Figure 2B:
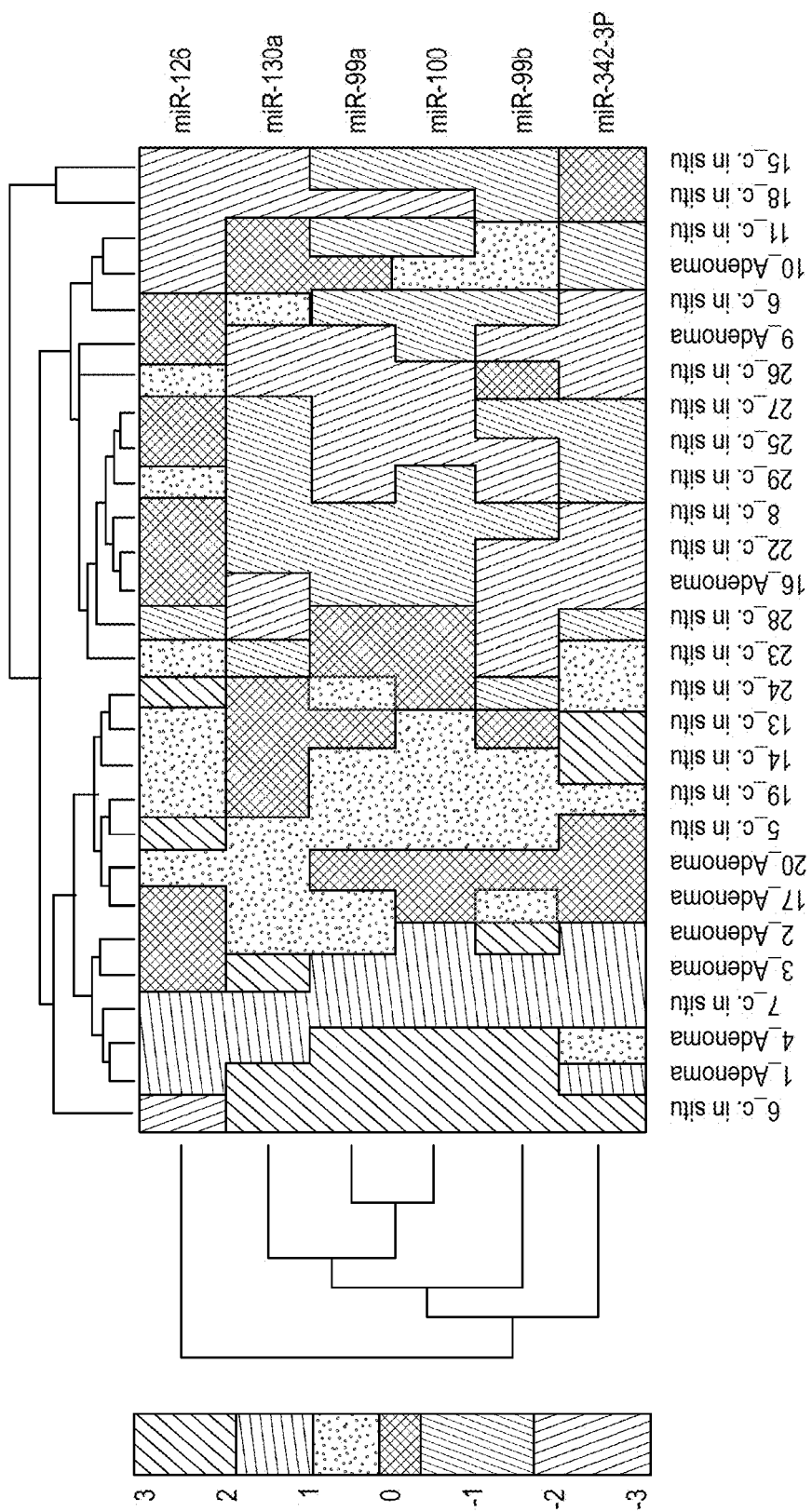

Using a FDR of 10%, 13 of the 35 miRNAs (miR-100, miR-99b, miR-99a, miR-342-3p, miR-126, miR-888, miR-130a, let-7c, miR-150, miR-296, miR-199a, miR-199a-3p, and miR-302a) were significantly deregulated between the groups (Table 2). Of these 13 miRNAs, the top 6 (miR-100, miR-99b, miR-99a, miR-342-3p, miR-126, miR-130a) were selected for further evaluation based on their statistical significance, evidence to support their biological role in pancreatic carcinogenesis, and the fact that they were detectable in all evaluated samples. Expression levels of each of these 6 miRNAs were down-regulated in most high- versus low-risk IPMNs (Table 3). Unsupervised hierarchical clustering analysis also illustrated reduced expression for these 6 miRNAs in the high-risk compared to the low-risk group (FIG. 2B). Experimentally-validated gene targets of the 6 miRNAs are listed in Table 3, and include well-known oncogenes.

TABLE 3

Select candidate miRNAs differentially expressed in high- (N = 19) vs. low-risk (N = 9) IPMN tissue.

| miRNA | P-value[1] | Median Fold change[2] | Mean Fold change[2] | Experimentally validated gene target(s)[3] |
|---|---|---|---|---|
| miR-100 | $1.6 \times 10^{-3}$ | 5.9 | 4.9 | ATM, FGFR3, IGF1R, MMP13, mTOR, PLK1, RPTOR |
| miR-99b | $2.7 \times 10^{-3}$ | 4.7 | 3.7 | RAVER2 |
| miR-99a | $2.7 \times 10^{-3}$ | 4.8 | 4.7 | AGO2, COX2, FGFR3, IGF1R, MEF2D, mTOR, RAVER2, RPTOR, SERPINE1, SKI, TRIB1 |
| miR-342-3p | $3.7 \times 10^{-3}$ | 4.8 | 3.3 | BMP7, DNMT1, GEMIN4 |
| miR-126 | $3.7 \times 10^{-3}$ | 3.1 | 6.7 | ADAM9, CCNE2, CRH, CRK, CRKL, DNMT1, EGFL7, KRAS, HOXA9, IRS1, PGF, PIK3R2, PLK2, PTPN7, RGS3, SLC45A3, SOX2, SPRED1, TOM1, TWF2, VCAM1, VEGFA |
| miR-130a | $5.9 \times 10^{-3}$ | 4.7 | 5.0 | APP, ATG2B, ATXN1, CSF1, DICER1, ESR1, HOXA10, HOXA5, KLF4, MAFB, MEOX2, PPARG, RUNX3, TAC1, TP53INP1 |

[1]Wilcoxon rank-sum test.
[2]All fold-changes represent decreased expression in the high-risk group (all high-grade IPMNs) versus the low-risk group (all low-grade IPMNs).
[3]According to data in Tarbase (diana.cslab.ece.ntua.gr/tarbase/), miRecords (mirecords-.biolead.org/), or other sources.

Figure 5:
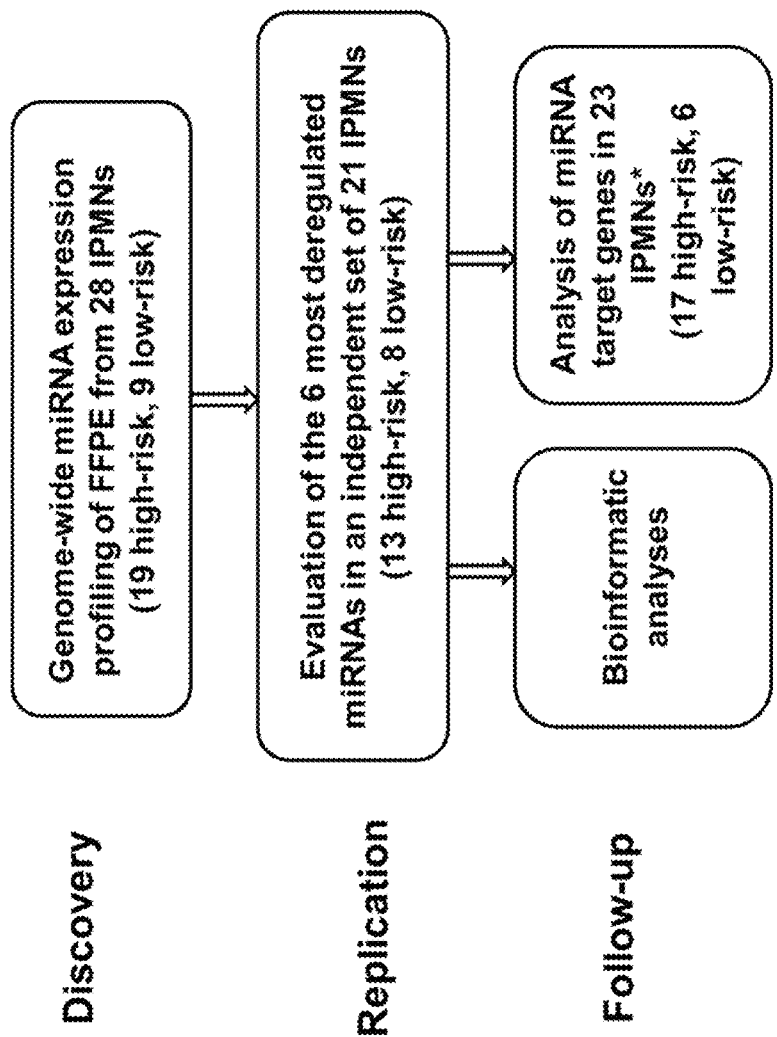
FIG. 5. Schema illustrating the three study phases. In the discovery phase, genome-wide miRNA expression profiling of formalin-fixed paraffin-embedded (FFPE) tissue from 28 IPMNs was conducted. This was followed by a replication phase in which the six most degregulated miRNAs from the discovery phase (miR-100, miR-99b, miR-99a, miR-342-3p, miR-126, and miR-130a) were evaluated in an independent set of 21 IPMNs, while accounting for pertinent clinical and pathologic variables. In the final phase, a two-pronged approach was used to follow up findings: a) bioinformatics analyses were conducted to identify genes and pathways regulated by the candidate miRNAs and b) analysis was performed for candidate genes believed to be regulated by the identified miRNAs using existing microarray data for 23 IPMNs.
Figure 6A:
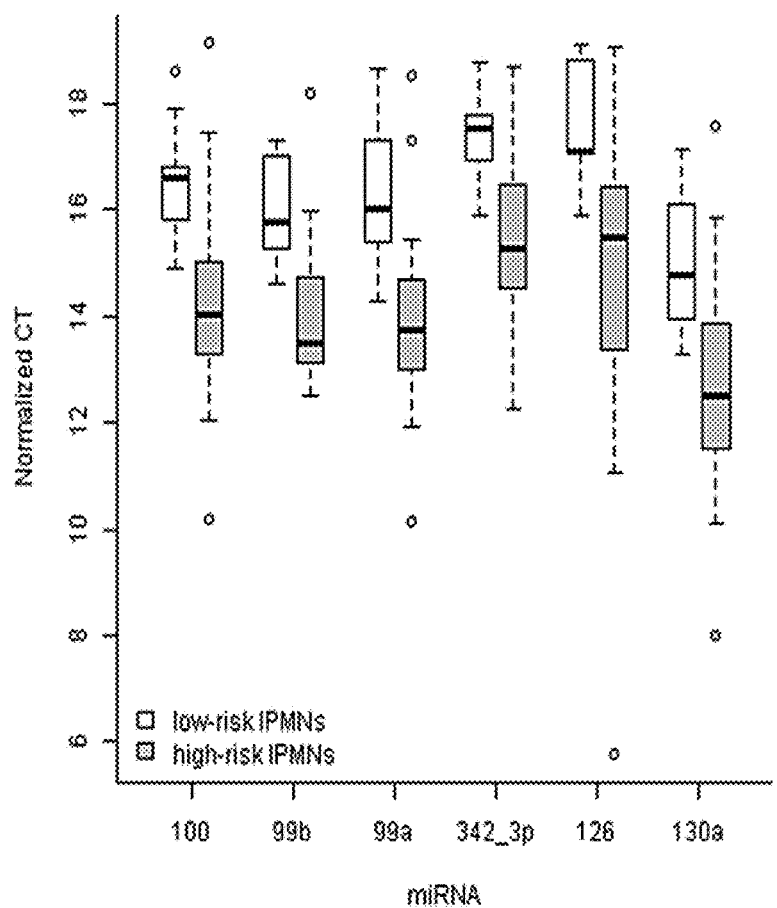
FIGS. 6A and 6B. Box plots of candidate miRNA expression in IPMN tissue by real-time PCR.
Figure 6B:
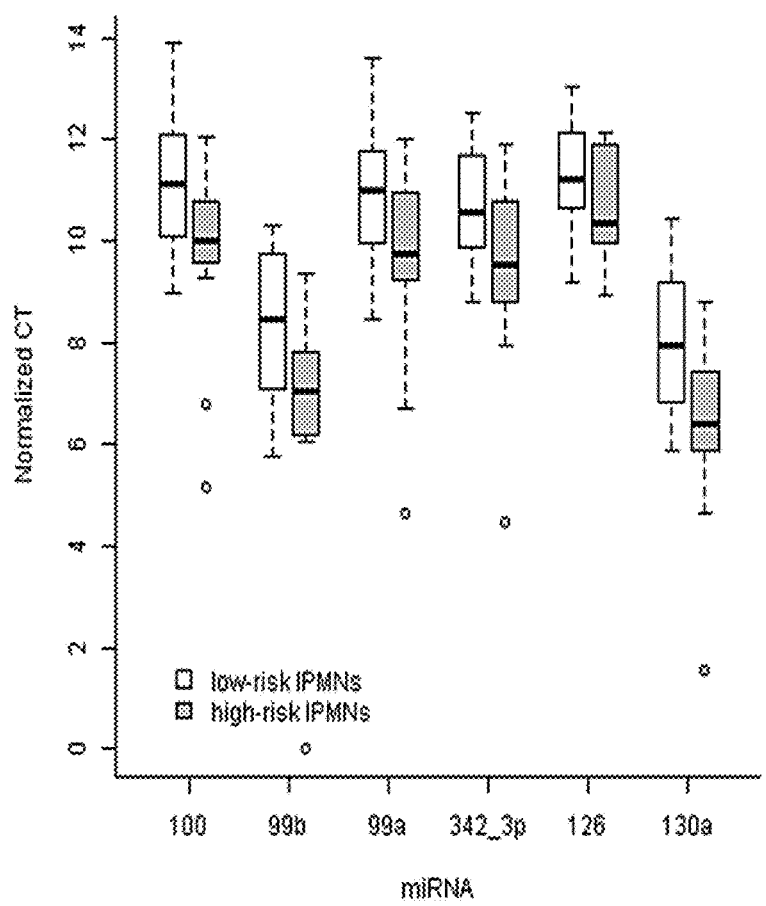

In the replication phase, expression of miR-100, miR-99b, miR-99a, miR-342-3p, miR-126, and miR-130a was evaluated in 21 independent IPMNs (13 high-risk and 8 low-risk) (FIG. 5). The same trends in expression as in the discovery phase were observed with the expression levels of each miRNA down-regulated in high-risk compared to low risk IPMNs (FIGS. 6A and 6B). Using a threshold of p<0.05, results reached marginal statistical significance, possibly due to the small sample size. Among the 6 miRNAs evaluated, miR-130a was most strongly associated with high-risk IPMN status (2.9 median fold change between the high- and low-risk group, p=0.065), followed by miR-99b (2.7 median fold change, p=0.103) and miR-100 and miR-342-3p (2.2 median fold-change, p=0.119). Most clinical and pathological factors were not correlated with miRNA expression level in the discovery phase (Table 4). However, an association was observed between low miR-99b expression and main duct involvement (P=0.021), a variable independently associated with high-risk IPMN status (P=0.044). After including both miR-99b expression level and main duct involvement in multivariate regression models, low miR-99b expression was marginally associated with high-risk IPMN status (P=0.051). Serum albumin levels were positively correlated with miR-99a (r=0.52, P=0.004) and miR-100 expression (r=0.49, P=0.008).

The expression level of several miRNAs (miR-99a, miR-99b, miR-100) was highly correlated (0.79<r<0.97), which may be expected since they are from the same miRNA family (Table 4). No factors were associated with miRNA expression (P<0.05) in the replication phase.

TABLE 4

Correlations between candidate miRNA expression level and selected continuous clinical and pathologic characteristics

|  |  | miR_100 | | miR_99b | | miR_99a | | miR_342_3p | | miR_126 | | miR_130a | |
|---|---|---|---|---|---|---|---|---|---|---|---|---|---|
|  | N | r | P | r | P | r | P | r | P | r | P | r | P |
| Age at diagnosis (years) | 28 | −0.14 | 0.47 | −0.02 | 0.93 | −0.16 | 0.42 | 0.19 | 0.34 | −0.25 | 0.2 | −0.18 | 0.37 |
| Size of the Largest Cyst (cm) | 28 | −0.1 | 0.63 | −0.15 | 0.45 | −0.21 | 0.28 | −0.24 | 0.21 | −0.2 | 0.32 | −0.19 | 0.34 |
| Size of the Main Pancreatic Duct (mm) | 15 | −0.48 | 0.07 | −0.49 | 0.07 | −0.33 | 0.23 | −0.17 | 0.55 | −0.13 | 0.65 | −0.49 | 0.07 |
| Fluid CEA levels (ng/uL) | 16 | −0.24 | 0.36 | −0.16 | 0.56 | −0.13 | 0.62 | −0.08 | 0.77 | −0.42 | 0.11 | −0.33 | 0.22 |
| Serum glucose levels (mg/dL) | 27 | −0.17 | 0.4 | −0.19 | 0.34 | −0.18 | 0.38 | −0.29 | 0.14 | 0.19 | 0.33 | −0.05 | 0.79 |
| Serum amylase level (u/L) | 10 | 0.4 | 0.25 | 0.24 | 0.5 | 0.214 | 0.55 | 0.44 | 0.2 | 0.54 | 0.11 | −0.17 | 0.65 |
| Serum CA19-9 level (U/ml) | 21 | 0.04 | 0.86 | 0.18 | 0.44 | −0.16 | 0.49 | −0.08 | 0.74 | −0.02 | 0.95 | 0.026 | 0.91 |
| Serum CEA level (ng/mL) | 7 | 0.32 | 0.49 | 0.02 | 0.96 | 0.3 | 0.51 | 0.31 | 0.5 | 0.46 | 0.3 | 0.468 | 0.29 |
| Serum albumin level (g/dL) | 28 | 0.49 | 0.01 | 0.31 | 0.11 | 0.524 | 0 | 0.37 | 0.05 | 0.09 | 0.67 | 0.253 | 0.19 |
| Serum bilirubin level (mg/dL) | 28 | 0.1 | 0.62 | 0.09 | 0.66 | 0.014 | 0.95 | 0.1 | 0.61 | 0.09 | 0.66 | −0 | 0.99 |
| Serum alkaline phosphatase level (u/L) | 28 | 0.17 | 0.39 | 0.1 | 0.63 | 0.08 | 0.69 | 0.14 | 0.49 | 0.1 | 0.61 | 0.081 | 0.68 |
| Body mass index (BMI) (kg/m$^2$) | 27 | −0.11 | 0.6 | −0.15 | 0.45 | −0.1 | 0.64 | 0.01 | 0.96 | 0.16 | 0.43 | 0.044 | 0.83 |
| Pack Years Smoked | 18 | 0.5 | 0.03 | 0.48 | 0.05 | 0.434 | 0.07 | 0.38 | 0.12 | 0.03 | 0.91 | 0.197 | 0.43 |
| miR-100 | 28 | 1 | NA | 0.82 | 0 | 0.969 | 0 | 0.7 | 0 | 0.43 | 0.02 | 0.864 | 0 |
| miR-99b | 28 | 0.82 | 0 | 1 | NA | 0.795 | 0 | 0.72 | 0 | 0.29 | 0.13 | 0.82 | 0 |

TABLE 4-continued

Correlations between candidate miRNA expression level and selected continuous clinical and pathologic characteristics

|  | N | miR_100 r | miR_100 P | miR_99b r | miR_99b P | miR_99a r | miR_99a P | miR_342_3p r | miR_342_3p P | miR_126 r | miR_126 P | miR_130a r | miR_130a P |
|---|---|---|---|---|---|---|---|---|---|---|---|---|---|
| miR-99a | 28 | 0.97 | 0 | 0.8 | 0 | 1 | NA | 0.72 | 0 | 0.44 | 0.02 | 0.858 | 0 |
| miR-342_3p | 28 | 0.7 | 0 | 0.72 | 0 | 0.715 | 0 | 1 | NA | 0.22 | 0.25 | 0.593 | 0 |
| miR-126 | 28 | 0.43 | 0.02 | 0.29 | 0.13 | 0.443 | 0.02 | 0.22 | 0.25 | 1 | NA | 0.569 | 0 |
| miR-130a | 28 | 0.86 | 0 | 0.82 | 0 | 0.858 | 0 | 0.59 | 0 | 0.57 | 0 | 1 | NA | r = Pearson correlation

Figure 3:
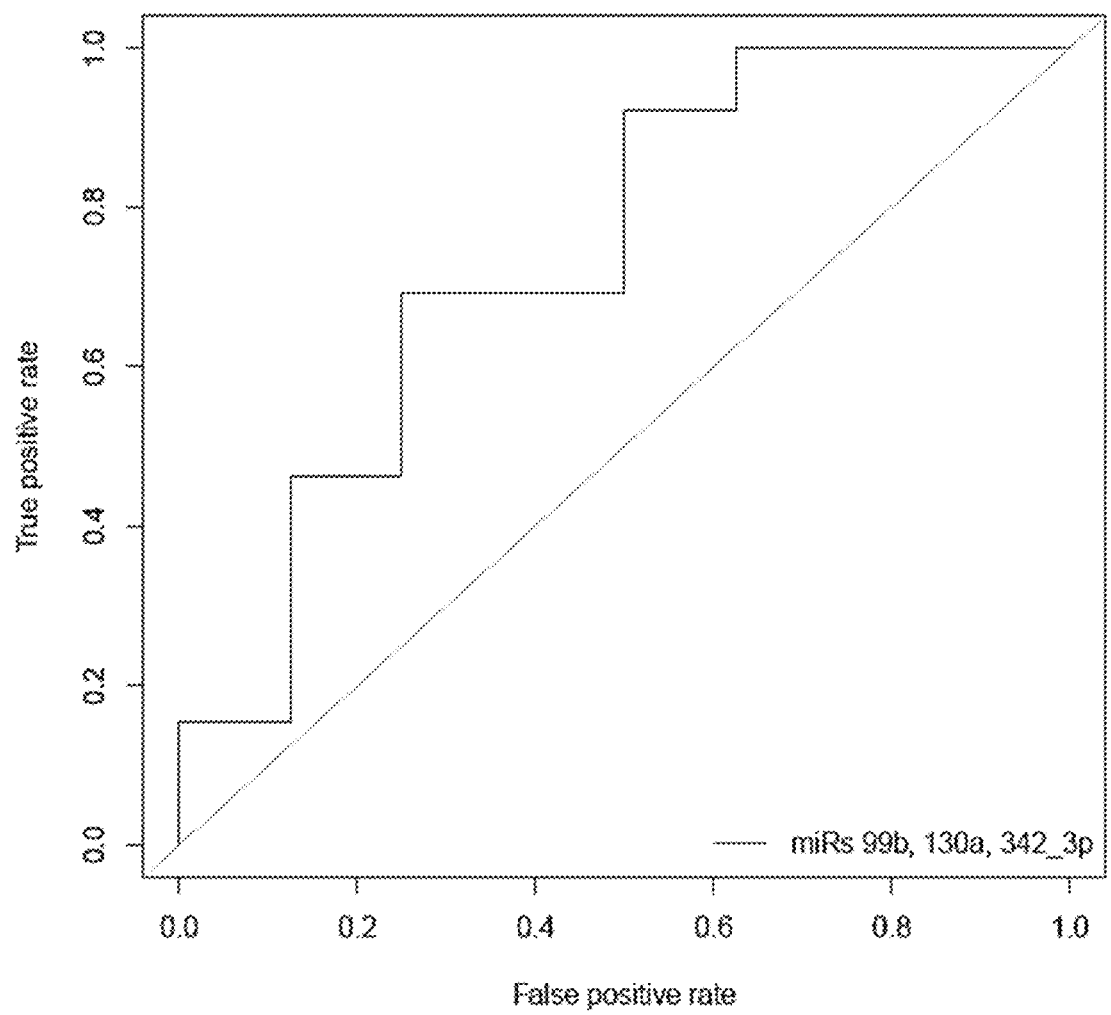
FIG. 3. Receiver operating characteristic (ROC) curve analysis using miRNA expression to discriminate high-risk from low-risk IPMN samples. Using a logistic regression model built on data from the discovery dataset, a miRNA signature consisting of miR-99b, miR-130a, and mir-342-3p yielded an area underneath the curve (AUC) value of 0.74 (95% CI: 0.51-0.97) in differentiating between 13 high-risk and 8 low-risk IPMNs in the replication phase.
Figure 4A:
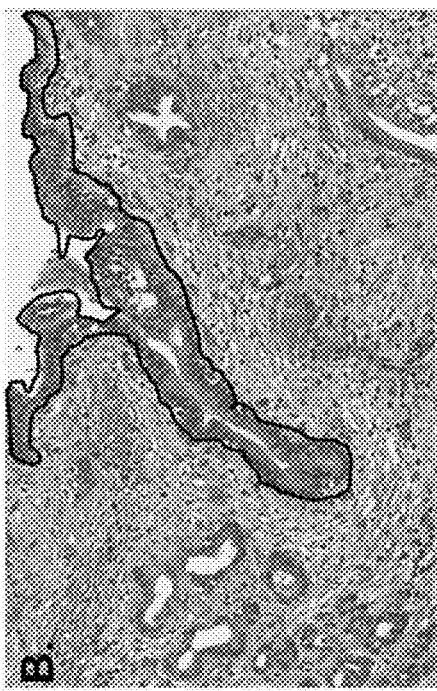
FIGS. 4A-4D. Representative histologic images of IPMNs with low-grade (FIG. 4A), moderate-grade (FIG. 4B), and high-grade dysplasia (FIG. 4C) and invasive (FIG. 4D) carcinoma. The region enclosed by the black line represents the area isolated by LCM. Reference bar=50 micrometers (mm).
Figure 4B:
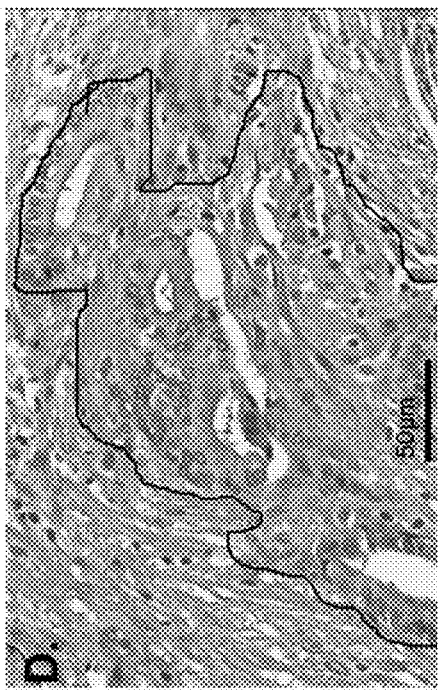
Figure 4C:
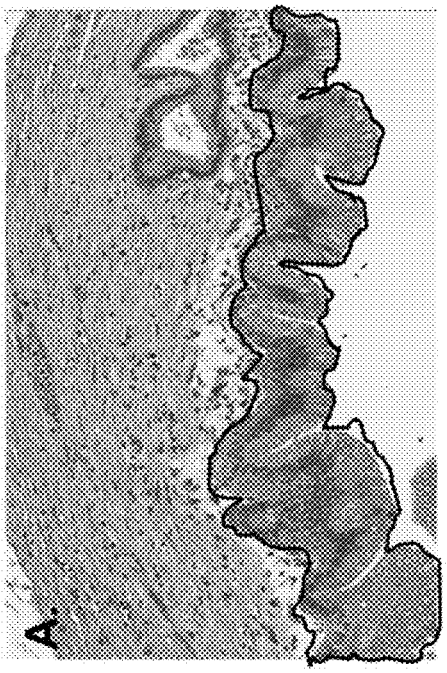
Figure 4D:
Figure 7A:
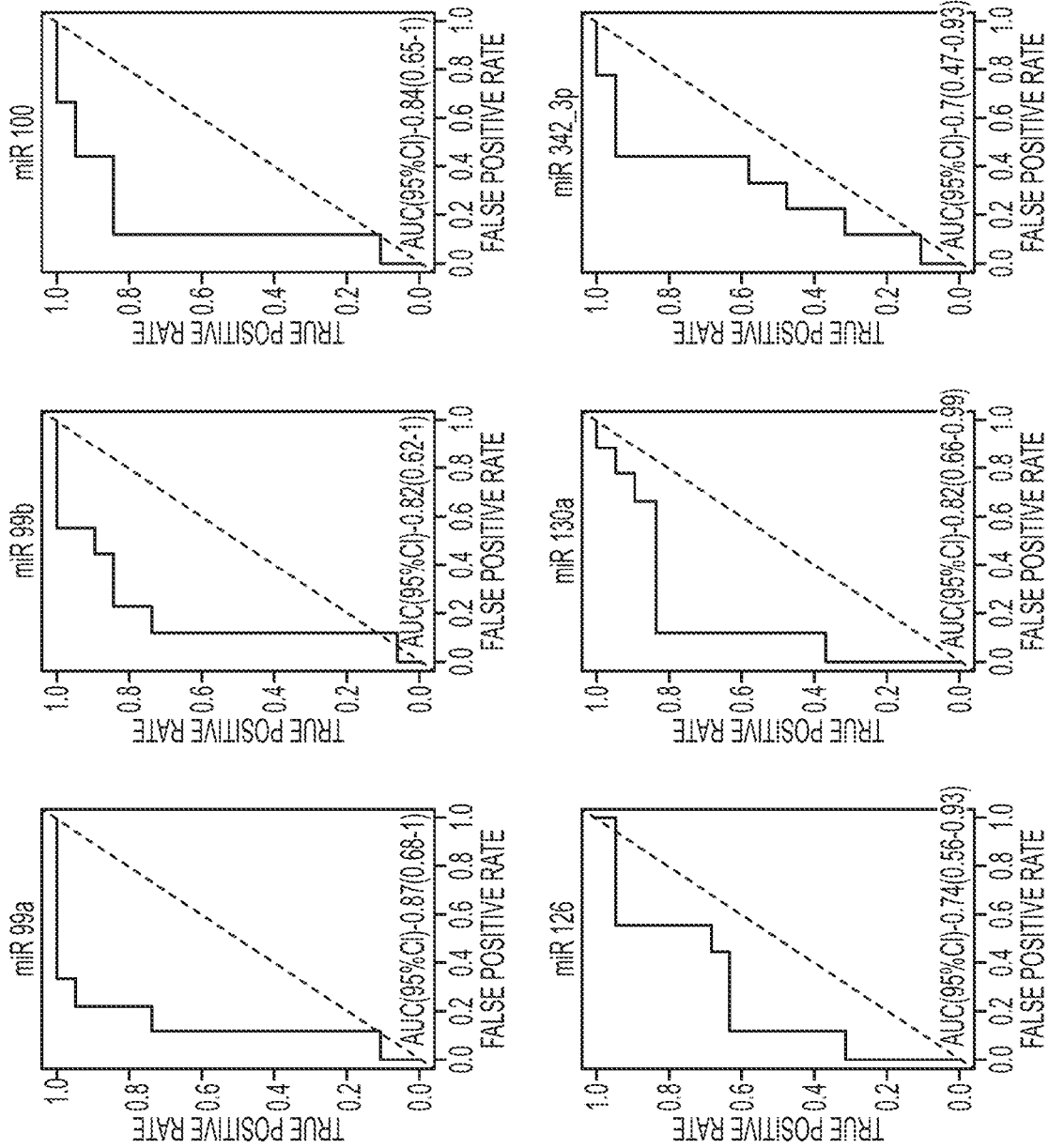
FIGS. 7A and 7B. Receiver operating characteristic (ROC) curve analysis using miRNA expression to discriminate high-risk from low-risk IPMNs in the discovery (FIG. 7A) and replication (FIG. 7B) phase.
Figure 7B:
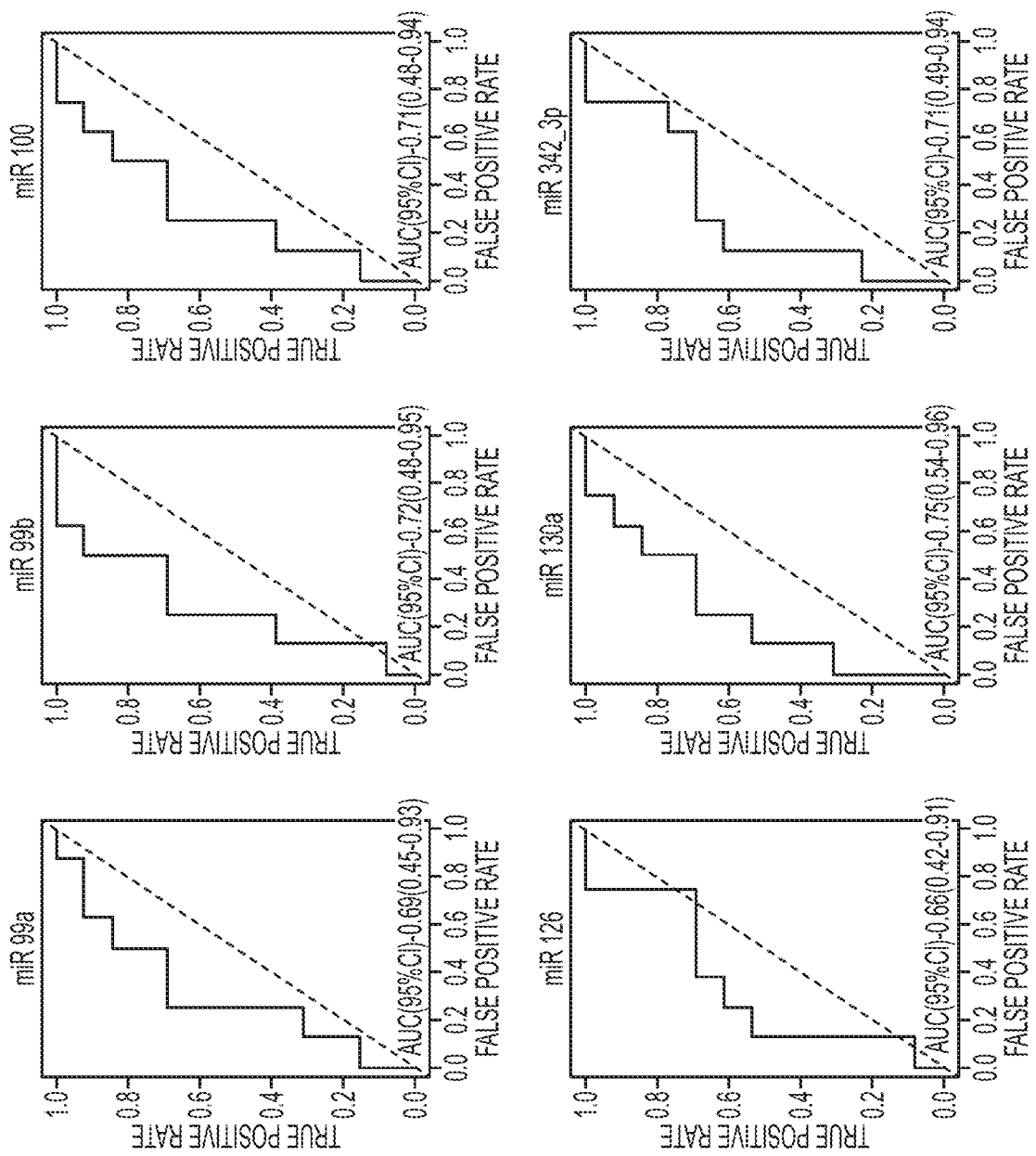

Receiver operating characteristic (ROC) curves were constructed based on the expression of miR-100, miR-99b, miR-99a, miR-342-3p, miR-126, and miR-130a. Most areas underneath the curve (AUC) values were comparable for the six individual miRNAs, with expression of miR-99a yielding the highest AUC value of 0.87 in classifying between high- and low-risk IPMNs in the discovery phase (FIG. 7A). When using a signature consisting of three miRNAs (miR-99b, miR-130a, and miR-342-3p) from the discovery model to predict high-risk IPMN status in the replication set, the AUC was 0.74 (95% CI: 0.51-0.97) (FIG. 3). A model combining expression of miR-99b, miR-130a, and miR-342-3p with presence of main duct involvement enabled slightly higher utility in discriminating between groups (AUC=0.81).

Figure 8:
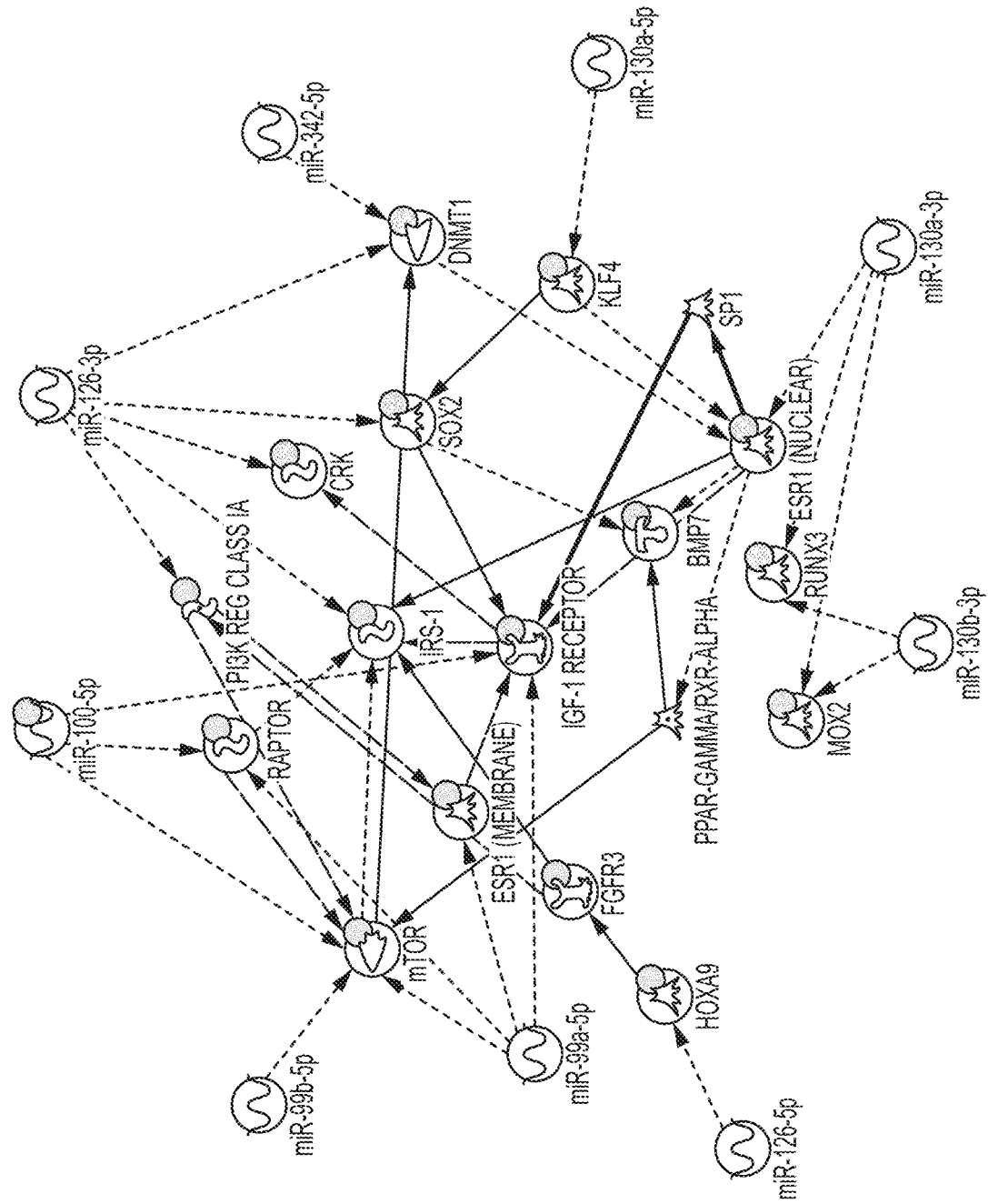
FIG. 8. Network of genes regulated by candidate miRNAs (miR-100, miR-99a, miR-99b, miR-342-3p, miR-126, and miR-130a) that were found to be differentially expressed between high- and low-risk IPMNs.
Figure 9:
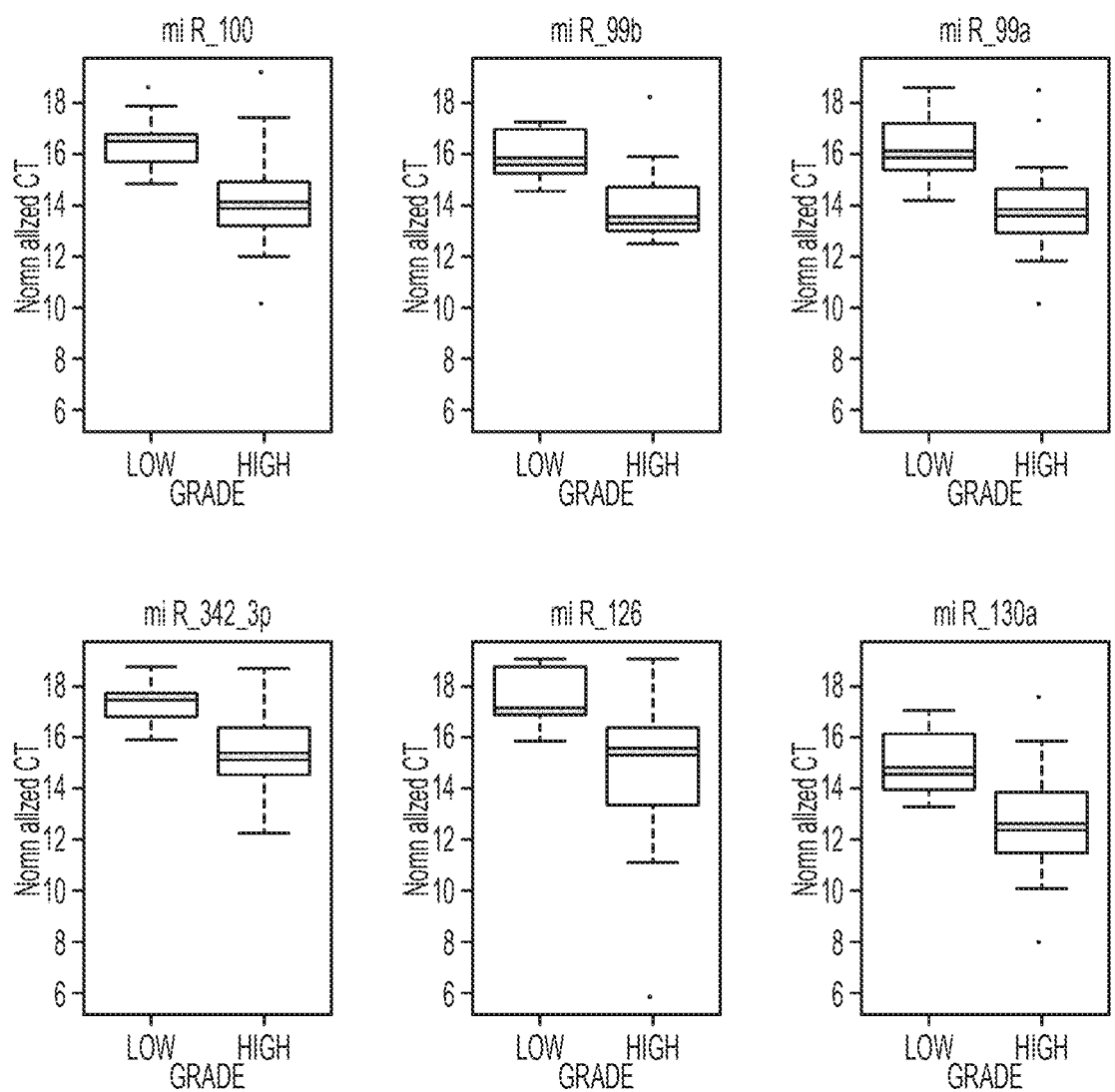
FIG. 9. Box plots of miRNA expression in IPMN tissue by real-time PCR. The expression level of the top-ranked miRNAs was down-regulated in high-grade compared to low-grade IPMN tissue.

D. Follow-up with bioinformatics analyses and gene expression profiling Gene ontology pathway enrichment network analysis revealed several important interaction hubs, including ESR1, PPARG, VEGF-A, mTOR, IRS-1, and SOX2 (FIG. 8). The top four most marked gene ontology maps that were identified contribute to tumor progression through interactions with histone deacetylase and calcium/calmodulin-dependent kinases, hypoxia inducible factor regulation, growth factors signaling, and cytoskeleton remodeling (Table 5). This analysis also confirmed that identified target genes were associated with pancreatic diseases ($2.2 \times 10^{-30}$) and pancreatic neoplasms ($7.6 \times 10^{-29}$).

TABLE 5

Gene ontology categories of biological pathways overrepresented by miRNA-mediated changes in target gene expression that may differentiate between high- and low-risk IPMNs.

| Pathway | P-value | False Discovery Rate (FDR) |
|---|---|---|
| Developmental role of histone deacetylase (HDAC) and calcium/calmodulin-depdendent kinase (CaMK) | $9.5 \times 10^{-8}$ | $2.4 \times 10^{-5}$ |
| Transcription receptor-mediated hypoxia inducible factor (HIF) regulation | $5.9 \times 10^{-7}$ | $7.5 \times 10^{-5}$ |
| Developmental membrane-bound ESR1: interaction with growth factors signaling | $1.3 \times 10^{-6}$ | $1.0 \times 10^{-4}$ |
| Cytoskeleton remodeling with TGF and WNT | $6.9 \times 10^{-6}$ | $3.8 \times 10^{-4}$ |
| DNA damage with BRCA1 as a transcription regulator | $7.5 \times 10^{-7}$ | $3.8 \times 10^{-4}$ |
| Signal transduction-AKT signaling | $3.3 \times 10^{-5}$ | $8.9 \times 10^{-4}$ |
| Development: VEGF signaling and activation | $3.3 \times 10^{-5}$ | $8.9 \times 10^{-4}$ |
| Development: ligand-independent activation of ESR1 and ESR2 | $3.9 \times 10^{-5}$ | $8.9 \times 10^{-4}$ |
| Role of alpha-6/beta-4 integrins in carcinoma progression | $3.9 \times 10^{-5}$ | $8.9 \times 10^{-4}$ |

Gene expression was significantly up-regulated in 17 high-risk versus 6 low-risk IPMNs for DNMT1, ATG2B, MEOX2, and IRS1 (p<0.10 and FDR<0.30). Correlations between miRNA and mRNA expression were evident in 2 miRNA-mRNA pairs, miR-342-3p: DNMT1 (r=0.81, p=0.05) and miR-126: IRS1 (r=0.78, p=0.07). No statistically significant inverse correlations between miRNAs and their target genes were observed.

miRNA expression analysis of IPMNs that was followed by both a replication and a functional follow-up phase, biologically meaningful miRNAs that help distinguish between high- and low-risk IPMNs were discovered. Six miRNAs (miR-100, miR-99b, miR-99a, miR-342-3p, miR-126, and miR-130a) were under-expressed in high-risk compared to low-risk IPMNs in the discovery and replication phase, suggesting that low or reduced levels of these miRNAs (and possibly increased levels of target genes they regulate) may be associated with progression to invasion. Moreover, ROC analysis suggested that a combination of these miRNAs may accurately classify IPMNs based on histologic severity (FIG. 3).

The identified miRNAs can have a role as tumor suppressors and regulators of oncogenes that contribute to cell proliferation and invasion in pancreatic and other malignancies (Table 3)(30-37). For example, an experimentally-validated target of miR-100 is polo-like kinase 1 (PLK1), a regulator of proliferative activity overexpressed in early PDAC (36) that represents a novel target for chemoprevention and therapeutic strategies (36, 38). Also noteworthy, miR-342-3p can inhibit cancer cell proliferation and invasion by directly targeting DNA methyltransferase 1 (DNMT1), a gene that maintains DNA methylation (35). DNMT1 mRNA expression has been correlated with PDAC progression; those with higher DNMT1 tissue expression had poorer survival than those with lower expression (37). Loss of another candidate, miR-126, has been associated with PDAC progression by targeting oncogenes such as KRAS (31, 32) and insulin receptor substrate-1 (IRS-1), a mediator of phosphoinositide 3-kinase (PI3K) activation in quiescent PDAC cells (39).

Pathway enrichment network analysis underscored that these and other miRNA-mediated mechanisms may explain how IPMNs progress to invasive disease (Table 5). Even though miRNAs are generally believed to regulate expression at the protein level (15), we postulated that measuring mRNA expression may be useful for determining how transcriptional machinery differs between a pre-malignant and a malignant IPMN state.

Consistent with our predictions, mRNA targets of miR-130a (ATG2B and MEOX2), miR-342-3p (DNMT1), and miR-126 (IRS-1) were up-regulated in high-risk versus low-risk IPMNs. Other miRNA targets may not have demonstrated noticeable mRNA level changes since a strong correlation between mRNA and protein abundance may not exist (40). We also explored correlations between miRNA and mRNA expression in the reduced set of IPMNs with both data types. Although positive correlations were observed in 2 miRNA-mRNA pairs (miR-342-3p:DNMT1 (r=0.81, p=0.05) and miR-126: IRS1 (r=0.78, p=0.07)), no statistically significant inverse miRNA:target gene correlations were observed. Indeed, previous studies observed more positively correlated than negatively correlated interactions (41), supporting a positive regulatory role of miRNAs (42). Due to the modest sample size of IPMNs evaluated, caution should be taken when interpreting these mRNA-based findings. Tissue microarrays are being constructed on a larger series of IPMNs so that protein expression can be evaluated.

Matthaei et al. (28) and Lubezky et al. (29) also conducted genome-wide miRNA profiling (Table 6). Matthaei et al. (28) evaluated miRNA expression in 22 IPMN tissue and 7 pancreatic cyst fluid (CF) samples, and performed validation using 23 additional IPMN FFPE samples and CF samples. miR-342-3p and miR-99b were among the miRNAs that differentiated between high- and low-risk groups using FFPE tissue (and CF) (28), demonstrating consistency of findings across our two studies and providing a form of external validation. No overlap existed between findings observed by Lubezky et al. (29) and the current study (Table 6).

because it would be opportune for the medical team to have a diagnostic adjunct that could reliably detect high-grade dysplasia so that intervention could occur prior to invasion. Also of clinical importance, we observed that low miR-99b expression was associated with main duct involvement, a marker of histologic progression that was not observed pre-operatively by imaging for six HG cases in our study.

We also observed positive correlations between serum albumin levels and expression of miR-99a and miR-100, findings in line with data suggesting that high serum albumin is correlated with better survival in PDAC patients (45) (and with low-grade disease in our study). This infers that it may be helpful to monitor serum albumin levels in patients with IPMNs. Larger prospective studies are needed to validate these observations.

Additional strengths of our study include the well-annotated tissue and sound methodologic approach which capitalized upon confirmatory pathological review, standardized procedures for microdissection and RNA isolation of multiple representative regions per case, an established platform for miRNA profiling, and our functional follow-up using bioinformatics tools and available microarray data. Internal

TABLE 6

Studies of tissue-based miRNA expression in surgically-resected IPMNs.

| | Habbe [26] | Matthaei [28] | Park [43] | Lubezky [29] | Caponi [44] | Current Invention |
|---|---|---|---|---|---|---|
| Discovery phase | | | | | | |
| N IPMNs[a] | 15 (non-inv) | 22 (10 LG, 12 HG[b]) | 2 (1 LG, 1 HG) | 30 (10 LG, 5 MG, 5 HG, 10 inv) | 81 (16 non-inv, 65 inv) | 28 (9 LG, 19 HG) |
| Platform | Taqman Singleplex qRT-PCR | Taqman MiRNA Array/ qRT- PCR | cDNA-mediated ligation | Gene Chip miRNA Array | Taqman Singleplex qRT-PCR | Taqman MiRNA Array/ qRT-PCR |
| N miRNAs evaluated (normalization method) | 12 [c] (RNU6B[e]) | 750 ('diffpairs') | NA | 850 (Robust multi-chip array algorithm) | 3 [d] (RNU6[e]) | 378 (RNU44[e]) |
| Replication phase[f] | | | | | | |
| N IPMNs | 64 (13 LG, 31 MG, 20 HG) | 23 (3 LG, 9 HG, 11 inv) | 20 (NA) | 18 (9 LG, 9 inv) | None | 21 (4 LG, 4 MG, 11 HG, 2 inv) |
| Platform (N miRNAs evaluated) | LNA-ISH (2) | qRT-PCR (26[f]) | qRT-PCR (NA) | qRT-PCR (4) | NA | qRT-PCR (6) |
| Most deregulated miRNAs in high- versus low-risk IPMNs [g] | miR-21, -155 | miR-24, -18a, -30a-3p, -92a, -106b, -342-3p, -99b, -142-3p, -532-3p | miR-552, -25, -182, -1300, -183 -196a, -30c | miR-217, -21, -708, -155 | miR-21, -155 | miR-100, -99b, -99a, -342-3p, -126, -130a |

Abbreviations: IPMN = intraductal papillary mucinous neoplasm; inv = invasive; LG = low-grade; MG = moderate-grade; HG = high-grade; LNA-ISH = locked nucleic acid-in situ hybridization; NA = not available.
[a] Some studies also evaluated normal pancreas tissue, PDAC tissue, and/or biofluids (pancreatic cyst fluid or pancreatic juice).
[b] 7 of the 12 HG IPMNs had associated invasive disease.
[c] The 12 evaluated miRNAs include: miR-15a, -16, 17-5p, -21, -100, -107, -155, -181a, -181c, -210, -221, -223.
[d] The 3 miRNAs that were evaluated include: miR-21, -155, -101.
[e] Endogenous control
[f] Represents the number of independent IPMNs in addition to those profiled in the discovery phase.
[g] miRNAs appearing in bold font were highlighted in more than one investigation. The 9 miRNAs highlighted by Matthaei et al. are represented in their final predictive model which was also based on cyst fluid analysis.

Since factors differed between studies (study population characteristics, sample preparation procedures, the platform used (qRT-PCR versus microarray), normalization approaches, etc.), it is not surprising that different miRNAs were characteristic of high-risk IPMN status (Table 6). Although the sample sizes of our discovery and replication phases were relatively modest, they were comparable or even larger than other studies with regard to the number of high-grade cases without associated invasion that were evaluated. This is important from a clinical standpoint validity of our findings is evidenced by high correlations between expression levels of miRNAs from the same family within and between samples. One limitation was the fact that we evaluated resected tissue. Some of these cysts (those deemed to be low- or moderate grade upon pathologic review) would not have been removed if tools were available to have properly diagnosed them pre-operatively.

Taken together, the new miRNAs identified here (e.g., miR-99a, miR-100, miR-126, miR-130a) and the miRNAs that have also been highlighted by other tissue-based studies of IPMNs (e.g., miR-99b, -342-3p) warrant consideration as biomarkers. Moreover, given that miRNAs are released from tissues into circulation in a stable form protected from endogenous RNAse activity (46) and preliminary data support the clinical utility of miRNAs circulating in pancreatic juice or aspirate (20, 47), cyst fluid (28), and serum (48), there is great potential for a minimally-invasive miRNA-based assay to be used in the clinic to classify newly-diagnosed pancreatic cysts based on their malignant potential. Such an assay should be evaluated in conjunction with clinical and pathologic factors and emerging analytes and genetic markers (49, 50) to increase sensitivity and specificity.

Furthermore, functional evaluation of the biological processes in which the emerging miRNAs and their target genes are involved may aid in understanding the molecular underpinnings of progression to pancreatic malignancy so that novel prevention and early detection strategies can be developed. In conclusion, a miRNA signature has the potential to serve as a promising diagnostic adjunct for directing management of newly-diagnosed IPMNs toward watchful waiting or resection. This investigation provides novel biological insights into progression to pancreatic malignancy, and has potential to advance this field closer to solving this clinical challenge.

Materials and Methods for Example 2

Study population and biospecimens. A prospectively maintained clinical database was retrospectively reviewed to identify individuals who underwent a pancreatic resection for an IPMN between 2006 and 2011 at H. Lee Moffitt Cancer Center and Research Institute (Moffitt) and had provided written consent for blood to be donated preoperatively for research through several protocols approved by the Institutional Review Board (IRB) of the University of South Florida, including Total Cancer Care (see moffitt.org website) (27). IRB approval was also specifically granted for the research described herein (IRB #Pro4971). The diagnosis and degree of dysplasia was histologically confirmed using World Health Organization (WHO) guidelines (22). The final diagnosis represented the most severe grade of dysplasia observed in the neoplastic epithelium of each resected lesion. None of the cases received pre-operative chemotherapy or radiation. Age- and gender-matched healthy controls with no current or prior history of pancreatic disease or symptoms who presented to Moffitt's Cancer Screening and Prevention Center during the same time period and donated blood through a related IRB-approved protocol using the same procedures were also eligible for inclusion.

Blood was collected from consented participants via phlebotomy in a 7 mL EDTA tube and processed for plasma within two hours using standard procedures (60). The EDTA tube was inverted 3 times and spun at 3600 rpm for 8 minutes and then plasma was aliquoted into 0.5 mL barcoded cryovials and banked at −80° C. Demographic, clinical, and epidemiologic data from all subjects was collected from an electronic questionnaire, the medical record, Moffitt's cancer registry, and other source systems.

RNA isolation from plasma and quality control. While using precautions to prevent RNAse contamination and RNA degradation, one 0.5 mL cryovial of plasma was retrieved and thawed from each subject. To control for variance in the starting material and the efficiency of the downstream total RNA extraction step, RNA spike-in miR-NAs (synthetic control templates) were used according to manufacturer protocols and published recommendations (61). Total RNA isolation that includes small RNAs was performed on 500 uL of plasma using the Plasma/Serum Circulating and Exosomal RNA Purification Mini Kit (Slurry Format) from Norgen Biotek (Ontario, Canada) according to manufacturer protocols. This kit was chosen due to its ability to isolate total RNA of pure quality and ample quantity from plasma (62). After adding lysis buffer to the plasma samples, 1000 attomoles of the synthetic RNA oligonucleotides (spike-in oligos) osa-miR-414, cel-mi-248, and ath-miR-159a (Operon, Inc, Huntsville, Ala.) were added. No-template control samples were run to monitor the baseline for the spike-ins. RNA was eluted in 100 µL water, concentrated to 20 µL using Amicon Ultra 0.5 mL ceintrifugal filters with a 3 KDa molecular weight cut-off (Sigma-Alrich, St. Louis, MO), and 3 µL was used for each NanoString assay.

Total RNA concentration and integrity were assessed using the NanoDrop spectrophotometer (NanoDrop Technologies, Waltham, MA) and an Agilent Bioanalyzer (Agilent, Santa Clara, CA), respectively. Since hemolysis (rupturing of erythrocytes) can be a source of variation in studies of circulating miRNAs, a multi-pronged approach was used to assess the possibility of hemolysis based on recommended guidelines (63-65): a) prior to RNA extraction, samples were visually inspected for a pink/red hue, b) oxygen hemoglobin absorbance of isolated RNA was measured at $\lambda=414$ nm, with values exceeding 0.2 indicative of hemolysis, and c) signal levels were evaluated post-hoc for cellular miRNAs likely to be elevated in the presence of hemolysis (i.e., miR-451, miR-16).

High-throughput measurement of miRNA abundance. The NCOUNTER™ Human v2 miRNA Expression Assay Codeset (Nanostring Technologies, Seattle, Wash., USA) was used to simultaneously quantify the abundance of 800 human miRNAs. The Codeset also includes two types of built-in controls: positive controls (spiked RNA at various concentrations to assess overall assay performance, n=6) and negative controls (alien probes for background calculation, n=8). The NCOUNTER™ platform was selected because of its greater sensitivity and precision than microarrays and Taqman-based qRT-PCR (66). Additionally, since RNA isolated from plasma contains inhibitors of the reverse transcriptase and Taq polymerase enzymes used in qPCR, Nanostring's technology has an advantage over PCR-based methods in that reverse transcription and amplification steps that may introduce bias are not required (59). This platform involves direct digital measurement of miRNA abundance using color-coded probe pairs which contain a reporter probe (to carry a fluorescent signal) and a capture probe (to immobilize the complex for data collection) (59). Using 3 µL of the extracted plasma RNA as input, preparation involved multiplexed ligation of DNA sequences called miRtags to the mature miRNAs through sequence-specific oligonucleotide bridges in a single tube by controlling annealing and ligation temperatures. Excess tags and bridges were removed via an enzymatic step, and the tagged mature miRNA probes were hybridized to a color-coded reporter probe pair for data collection. Reporter probes were counted for each miRNA using the NCOUNTER Digital Analyzer at a setting of 555 fields of view (FOV).

Data Processing and Quality Control. For each sample, background-corrected measures of miRNA expression were estimated by subtracting the negative control average plus two standard deviation (SD) cut-point from the raw miRNA counts. miRNAs with less than 20% of samples above the negative control cut-point (i.e., low-expression probes) were removed from downstream analysis, leaving only those miRNAs with substantial counts above background. Human messenger RNA (mRNA) housekeeping genes included in the codeset (ACTB, B2M, GAPDH, RPL19 and RPLP0) were used to evaluate possible sample contamination. To account for variances in the starting material and RNA extraction efficiency, data for each sample was normalized using the geometric mean of the 3 spike-in oligos. Biological normalization was then performed using the four most stable/invariant circulating miRNAs as endogenous controls, similar to other studies (67,68). Any of the four miRNAs that were known to cross-hybridize with the spike-ins or known to be affected by hemolysis were replaced with the next most stable/invariant circulating miRNA. Normalized data was log 2-transformed prior to signature selection.

Statistical Analysis. Descriptive statistics were determined using frequencies and percents for categorical variables and means and standard deviations (SD) for continuous variables.

Identification of a plasma miRNA signature to differentiate between IPMN cases and controls: To identify miRNAs that differentiate between IPMN cases and non-diseased controls, we used linear models for microarray data (LIMMA) (69), a Bayesian t-test that accounts for multiple comparisons. miRNAs with false discovery rates (FDR) <15% were included in the signature. Principal component analysis (PCA) was then used to efficiently reduce the data dimension into a small set of uncorrelated principal components presumably linked to biological effects and to generate an overall 'IPMN-risk score' to represent the overall combined effect of the IPMN-risk miRNA signature. To represent the overall expression level for the signature, we used the first principal component (PC1, a weighted average of expression among the identified miRNAs), as it accounts for the largest variability in the data. That is, IPMN-risk score=$\Sigma w_i x_i$, a weighted average expression among the IPMN-risk miRNAs, where $x_i$ represents miRNA i expression level, $w_i$ is the corresponding weight (loading coefficient) with $\Sigma w_i^2=1$, and the $w_i$ values maximize the variance of $\Sigma w_i x_i$. This approach has been used to derive a malignancy-risk gene signature previously (70,71). Receiver operating characteristic (ROC) curves were generated to measure the predictive power of the IPMN-risk signature in discriminating between groups.

Pathway Enrichment Analysis: To explore the potential roles of identified circulating miRNAs in pancreatic carcinogenesis, we applied pathway-based bioinformatics exploratory analysis. Using Tarbase 6.0, we obtained a list of genes experimentally-validated to target the identified miRNAs. The target genes were then analyzed to identify enriched KEGG pathways (see worldwideweb.genome.jp/kegg/) that are predicted to be regulated by these circulating miRNAs.

Identification of a plasma miRNA signature to differentiate between malignant and benign IPMNs: We also used LIMMA (69) and the PCA approach (70,71) to identify a miRNA signature that distinguishes between malignant (pathologically-confirmed as high-grade or invasive) and benign IPMNs (pathologically-confirmed as low- or moderate-grade). An unadjusted alpha of 0.05 was used as a threshold for inclusion in the signature. To evaluate possible associations between selected predictors of malignant potential (i.e., main-duct involvement, lesion size, serum CA-19-9 level) (8) and IPMN-risk status (malignant vs. benign), we used the Wilcoxon Rank Sum test and the Chi-squared test for continuous and categorical variables, respectively. The exact method with Monte Carlo estimation was used for both variable types. Multivariable logistic regression analysis was then conducted to assess whether the identified miRNA signature was associated with malignant IPMN status independent of selected variables. To assess the accuracy and clinical utility of candidate miRNAs in differentiating between malignant and benign IPMNs, ROC curves were constructed using the normalized miRNA count values and PC1, with pathological diagnosis as the gold standard.

Exploring paired tissue and circulating miRNA expression: Since a positive correlation between tissue and plasma miRNAs may be indicative of a functional relationship, we identified 12 IPMN cases (4 low-grade, 8 high-grade) with plasma successfully analyzed in the current study who had matching tumor tissue that underwent genome-wide miRNA profiling as part of a previous investigation using qRT-PCR technology (54). We used Spearman correlations to evaluate the relationship between mean abundance of each miRNA in pre-operative plasma compared to paired tissue.

All statistical analyses were performed using SAS version 9.4 and R version 3.11. To visualize miRNA expression patterns, we generated heatmaps and performed unsupervised, hierarchical clustering.

Example 2—Plasma MicroRNAs as Novel Biomarkers of Disease for Patients with Intraductal Papillary Mucinous Neoplasms of the Pancreas Pancreatic ductal adenocarcinoma (PDAC) is the fourth leading cause of cancer deaths in the United States, with a five-year survival rate of only 6% (51). Approximately 85% of cases present with metastasis, which can be partly explained by a lack of sensitive and specific methods to detect disease at an early, operable stage (51). Based on a two-decade window of opportunity for early detection efforts in PDAC (6), an emerging paradigm is that the detection and treatment of noninvasive precursor lesions may offer the greatest hope in reducing PDAC morbidity and mortality. Three noninvasive PDAC precursor lesions ('precancers') that progress from low- and moderate-grade dysplasia to high-grade dysplasia and invasive carcinoma have been identified: pancreatic intraepithelial neoplasia (PanIN), mucinous cystic neoplasms (MCNs), and intraductal papillary mucinous neoplasms (IPMNs) (52,2). PanINs are microscopic lesions, while MCNs and IPMNs are macroscopic cysts accounting for over half of the 150,000 asymptomatic pancreatic cysts detected incidentally in the general population each year by imaging (4). IPMNs and PanINs have also been detected in those at high genetic risk for PDAC (53). Once detected, invasive procedures such as endoscopic ultrasounds are often performed to assess the degree of dysplasia, but imaging features and biomarkers obtained from such procedures do not reliably predict disease severity pre-operatively (2). Less invasive approaches are needed to aid in IPMN diagnosis and treatment and to prevent progression to malignancy.

miRNAs are non-coding RNAs that regulate nearly one-third of all protein-coding genes and promote carcinogenesis by regulating tumor suppressors and oncogenes or serving these functions themselves (15). miRNAs are excellent candidate biomarkers of early disease because of their tissue-specific expression patterns (15), their remarkable stability in tissue (16) and biofluids (46) due to their small size and protection from endogenous RNase activity, and their ability to regulate hundreds of genes and biological pathways (15). Recent studies by our group (54) and others (5,29,44) have evaluated genome-wide miRNA expression in IPMN tissue, and provide data to suggest that key miRNAs may reliably differentiate low-risk/benign IPMNs (i.e., low- and moderate-grade) that can be monitored from high-risk/malignant IPMNs (i.e., high-grade and invasive) that should be surgically resected. These tissue-based findings combined with discoveries that miRNAs can be readily and reliably detected in systemic circulation (46,17) raise the possibility that a minimally-invasive, cost-effective test that capitalizes on blood levels of miRNAs may be able to differentiate between individuals with IPMNs and non-diseased controls and between malignant and benign IPMNs.

Although several studies (55-57) have evaluated miRNA expression in plasma, serum, or whole blood of PDAC patients and healthy controls, the implications for early detection were limited because most cases had locally advanced or metastatic disease. Of two recent studies (48, 58) that focused on evaluating blood-based genome-wide miRNA expression in early-stage PDAC patients versus controls, one (48) included pre-operative serum from patients with IPMNs (N=20; 4 low-grade; 16 moderate-/high-grade). Li et al. (48) measured 735 miRNAs by qRT-PCR using Taqman MicroRNA Arrays, and found that serum levels of miR-1290 were significantly higher among the 20 patients with IPMNs compared to healthy controls (area underneath the curve (AUC)=0.76 (95% confidence interval (CI): 0.61-0.91)). Although promising, these findings warrant replication in a larger, independent population. Additionally, since most miRNAs are present in low quantities in blood, PCR-based methods are limited in their ability to accurately detect and quantify miRNA levels and can require pre-amplification which may compromise measurement reliability (57).

The primary objective of the current study was to determine the feasibility of measuring the abundance of 800 miRNAs in archived plasma obtained pre-operatively from individuals newly-diagnosed with IPMNs and disease-free controls using a novel digital amplification-free quantification and comparison method called NCOUNTER™ technology (Nanostring, Inc., Seattle, Wash.) (59). Through an exploratory analysis, we then sought to discover a panel of circulating miRNAs that may a) differentiate between patients with IPMNs and non-diseased controls, b) distinguish malignant from benign IPMNs, and/or c) reflect the paired tumor miRNA expression profile. To our knowledge, this is the first study to conduct genome-wide profiling of circulating miRNAs exclusively among patients with cancer precursors using novel digital technology.

Development of a minimally invasive blood-based assay for the early detection and management of pancreatic cancer precursors such as intraductal papillary mucinous neoplasms (IPMNs) is urgently needed to reduce the risks associated with invasive diagnostic approaches and to help prevent progression to incurable pancreatic malignancy. Based on the hypothesis that differentially expressed microRNAs (miRNA) may be shed from IPMN tissues and detected in circulation, the inventors conducted the first study that aimed to identify plasma miRNAs that could distinguish patients with IPMNs from healthy controls. Using novel NCOUNTER™ technology to evaluate 800 miRNAs in archived plasma, the inventors show that a signature containing 30 miRNAs distinguished 42 IPMN cases from 24 healthy controls (area underneath the curve (AUC)=74.4 (95% CI: 62.3-86.5, p=0.002)). The signature contained novel miRNAs and miRNAs previously implicated in pancreatic carcinogenesis that had 2 to 4-fold higher expression in cases than controls. The inventors also generated a 5-miRNA signature that discriminated between 21 malignant and 21 benign IPMNs (AUC=73.2 (95% CI: 57.6-73.2, p=0.005)), and provide data to suggest that paired plasma and tissue samples from patients with IPMNs can have distinct miRNA expression profiles. These findings demonstrate the feasibility of using new cost-effective digital technology to reliably develop a minimally-invasive assay to measure plasma miRNA expression and aid in IPMN management.

A. Study Population

Pre-operative plasma samples were evaluated for 44 IPMN cases (5 low-grade, 18 moderate-grade, 13 high-grade, and 8 invasive) and 25 non-diseased controls that were frequency-matched to cases on age-group and gender. Three samples (2 from cases and 1 from a control) were excluded prior to normalization and statistical analysis due to presumed cellular contamination characterized by ribosomal RNA bands or high mRNA counts, leaving a total of 66 subjects (42 pathologically-confirmed IPMN cases, 24 controls) for analysis. Characteristics of the analyzed cases and controls are shown in Table 7. Cases and controls were well-matched on age (mean age: 69.0 vs 69.1). Most subjects were white, non-Hispanic, and the majority were current or previous smokers without a family history of PDAC. The distribution of low-, moderate-, high-grade, and invasive IPMN cases represented in this study was 9.5%, 40.5%, 31%, and 19%, respectively.

TABLE 7

Characteristics of the Study Population (N = 66).

| Variable | IPMN cases (n = 42) | Healthy controls (n = 24) |
|---|---|---|
| Age at diagnosis/interview, mean (SD)(yrs) | 69.0 (10.7) | 69.1 (9.6) |
| Gender, male:female, n (%) | 19:23 (45:55) | 12:12 (50:50) |
| Race, n (%) | | |
| White, Non-Hispanic | 37 (88) | 24 (100) |
| Other | 5 (12) | 0 (0) |
| Family history of pancreatic cancer, n (%) | | |
| Yes | 4 (17) | 1 (4) |
| No | 15 (83) | 23 (96) |
| Ever Smoker, n (%) | | |
| Yes | 21 (50) | 11 (46) |
| No | 21 (50) | 3 (13) |
| Unknown | 0 (0) | 10 (42) |
| IPMN Grade, n (%) | | |
| Low | 4 (9.5) | — |
| Moderate | 17 (40.5) | — |
| High | 13 (31) | — |
| Invasive | 8 (19) | — |

Data represent counts (percentages) unless otherwise indicated. Counts may not add up to the total due to missing values, and percentages may not equal 100 due to rounding.

B. Exploratory Analysis of Circulating miRNAs in IPMNS Versus Non-Diseased Controls A total of 558 of the 800 miRNAs evaluated (69.8%) had more than 80% of signals below background and were excluded, leaving 242 miRNAs for normalization and statistical analysis. This proportion of detectable circulating miRNAs is comparable or better than that of other studies (58,72-74) and demonstrates the NCOUNTER platform's ability to detect a sizeable number of miRNAs using archived plasma samples. No difference in the frequency or the amount of hemolysis as measured spectrophotometrically or by hemolysis-related miRNA analysis was observed in the case versus control samples.

Figure 10A:
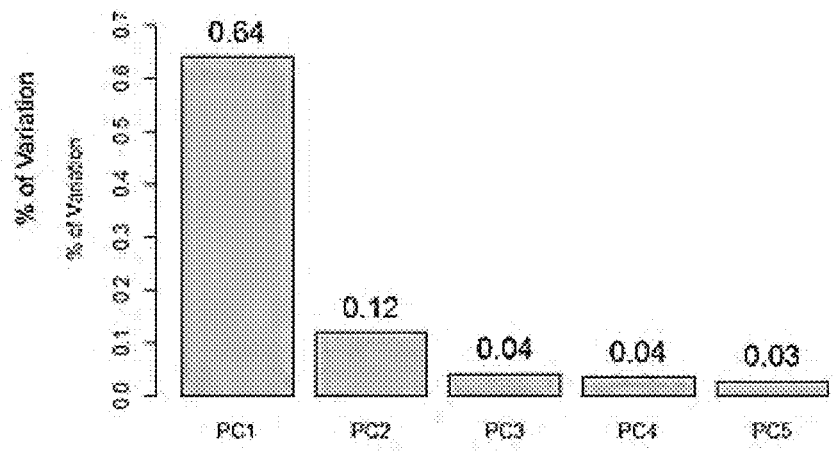
FIGS. 10A-10C. A 30-miRNA signature discriminates IPMN Cases (N=42) from Healthy Controls (N=24).
Figure 10B:
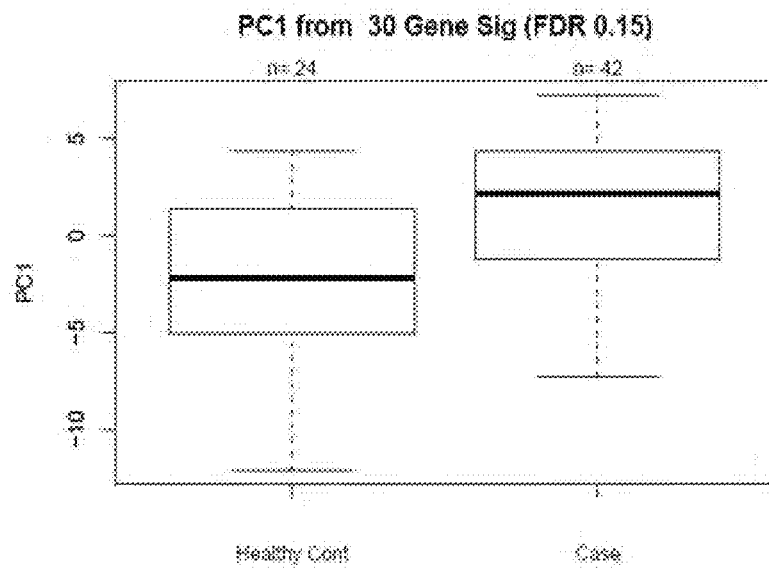
Figure 10C:
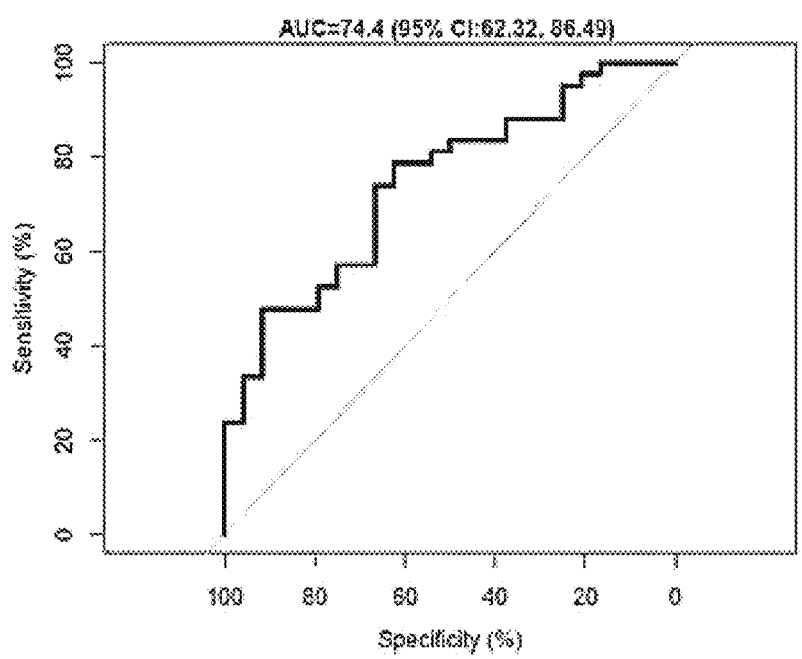
Figure 11A:
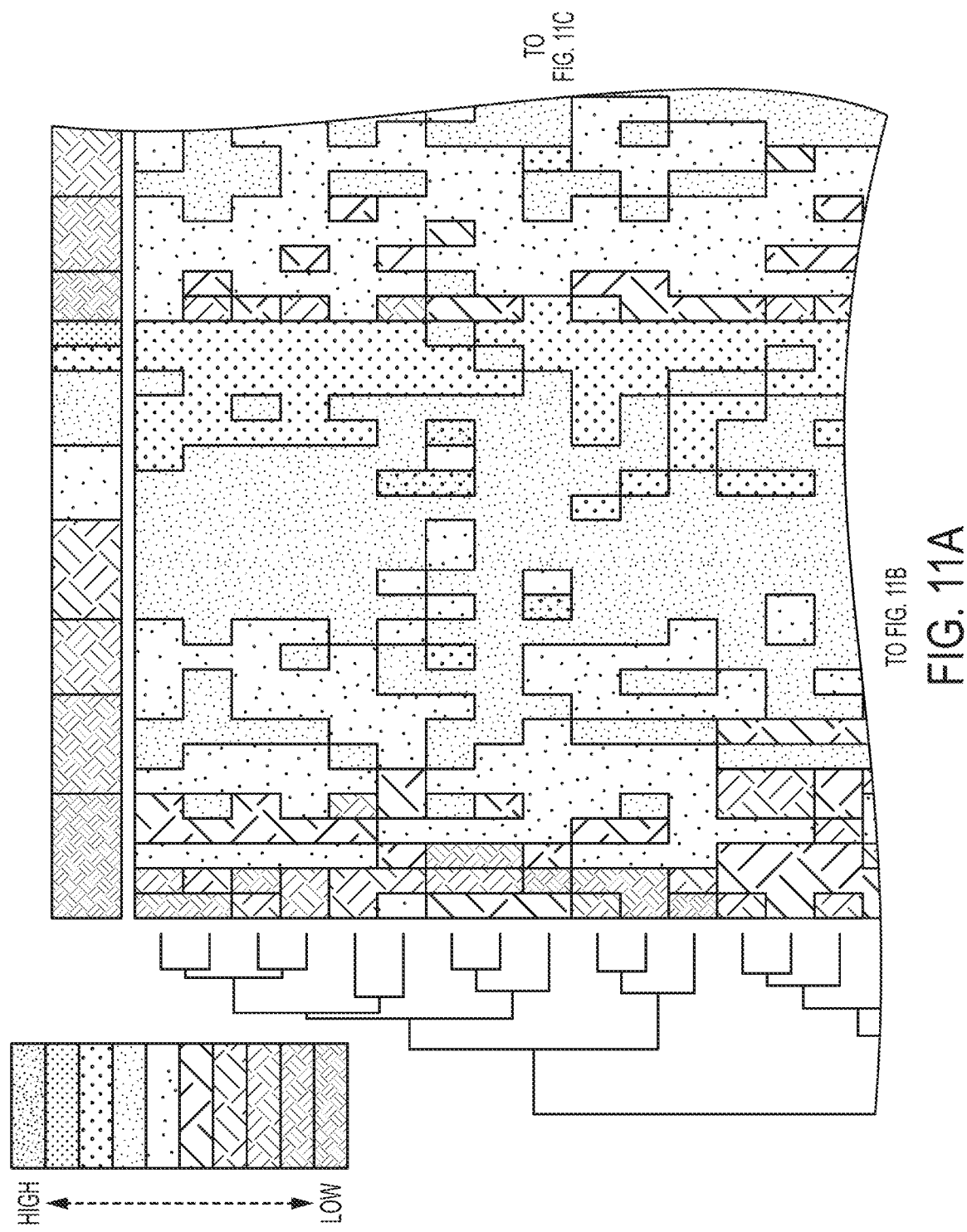
FIGS. 11A-11D. Heatmap of the 30-miRNA signature in IPMN cases and non-diseased controls.
Figure 11B:
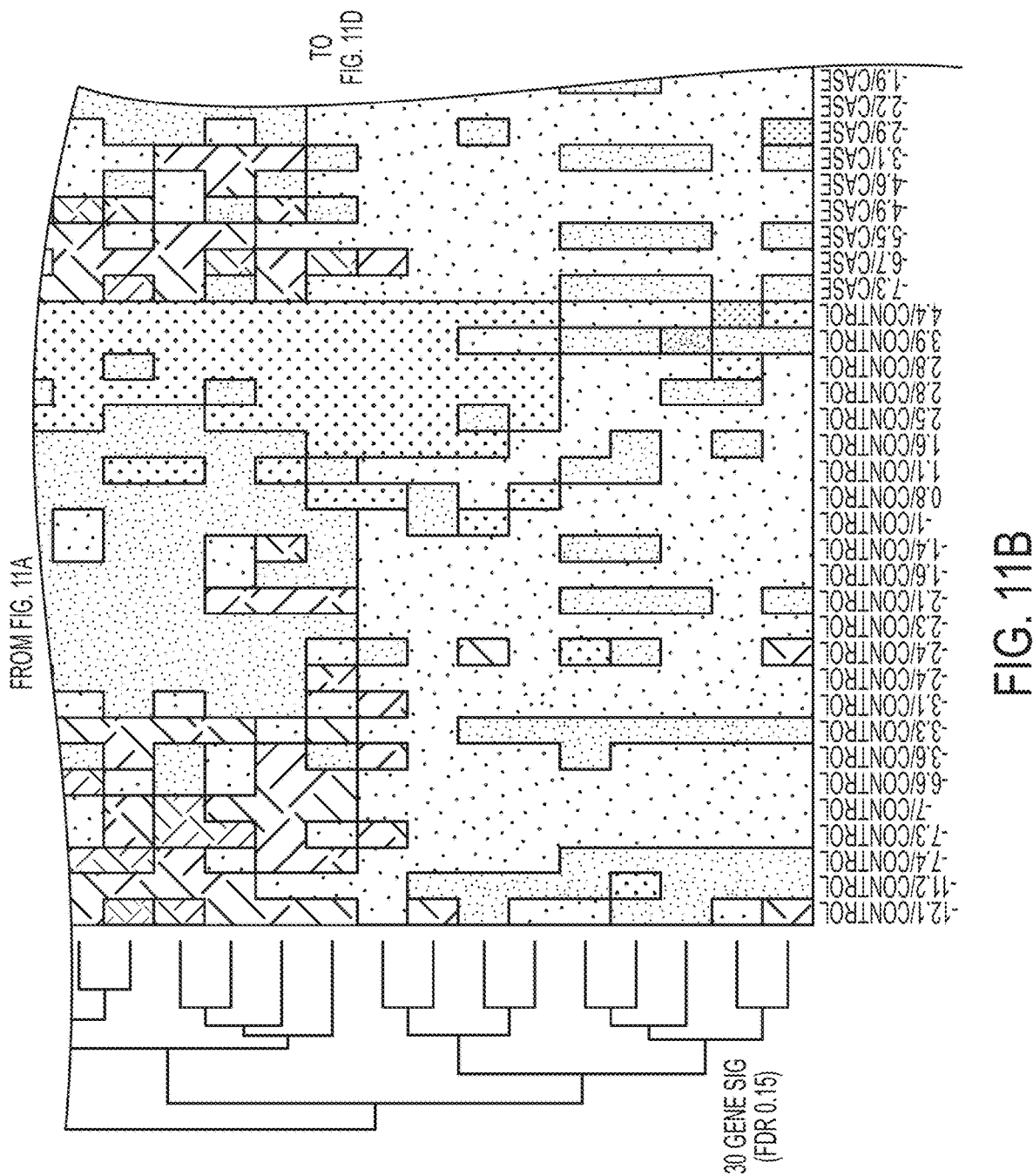
Figure 11C:
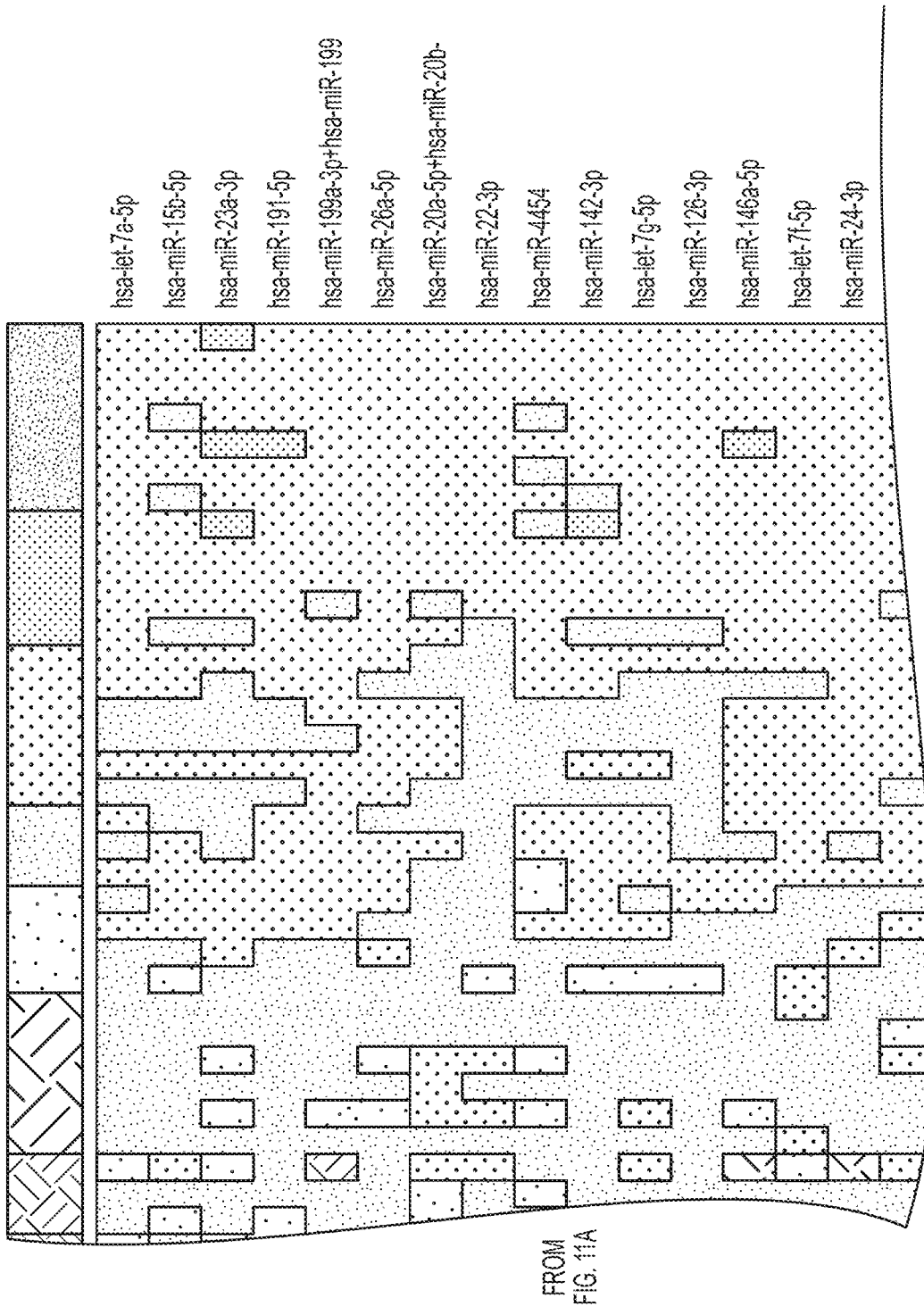
Figure 11D:
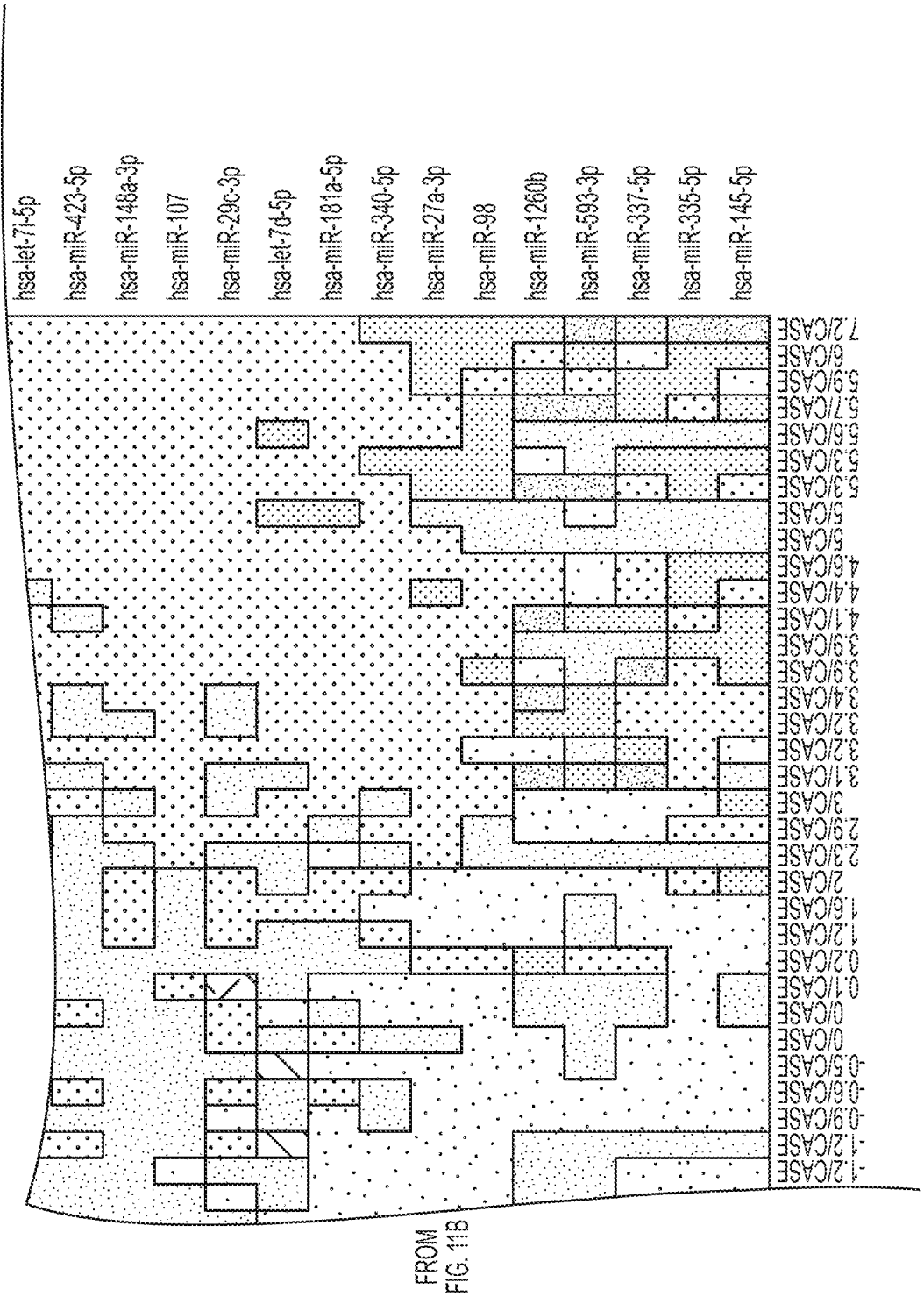
Figure 12A:
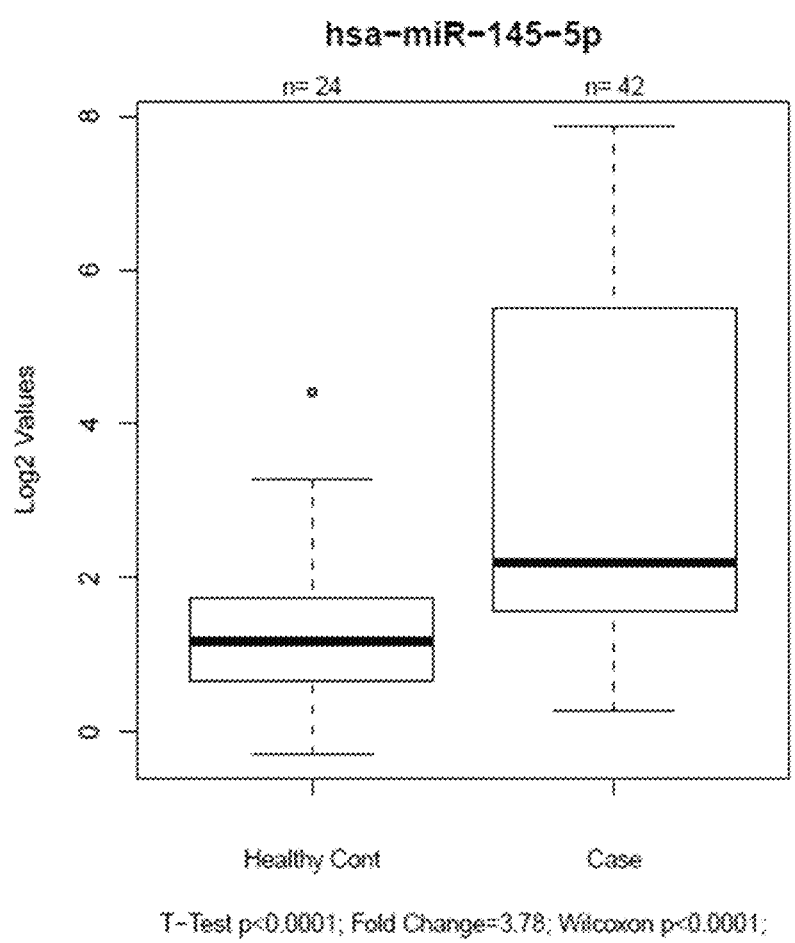
FIGS. 12A-12B. miR-145-5p expression differentiates between cases and non-diseased controls.
Figure 12B:
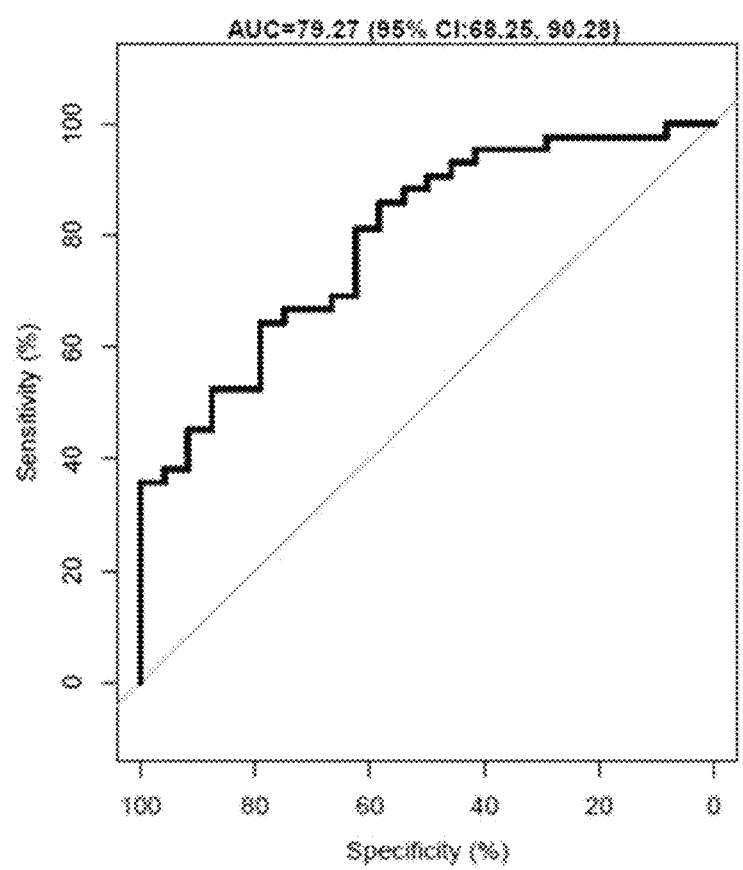
Figure 13A:
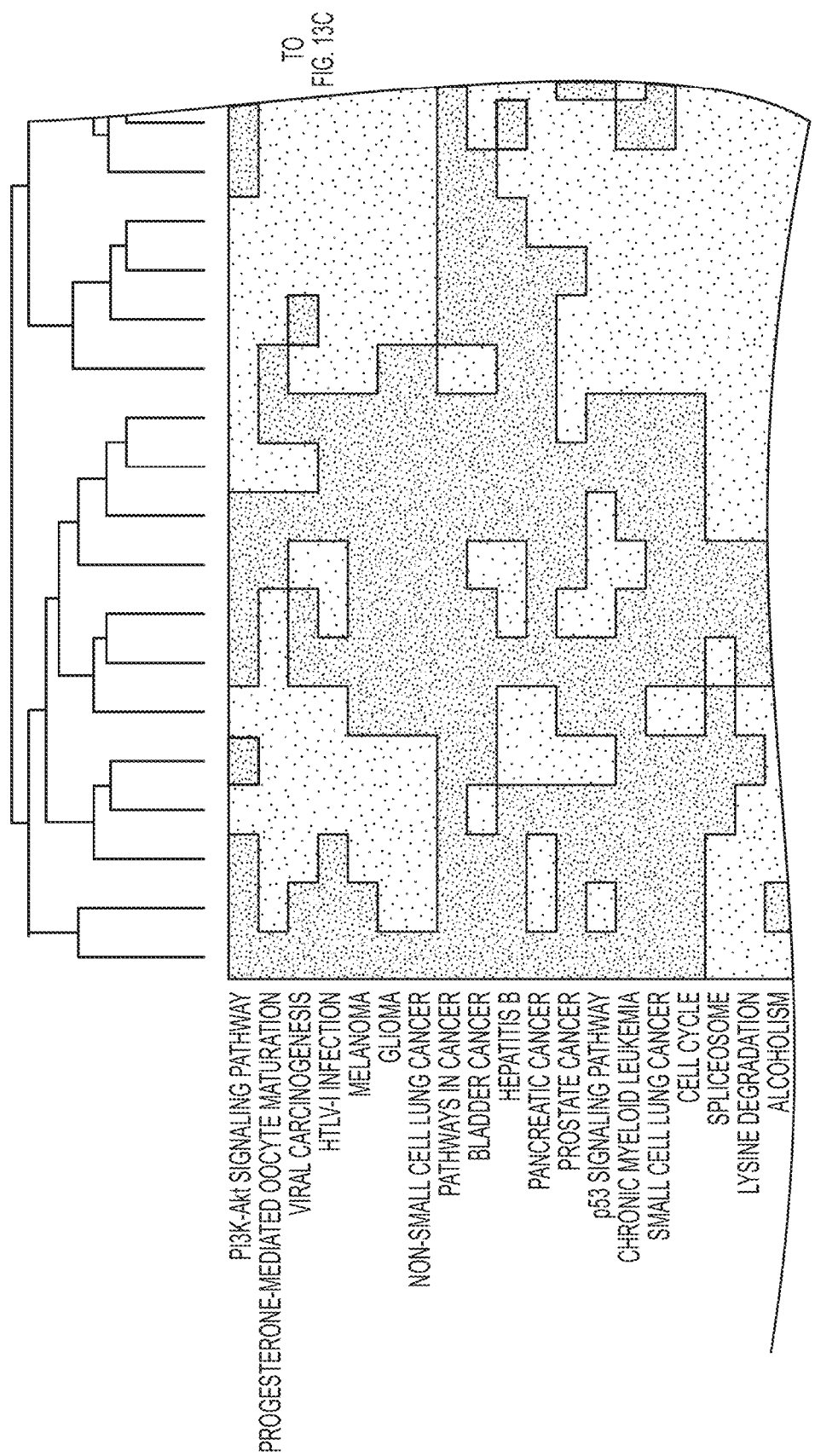
Figure 13B:
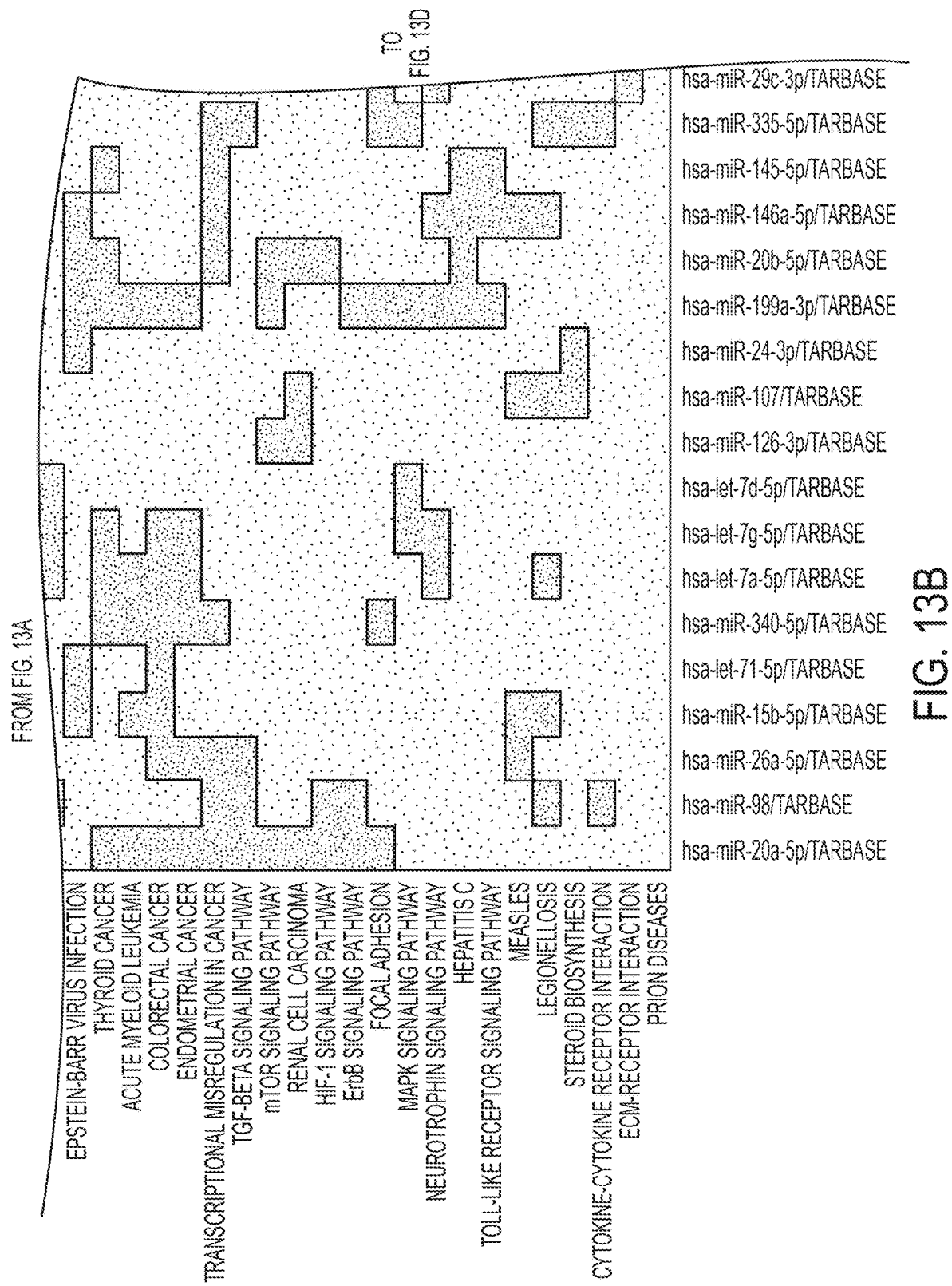

After technical normalization with spike-in oligos and biological normalization with the most invariant miRNAs in the dataset (miR-378, miR-579, miR-30e-5p, and miR-570-3p), 30 miRNAs differentiated between IPMN cases and controls using an FDR<0.15. The 30 miRNAs include: let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199a-3p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, and miR-98. The candidate miRNAs had 2.09-4.32 fold higher expression as defined by mean normalized counts in the plasma of cases as opposed to controls (Table 8). The circulating miRNA that was most significantly associated with IPMN case status was miR-145-5p (t-test P=$8.6 \times 10^{-5}$), with expression levels 3.78 fold higher in cases than controls and an AUC value of 0.79 (95% CI: 69.3-90.3) in classifying between IPMNs and healthy controls (Table 8; FIGS. 12A and 12B).

overall expression of PC1 was higher in cases as compared to controls (p=0.002, FIG. 10B). Moreover, the continuous PC1 score for the 30-miRNA signature showed a significant association with IPMN status (odds ratio (OR) 95% CI: =1.23 (1.07-1.41), p=0.003) and had an AUC value of 74.4 (95% CI: 62.3-86.5) in discriminating between IPMN patients and healthy controls (FIG. 10C). A heatmap of gene expression for the 30 miRNA signature in our cohort is displayed in FIGS. 11A-11D. Pathway enrichment analysis revealed numerous pathways that are predicted to be regulated by the 30 miRNA IPMN-risk signature (FIGS. 13A-13D), with 'Pathways in Cancer' and 'p53 signaling' comprising the most significantly predicted pathways with p=$1.3 \times 10^{-26}$ and p=$1.2 \times 10^{-24}$, respectively.

C. Exploratory Analysis of Circulating miRNAs in Malignant Versus Benign IPMNs

For exploratory purposes, we evaluated the ability of the 30-miRNA signature represented by PC1 to discriminate between the 21 malignant and 21 benign IPMN cases. We observed that the signature did not accurately differentiate between malignant and benign IPMNs (AUC=60.8 (95% CI: 42.5-79.1)). However, after performing LIMMA and PCA analysis exclusively on the 42 IPMN cases, circulating

TABLE 8

The top 30 miRNAs deregulated in plasma of IPMN cases versus non-diseased controls

| miRNA ID | Mean Normalized Counts Cases (n = 42) | Mean Normalized Counts Controls (n = 24) | Fold-Change | P | False Discovery Rate | AUC (95% CI) |
|---|---|---|---|---|---|---|
| hsa-miR-145-5p | 3.26 | 1.34 | 3.78 | 8.61E−05 | 0.0208 | 79.3 (68.3, 90.3) |
| hsa-miR-4454 | 10.58 | 9.46 | 2.18 | 0.0018 | 0.1043 | 72.4 (59.6, 85.2) |
| hsa-let-7f-5p | 8.27 | 6.38 | 3.69 | 0.0028 | 0.1043 | 73.8 (62.0, 85.6) |
| hsa-miR-146a-5p | 8.55 | 6.55 | 4.00 | 0.0032 | 0.1043 | 72.4 (60.2, 84.6) |
| hsa-let-7d-5p | 7.33 | 5.42 | 3.75 | 0.0043 | 0.1043 | 69.1 (55.7, 82.4) |
| hsa-let-7a-5p | 11.43 | 9.83 | 3.05 | 0.0044 | 0.1043 | 68.6 (55.2, 81.9) |
| hsa-miR-142-3p | 12.71 | 11.29 | 2.68 | 0.0060 | 0.1043 | 67.2 (53.3, 81.0) |
| hsa-miR-423-5p | 8.62 | 7.04 | 2.99 | 0.0061 | 0.1043 | 69.4 (56.2, 82.7) |
| hsa-miR-22-3p | 10.06 | 8.93 | 2.18 | 0.0072 | 0.1043 | 68.8 (55.8, 81.7) |
| hsa-miR-107 | 7.64 | 5.84 | 3.48 | 0.0073 | 0.1043 | 72.3 (59.3, 85.4) |
| hsa-miR-29c-3p | 6.97 | 5.11 | 3.63 | 0.0076 | 0.1043 | 67.4 (53.6, 81.1) |
| hsa-miR-148a-3p | 8.23 | 6.50 | 3.31 | 0.0078 | 0.1043 | 70.8 (57.8, 83.9) |
| hsa-miR-340-5p | 5.28 | 3.18 | 4.32 | 0.0079 | 0.1043 | 70.8 (57.5, 84.2) |
| hsa-miR-181a-5p | 5.36 | 3.34 | 4.06 | 0.0079 | 0.1043 | 69.6 (56.6, 82.7) |
| hsa-miR-335-5p | 3.44 | 1.92 | 2.87 | 0.0083 | 0.1043 | 69.4 (56.3, 82.6) |
| hsa-let-7i-5p | 8.79 | 7.31 | 2.80 | 0.0092 | 0.1043 | 71.0 (58.3, 83.7) |
| hsa-miR-337-5p | 3.19 | 1.71 | 2.79 | 0.0092 | 0.1043 | 71.4 (58.2, 84.7) |
| hsa-miR-1260b | 3.28 | 1.63 | 3.15 | 0.0093 | 0.1043 | 67.9 (54.6, 81.1) |
| hsa-miR-593-3p | 2.46 | 1.40 | 2.09 | 0.0097 | 0.1043 | 68.7 (55.2, 82.1) |
| hsa-miR-27a-3p | 4.29 | 2.61 | 3.20 | 0.0097 | 0.1043 | 68.8 (55.3, 82.2) |
| hsa-let-7g-5p | 11.95 | 10.70 | 2.38 | 0.0099 | 0.1043 | 68.5 (55.4, 81.5) |
| hsa-miR-191-5p | 10.56 | 9.29 | 2.40 | 0.0100 | 0.1043 | 68.2 (54.9, 81.4) |
| hsa-miR-24-3p | 8.15 | 6.21 | 3.83 | 0.0100 | 0.1043 | 69.4 (56.3, 82.4) |
| hsa-miR-20a-5p + hsa-miR-20b-5p | 10.36 | 9.15 | 2.30 | 0.0103 | 0.1043 | 68.1 (54.9, 81.2) |
| hsa-miR-26a-5p | 10.23 | 8.91 | 2.50 | 0.0114 | 0.1100 | 72.4 (60.2, 84.6) |
| hsa-miR-23a-3p | 11.16 | 10.05 | 2.16 | 0.0130 | 0.1206 | 66.7 (53.2, 80.2) |
| hsa-miR-199a-3p + hsa-miR-199b-3p | 10.53 | 8.95 | 2.99 | 0.0150 | 0.1344 | 69.5 (56.5, 82.6) |
| hsa-miR-126-3p | 13.23 | 11.90 | 2.51 | 0.0168 | 0.1406 | 65.8 (52.0, 79.5) |
| hsa-miR-98 | 4.12 | 2.51 | 3.05 | 0.0174 | 0.1406 | 67.4 (54.0, 80.8) |
| hsa-miR-15b-5p | 11.24 | 9.83 | 2.65 | 0.0174 | 0.1406 | 65.8 (52.3, 79.3) |

Figure 14A:
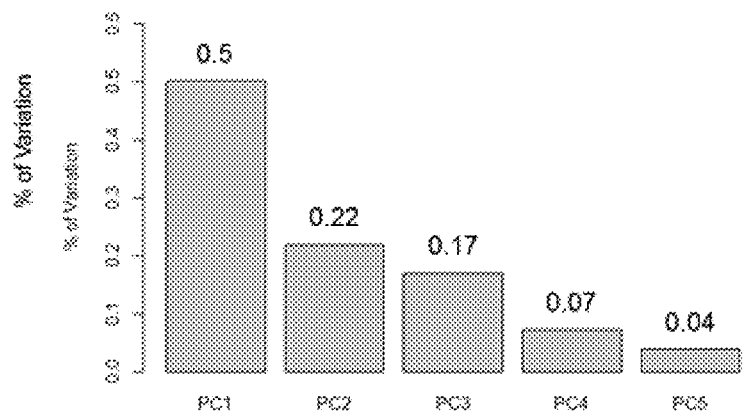
FIGS. 14A-14C.
Figure 14B:
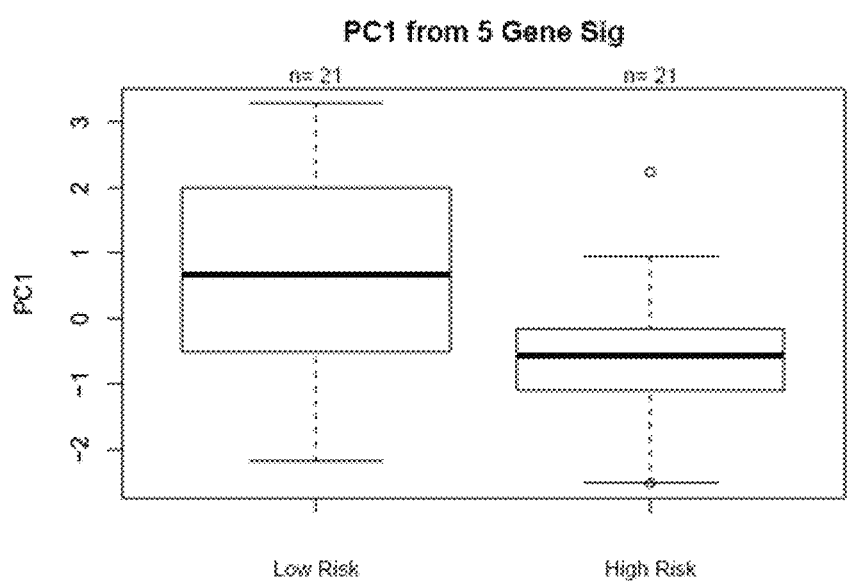
Figure 14C:
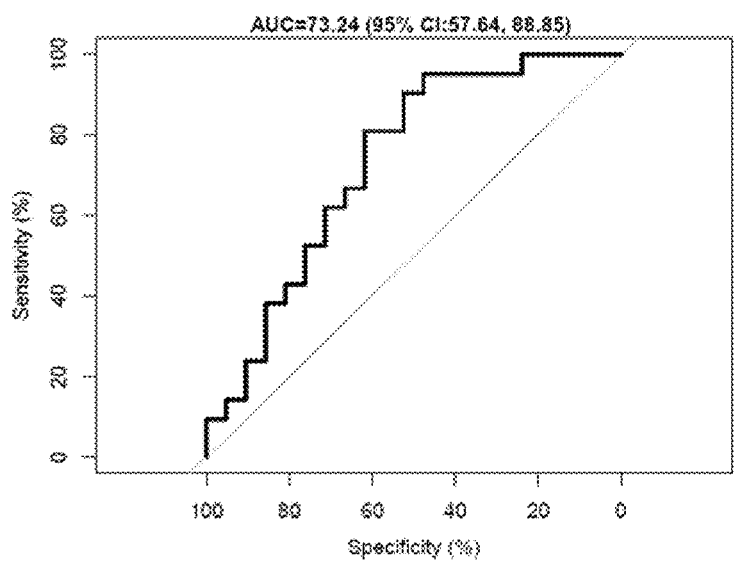

Abbreviations:
AUC = Area underneath the curve;
CI = confidence interval
Comparisons conducted with t-tests The 30 miRNA IPMN-risk signature was analyzed using PCA to evaluate the percent of variability and loading coefficients by PC1 (i.e. the IPMN-risk score). PC1 explained 64% of the variability, suggesting it represents the 30 miRNA IPMN-risk signature well (FIG. 10A). The levels of five miRNAs (miR-200a-3p, miR-1185-5p, miR-33a-5p, miR-574-3p, and miR-663b) discriminated between the malignant and benign IPMN groups (p<0.05) (Table 9). The 5 miRNA IPMN-risk signature was analyzed using PCA to evaluate the percent of variability and loading coefficients by PC1. PC1 explained 50% of the variability (FIG. 14A). The overall expression of PC1 was higher in benign compared to malignant IPMNs (p=0.005, FIG. 14B). Moreover, the continuous PC1 score for the 5-miRNA signature showed a significant association with malignant status (OR (95% CI): =0.36 (0.16, 0.83), p=0.017) and had an AUC value of 73.2 (95% CI: 57.6-88.9) in discriminating between groups (FIG. 14C). Multivariable logistic regression revealed that the PC1 score for the 5-miRNA signature was not independently associated with malignant status after adjustment for main duct involvement (p=0.008), a predictor of malignant potential that can be detected by imaging.

TABLE 9

MiRNA expression in Malignant (N = 21) versus Benign (N = 21) IPMN cases

| miRNA ID | Mean expression malignant cases | Mean expression benign cases | Fold-Change | P | False Discovery Rate | AUC (95% CI) |
|---|---|---|---|---|---|---|
| hsa-miR-200a-3p | 1.615771833 | 2.966035816 | 2.549587734 | 0.030625 | 0.942422398 | 63.49 (45.74, 81.24) |
| hsa-miR-1185-5p | 3.30508802 | 4.663054049 | 2.563235492 | 0.0362 | 0.942422398 | 66.67 (49.71, 83.62) |
| hsa-miR-33a-5p | 4.197148768 | 5.760001269 | 2.954374061 | 0.036233 | 0.942422398 | 70.29 (53.84, 86.75) |
| hsa-miR-574-3p | 2.684391746 | 4.089466711 | 2.648315428 | 0.042473 | 0.942422398 | 67.57 (50.33, 84.82) |
| hsa-miR-663b | 1.345295736 | 2.559839402 | 2.320673668 | 0.045826 | 0.942422398 | 45.58 (27.33, 63.83) |
| hsa-miR-99b-5p | 3.216612767 | 4.606655552 | 2.620864532 | 0.050763 | 0.942422398 | 63.04 (45.02, 81.06) |
| hsa-miR-626 | 2.242417221 | 3.5535875 | 2.481427458 | 0.051473 | 0.942422398 | 64.4 (46.86, 81.93) |
| hsa-miR-431-5p | 2.277640545 | 3.44308567 | 2.243024107 | 0.052351 | 0.942422398 | 65.76 (47.89, 83.63) |
| hsa-miR-548am-3p | 2.811372049 | 1.847526035 | 1.950502724 | 0.063424 | 0.942422398 | 74.15 (58.88, 89.42) |
| hsa-miR-766-3p | 2.246317884 | 3.397633119 | 2.221162949 | 0.066287 | 0.942422398 | 58.5 (40.06, 76.95) |
| hsa-miR-325 | 1.761160582 | 3.021185483 | 2.394998747 | 0.068005 | 0.942422398 | 62.13 (44.4, 79.86) |
| hsa-miR-340-5p | 4.450771351 | 6.128155372 | 3.198474588 | 0.071935 | 0.942422398 | 62.59 (44.37, 80.8) |
| hsa-miR-423-3p | 3.497204436 | 4.824352297 | 2.509061549 | 0.072879 | 0.942422398 | 63.04 (44.7, 81.38) |
| hsa-miR-125a-5p | 4.153821563 | 5.835689051 | 3.208429956 | 0.073317 | 0.942422398 | 61.22 (42.21, 80.24) |
| hsa-miR-891b | 1.40412578 | 2.38490016 | 1.973524433 | 0.075251 | 0.942422398 | 57.14 (38.57, 75.72) |
| hsa-miR-4443 | 5.471587884 | 7.553436401 | 4.233493039 | 0.075369 | 0.942422398 | 67.12 (49.84, 84.4) |
| hsa-miR-152 | 2.668170778 | 3.773973482 | 2.152185907 | 0.088186 | 0.942422398 | 59.86 (41.51, 78.22) |
| hsa-miR-337-3p | 3.289640753 | 4.542330799 | 2.382853153 | 0.103 | 0.942422398 | 59.18 (40.73, 77.64) |
| hsa-miR-432-5p | 2.329661787 | 3.345909559 | 2.022651507 | 0.10316 | 0.942422398 | 59.41 (40.65, 78.17) |
| hsa-miR-518b | 7.553215211 | 8.51841713 | 1.95233675 | 0.104286 | 0.942422398 | 72.79 (57.22, 88.36) |
| hsa-miR-151a-3p | 6.525286111 | 7.785322099 | 2.395017152 | 0.104296 | 0.942422398 | 63.95 (46.45, 81.44) |
| hsa-miR-301a-3p | 4.749355407 | 6.040712701 | 2.447582168 | 0.104688 | 0.942422398 | 62.81 (45.38, 80.24) |
| hsa-miR-324-5p | 3.622046418 | 4.984271817 | 2.570814295 | 0.110909 | 0.942422398 | 60.32 (41.61, 79.02) |
| hsa-miR-363-3p | 3.658756844 | 5.233824249 | 2.97949413 | 0.111376 | 0.942422398 | 60.54 (42.13, 78.96) |
| hsa-miR-28-5p | 5.277202334 | 6.311696999 | 2.048396026 | 0.116503 | 0.942422398 | 62.81 (45.44, 80.18) |
| hsa-miR-590-5p | 7.012386539 | 7.758008003 | 1.676696378 | 0.12366 | 0.942422398 | 62.81 (45.54, 80.08) |
| hsa-miR-23b-3p | 4.032710365 | 5.324122578 | 2.447675344 | 0.12729 | 0.942422398 | 59.64 (41.26, 78.02) |
| hsa-miR-656 | 3.738385956 | 4.795142843 | 2.080249954 | 0.13051 | 0.942422398 | 62.81 (45.5, 80.12) |
| hsa-miR-27b-3p | 6.358658637 | 7.750298731 | 2.623767882 | 0.132811 | 0.942422398 | 64.63 (47.4, 81.85) |
| hsa-miR-450a-5p | 2.829803981 | 3.830108875 | 2.000422718 | 0.142842 | 0.942422398 | 59.18 (40.98, 77.39) |
| hsa-miR-323a-3p | 3.001192263 | 4.227602918 | 2.339841257 | 0.143145 | 0.942422398 | 61.68 (43.8, 79.56) |
| hsa-miR-374b-5p | 5.909592739 | 7.214609192 | 2.470865452 | 0.154409 | 0.942422398 | 65.31 (48.01, 82.6) |
| hsa-miR-769-5p | 5.902090162 | 6.717782712 | 1.760142886 | 0.154848 | 0.942422398 | 65.76 (48.21, 83.31) |
| hsa-miR-598 | 8.033655579 | 8.686225219 | 1.571965593 | 0.156413 | 0.942422398 | 63.04 (44.77, 81.31) |
| hsa-let-7e-5p | 2.649924375 | 3.686594428 | 2.051487057 | 0.156889 | 0.942422398 | 56.92 (38.69, 75.14) |
| hsa-miR-1246 | 7.698808917 | 6.065808623 | 3.101573457 | 0.166295 | 0.942422398 | 65.08 (47.96, 82.2) |
| hsa-miR-1183 | 6.430538854 | 7.500899759 | 2.099958628 | 0.167408 | 0.942422398 | 64.17 (46.73, 81.61) |
| hsa-miR-503 | 2.542922227 | 3.5421607 | 1.998944578 | 0.168895 | 0.942422398 | 55.56 (36.82, 74.3) |
| hsa-miR-145-5p | 2.809230013 | 3.704919727 | 1.860499127 | 0.170114 | 0.942422398 | 57.37 (38.54, 76.2) |
| hsa-miR-520f | 14.74582444 | 14.21943187 | 1.440323193 | 0.171418 | 0.942422398 | 63.95 (46.92, 80.98) |
| hsa-miR-199a-3p + hsa-miR-199b-3p | 10.07926225 | 10.98480276 | 1.873246171 | 0.172369 | 0.942422398 | 61.9 (44.3, 79.51) |
| hsa-miR-409-3p | 3.530767091 | 4.592448331 | 2.087362605 | 0.177634 | 0.942422398 | 56.69 (38.28, 75.1) |
| hsa-miR-107 | 7.149547583 | 8.138766822 | 1.985110393 | 0.178718 | 0.942422398 | 66.21 (49.19, 83.24) |
| hsa-miR-181a-5p | 4.746250169 | 5.97538226 | 2.344259194 | 0.179448 | 0.942422398 | 61 (42.21, 79.79) |
| hsa-miR-18a-5p | 6.321189577 | 7.167105787 | 1.79740586 | 0.180714 | 0.942422398 | 62.81 (45.49, 80.13) |
| hsa-miR-219-5p | 3.846317526 | 4.885776949 | 2.05545733 | 0.184777 | 0.942422398 | 64.17 (46.72, 81.62) |
| hsa-miR-761 | 5.444189668 | 6.49773429 | 2.07562328 | 0.186382 | 0.942422398 | 64.85 (47.4, 82.3) |
| hsa-miR-136-5p | 2.269815944 | 3.233955453 | 1.950899567 | 0.191013 | 0.942422398 | 52.61 (33.89, 71.33) |
| hsa-miR-361-5p | 5.297989314 | 6.547116924 | 2.37697645 | 0.197897 | 0.942422398 | 58.96 (40.75, 77.16) |
| hsa-miR-378a-3p + hsa-miR-378i | 2.887098667 | 2.164701522 | 1.649921225 | 0.199155 | 0.942422398 | 67.12 (50.33, 83.91) |
| hsa-miR-199a-5p | 7.446858231 | 8.482077163 | 2.049424627 | 0.206348 | 0.942422398 | 64.63 (47.49, 81.76) |
| hsa-miR-376a-3p | 5.254349349 | 6.435834206 | 2.268100956 | 0.208832 | 0.942422398 | 60.09 (42.32, 77.86) |
| hsa-miR-335-5p | 2.963842605 | 3.910833708 | 1.927847727 | 0.209464 | 0.942422398 | 56.92 (38.63, 75.2) |
| hsa-miR-641 | 2.383608366 | 1.812532861 | 1.48563067 | 0.213825 | 0.942422398 | 70.75 (54.31, 87.19) |
| hsa-let-7d-5p | 6.875278429 | 7.782075876 | 1.874878944 | 0.216245 | 0.942422398 | 64.4 (46.82, 81.98) |
| hsa-miR-515-5p | 1.771671055 | 2.492186146 | 1.64777024 | 0.219054 | 0.942422398 | 46.49 (27.85, 65.12) |
| hsa-miR-24-3p | 7.644710385 | 8.651529824 | 2.009476128 | 0.221976 | 0.942422398 | 63.27 (45.91, 80.62) |
| hsa-miR-548a-3p | 2.597733633 | 3.481908316 | 1.845708452 | 0.228709 | 0.954268456 | 58.28 (40.07, 76.48) |
| hsa-miR-720 | 6.097764926 | 7.022095499 | 1.897803436 | 0.233878 | 0.95929431 | 61.9 (44.47, 79.34) |
| hsa-miR-125b-5p | 6.211103968 | 5.302946467 | 1.876647258 | 0.245976 | 0.975564671 | 58.96 (40.7, 77.22) |
| hsa-miR-10a-5p | 2.299699617 | 1.738028042 | 1.475978366 | 0.24834 | 0.975564671 | 64.17 (46.8, 81.54) |
| hsa-miR-4454 | 10.37523516 | 10.78558888 | 1.32901162 | 0.250944 | 0.975564671 | 62.59 (45, 80.17) |
| hsa-miR-376c | 3.692307708 | 4.81424283 | 2.176387008 | 0.257087 | 0.975564671 | 54.42 (36.01, 72.83) |
| hsa-miR-370 | 3.122315202 | 3.998907771 | 1.836033738 | 0.258001 | 0.975564671 | 60.77 (43.12, 78.42) |

TABLE 9-continued

MiRNA expression in Malignant (N = 21) versus Benign (N = 21) IPMN cases

| miRNA ID | Mean expression malignant cases | Mean expression benign cases | Fold-Change | P | False Discovery Rate | AUC (95% CI) |
|---|---|---|---|---|---|---|
| hsa-miR-28-3p | 3.152179301 | 3.903257667 | 1.683050385 | 0.264833 | 0.985994563 | 55.78 (37.38, 74.18) |
| hsa-miR-1323 | 2.482505819 | 1.928638163 | 1.468015963 | 0.271323 | 0.994850457 | 69.39 (52.24, 86.54) |
| hsa-miR-548ad | 3.361839841 | 4.115826376 | 1.686446481 | 0.292215 | 0.996834076 | 59.41 (41.43, 77.39) |
| hsa-miR-448 | 4.466225515 | 5.148164698 | 1.604294702 | 0.293465 | 0.996834076 | 58.5 (40.74, 76.26) |
| hsa-miR-548d-3p | 3.78738083 | 4.548729888 | 1.695074941 | 0.305973 | 0.996834076 | 56.69 (38.37, 75.01) |
| hsa-miR-593-3p | 2.760059543 | 2.170380491 | 1.504911922 | 0.307035 | 0.996834076 | 68.48 (51.65, 85.31) |
| hsa-miR-19a-3p | 6.973932847 | 7.83962719 | 1.822216455 | 0.315139 | 0.996834076 | 54.88 (36.89, 72.87) |
| hsa-miR-1281 | 2.127607896 | 1.692206645 | 1.352286887 | 0.321062 | 0.996834076 | 69.84 (52.73, 86.95) |
| hsa-miR-1202 | 2.4286124 | 1.984872148 | 1.360125948 | 0.323373 | 0.996834076 | 67.12 (49.85, 84.39) |
| hsa-miR-574-5p | 3.672028665 | 4.30337344 | 1.549008193 | 0.323898 | 0.996834076 | 56.92 (38.79, 75.04) |
| hsa-miR-548p | 2.512748513 | 3.226312145 | 1.639849747 | 0.325975 | 0.996834076 | 56.01 (37.87, 74.14) |
| hsa-miR-513b | 8.353184511 | 7.279216093 | 2.105216225 | 0.330261 | 0.996834076 | 59.18 (41.49, 76.88) |
| hsa-miR-1976 | 13.80073147 | 13.36453869 | 1.353029018 | 0.336869 | 0.996834076 | 61.68 (43.88, 79.48) |
| hsa-miR-151a-5p | 3.26409737 | 3.966714925 | 1.62745489 | 0.336948 | 0.996834076 | 53.97 (35.41, 72.53) |
| hsa-miR-338-3p | 4.727886956 | 5.593815637 | 1.822512464 | 0.337374 | 0.996834076 | 58.05 (40.04, 76.06) |
| hsa-miR-486-3p | 4.174794941 | 3.479885515 | 1.618782802 | 0.342787 | 0.996834076 | 61.45 (44.09, 78.81) |
| hsa-miR-4458 | 2.721133954 | 2.205775111 | 1.429349619 | 0.347082 | 0.996834076 | 65.76 (48.39, 83.13) |
| hsa-miR-663a | 2.469431927 | 3.12894064 | 1.579544642 | 0.34948 | 0.996834076 | 45.12 (26.27, 63.98) |
| hsa-miR-487b | 2.18249922 | 2.751554711 | 1.483551995 | 0.359648 | 0.996834076 | 49.21 (30.74, 67.67) |
| hsa-miR-331-3p | 3.204689676 | 3.786014944 | 1.496223056 | 0.364513 | 0.996834076 | 56.24 (37.8, 74.67) |
| hsa-miR-548k | 1.888421665 | 2.455054405 | 1.481062723 | 0.368103 | 0.996834076 | 48.53 (30.16, 66.89) |
| hsa-let-7a-5p | 11.21513275 | 11.65269129 | 1.354310496 | 0.370617 | 0.996834076 | 61 (42.84, 79.16) |
| hsa-miR-660-5p | 4.921246232 | 5.582434396 | 1.581384473 | 0.374541 | 0.996834076 | 56.24 (37.9, 74.57) |
| hsa-miR-27a-3p | 3.930810842 | 4.644520486 | 1.64001572 | 0.377622 | 0.996834076 | 55.1 (36.83, 73.38) |
| hsa-miR-34c-5p | 4.103426644 | 4.877888542 | 1.710551924 | 0.378155 | 0.996834076 | 56.92 (38.88, 74.95) |
| hsa-miR-98 | 3.732228753 | 4.500835617 | 1.703623887 | 0.380142 | 0.996834076 | 51.93 (33.1, 70.76) |
| hsa-miR-1208 | 2.532797141 | 2.079364521 | 1.369294362 | 0.383502 | 0.996834076 | 65.08 (47.75, 82.4) |
| hsa-miR-382-5p | 2.792415652 | 3.374383889 | 1.49689003 | 0.389714 | 0.996834076 | 54.2 (35.91, 72.48) |
| hsa-miR-337-5p | 2.866781287 | 3.510291351 | 1.562125176 | 0.390578 | 0.996834076 | 50.11 (31.29, 68.94) |
| hsa-miR-494 | 1.922923987 | 2.375462179 | 1.368445703 | 0.396433 | 0.996834076 | 46.49 (28.33, 64.64) |
| hsa-miR-630 | 7.035153992 | 6.602852107 | 1.349384865 | 0.400513 | 0.996834076 | 58.73 (41.05, 76.41) |
| hsa-miR-221-3p | 7.789072228 | 8.541239726 | 1.684321447 | 0.407257 | 0.996834076 | 63.27 (45.54, 80.99) |
| hsa-miR-30d-5p | 5.963105539 | 6.701338067 | 1.668130929 | 0.408002 | 0.996834076 | 47.39 (29.04, 65.74) |
| hsa-miR-484 | 4.350882237 | 5.0082803 | 1.577235472 | 0.410254 | 0.996834076 | 55.33 (37.2, 73.45) |
| hsa-miR-23c | 5.051370615 | 5.808674143 | 1.690328359 | 0.41922 | 0.996834076 | 62.13 (44.33, 79.93) |
| hsa-miR-367-3p | 2.647935062 | 2.194453153 | 1.369341143 | 0.427611 | 0.996834076 | 64.85 (47.58, 82.12) |
| hsa-miR-4455 | 4.094985919 | 4.905756248 | 1.754147822 | 0.431881 | 0.996834076 | 56.24 (38.03, 74.44) |
| hsa-miR-450b-5p | 2.247451804 | 2.763970227 | 1.430498934 | 0.439433 | 0.996834076 | 47.62 (29.29, 65.95) |
| hsa-miR-32-5p | 5.919864275 | 6.541333042 | 1.538440628 | 0.443265 | 0.996834076 | 59.18 (41.5, 76.87) |
| hsa-miR-3184-5p | 1.519863447 | 1.920409697 | 1.320007613 | 0.445155 | 0.996834076 | 50.57 (32.11, 69.02) |
| hsa-miR-499a-3p | 3.603921629 | 4.093124046 | 1.403668654 | 0.452014 | 0.996834076 | 53.29 (35.08, 71.5) |
| hsa-miR-570-3p | 6.986151053 | 7.208022323 | 1.166245303 | 0.452242 | 0.996834076 | 61.68 (44.09, 79.27) |
| hsa-miR-140-5p | 4.923283985 | 5.543787944 | 1.537412133 | 0.46422 | 0.996834076 | 56.69 (37.93, 75.45) |
| hsa-miR-92a-3p | 9.683209011 | 9.264193096 | 1.337015245 | 0.466298 | 0.996834076 | 53.29 (35.37, 71.21) |
| hsa-miR-29a-3p | 3.932950816 | 4.473946348 | 1.454976177 | 0.480011 | 0.996834076 | 55.33 (36.94, 73.71) |
| hsa-miR-568 | 1.768620581 | 2.148120108 | 1.300890496 | 0.484649 | 0.996834076 | 50.79 (32.29, 69.3) |
| hsa-miR-1277-3p | 5.780183603 | 6.214332418 | 1.351113446 | 0.486576 | 0.996834076 | 58.5 (40.61, 76.4) |
| hsa-miR-142-3p | 12.55342461 | 12.87687736 | 1.251321714 | 0.490237 | 0.996834076 | 59.18 (41.24, 77.13) |
| hsa-miR-21-5p | 12.12285373 | 11.8071901 | 1.244584021 | 0.493516 | 0.996834076 | 50.79 (32.57, 69.02) |
| hsa-miR-4425 | 2.656438178 | 2.323466084 | 1.259605615 | 0.516238 | 0.996834076 | 62.59 (44.76, 80.41) |
| hsa-miR-425-5p | 6.910915141 | 7.440609146 | 1.443622971 | 0.517845 | 0.996834076 | 58.28 (40.54, 76.02) |
| hsa-let-7f-5p | 8.046608441 | 8.491764362 | 1.361461249 | 0.519651 | 0.996834076 | 59.86 (42.05, 77.68) |
| hsa-miR-451a | 16.75525225 | 17.19360397 | 1.35505529 | 0.521631 | 0.996834076 | 55.56 (37.39, 73.72) |
| hsa-miR-1244 | 4.465937341 | 4.021689406 | 1.36060466 | 0.526662 | 0.996834076 | 43.08 (25.17, 61) |
| hsa-miR-342-3p | 7.850981879 | 8.329399207 | 1.393214437 | 0.537409 | 0.996834076 | 50.79 (32.66, 68.93) |
| hsa-miR-320e | 9.071504899 | 8.851915053 | 1.164402503 | 0.541821 | 0.996834076 | 60.77 (42.49, 79.05) |
| hsa-miR-155-5p | 3.050058047 | 2.572806622 | 1.392088976 | 0.544862 | 0.996834076 | 66.67 (48.67, 84.67) |
| hsa-miR-2053 | 1.743239398 | 1.997695342 | 1.192885808 | 0.553128 | 0.996834076 | 50.34 (31.81, 68.87) |
| hsa-miR-146a-5p | 8.344249959 | 8.758352711 | 1.332469724 | 0.555214 | 0.996834076 | 60.09 (42.02, 78.16) |
| hsa-miR-548x-3p | 3.339910951 | 2.961746025 | 1.299687631 | 0.556118 | 0.996834076 | 61.68 (44.06, 79.29) |
| hsa-miR-23a-3p | 11.02769168 | 11.29522058 | 1.203744242 | 0.568127 | 0.996834076 | 61 (43, 79) |
| hsa-miR-659-3p | 2.113285438 | 2.472081748 | 1.282355537 | 0.568162 | 0.996834076 | 50.34 (31.93, 68.75) |
| hsa-miR-26b-5p | 10.46033422 | 10.1321358 | 1.255444641 | 0.571187 | 0.996834076 | 49.43 (31.1, 67.76) |
| hsa-miR-4286 | 2.253726026 | 2.025370168 | 1.17149911 | 0.588749 | 0.996834076 | 59.41 (41.55, 77.27) |
| hsa-miR-141-3p | 2.714106218 | 3.09891731 | 1.305688808 | 0.592419 | 0.996834076 | 54.2 (35.57, 72.82) |
| hsa-miR-548g-3p | 3.747155144 | 4.178211443 | 1.348220342 | 0.592427 | 0.996834076 | 51.25 (32.75, 69.74) |
| hsa-miR-127-3p | 2.276815466 | 2.580870687 | 1.234609862 | 0.595809 | 0.996834076 | 54.2 (35.23, 73.16) |
| hsa-miR-148a-3p | 8.051708898 | 8.409785103 | 1.281715625 | 0.604962 | 0.996834076 | 61.22 (43.39, 79.06) |
| hsa-miR-891a | 1.689229414 | 1.953522835 | 1.201047674 | 0.60739 | 0.996834076 | 57.37 (38.77, 75.97) |
| hsa-miR-223-3p | 13.40382745 | 13.65790857 | 1.192575928 | 0.629325 | 0.996834076 | 57.82 (39.79, 75.85) |
| hsa-miR-612 | 3.937772313 | 3.6315993 | 1.236423528 | 0.639314 | 0.996834076 | 58.73 (40.98, 76.48) |
| hsa-miR-548ah-5p | 3.814550838 | 3.343399476 | 1.386215314 | 0.639738 | 0.996834076 | 65.76 (48.4, 83.12) |
| hsa-miR-4461 | 3.022814737 | 2.750007917 | 1.208156058 | 0.641477 | 0.996834076 | 57.6 (39.57, 75.63) |
| hsa-miR-548ae | 3.436200466 | 2.964901886 | 1.386356777 | 0.646207 | 0.996834076 | 67.8 (50.9, 84.7) |

TABLE 9-continued

MiRNA expression in Malignant (N = 21) versus Benign (N = 21) IPMN cases

| miRNA ID | Mean expression malignant cases | Mean expression benign cases | Fold-Change | P | False Discovery Rate | AUC (95% CI) |
|---|---|---|---|---|---|---|
| hsa-miR-106a-5p + hsa-miR-17-5p | 11.21571472 | 10.98352515 | 1.174616304 | 0.648139 | 0.996834076 | 49.89 (31.79, 67.98) |
| hsa-miR-149-5p | 2.995367011 | 2.750037131 | 1.185363779 | 0.649278 | 0.996834076 | 45.58 (27.54, 63.61) |
| hsa-miR-188-5p | 6.894520506 | 6.664756851 | 1.172642829 | 0.650029 | 0.996834076 | 55.56 (37.69, 73.42) |
| hsa-miR-126-3p | 13.12840359 | 13.33640262 | 1.155085008 | 0.654684 | 0.996834076 | 58.73 (40.47, 76.99) |
| hsa-miR-30a-5p | 4.017230996 | 4.339258427 | 1.250086071 | 0.655908 | 0.996834076 | 51.25 (32.71, 69.79) |
| hsa-miR-15a-5p | 10.67056453 | 10.43444612 | 1.177819452 | 0.66222 | 0.996834076 | 51.25 (33.15, 69.35) |
| hsa-miR-219-1-3p | 2.054830715 | 1.801884766 | 1.191637928 | 0.66891 | 0.996834076 | 61.22 (42.91, 79.54) |
| hsa-miR-423-5p | 8.746556611 | 8.495619566 | 1.189979768 | 0.676222 | 0.996834076 | 56.01 (37.94, 74.07) |
| hsa-miR-410 | 2.742735273 | 2.477024067 | 1.202228566 | 0.680498 | 0.996834076 | 60.54 (42.88, 78.21) |
| hsa-miR-2682-5p | 2.585857964 | 2.834092615 | 1.187752835 | 0.684692 | 0.996834076 | 50.34 (32.01, 68.67) |
| hsa-miR-548n | 3.541473085 | 3.094501895 | 1.363175385 | 0.686065 | 0.996834076 | 68.48 (51.82, 85.14) |
| hsa-miR-122-5p | 4.418589571 | 4.743225586 | 1.252348438 | 0.696571 | 0.996834076 | 50.57 (32.45, 68.68) |
| hsa-miR-566 | 2.291489589 | 2.050604201 | 1.181717665 | 0.700093 | 0.996834076 | 58.5 (40.26, 76.75) |
| hsa-miR-516a-5p | 4.05254376 | 4.37317091 | 1.248873325 | 0.702564 | 0.996834076 | 55.78 (37.75, 73.82) |
| hsa-miR-544a | 3.269776826 | 2.941893167 | 1.255170768 | 0.703498 | 0.996834076 | 65.08 (47.43, 82.73) |
| hsa-miR-888-5p | 3.567982561 | 3.91128205 | 1.268654732 | 0.706756 | 0.996834076 | 49.89 (31.62, 68.15) |
| hsa-miR-222-3p | 8.298565154 | 8.433322835 | 1.097908391 | 0.715667 | 0.996834076 | 53.29 (35.23, 71.35) |
| hsa-miR-19b-3p | 10.4584327 | 10.25152898 | 1.154120806 | 0.720014 | 0.996834076 | 51.25 (33.17, 69.32) |
| hsa-miR-384 | 4.012141322 | 4.310780532 | 1.229983711 | 0.722511 | 0.996834076 | 55.1 (37.09, 73.11) |
| hsa-miR-654-3p | 2.577708801 | 2.830902754 | 1.191842792 | 0.726261 | 0.996834076 | 51.02 (32.6, 69.44) |
| hsa-miR-130a-3p | 9.655265129 | 9.901247801 | 1.185900256 | 0.727607 | 0.996834076 | 61.68 (43.68, 79.68) |
| hsa-miR-133b | 1.808221535 | 1.634282537 | 1.128134435 | 0.727716 | 0.996834076 | 61.68 (43.45, 79.91) |
| hsa-miR-106b-5p | 9.796119892 | 9.6015447 | 1.144387141 | 0.735906 | 0.996834076 | 53.06 (34.94, 71.18) |
| hsa-miR-212-3p | 2.854409363 | 3.097930536 | 1.18387862 | 0.737562 | 0.996834076 | 52.15 (34.08, 70.23) |
| hsa-miR-148b-3p | 9.502072458 | 9.68259505 | 1.133294327 | 0.740091 | 0.996834076 | 60.09 (42.23, 77.95) |
| hsa-miR-495 | 8.414734728 | 8.605219093 | 1.141146776 | 0.742411 | 0.996834076 | 59.86 (42.24, 77.49) |
| hsa-miR-143-3p | 3.309124258 | 3.012690203 | 1.228105121 | 0.747466 | 0.996834076 | 63.27 (45.5, 81.04) |
| hsa-miR-4421 | 3.073807129 | 2.844055814 | 1.172632799 | 0.75307 | 0.996834076 | 63.04 (45.36, 80.72) |
| hsa-miR-191-5p | 10.47851698 | 10.64056505 | 1.118874381 | 0.75463 | 0.996834076 | 58.28 (40.04, 76.51) |
| hsa-miR-361-3p | 2.802107592 | 2.633616964 | 1.123882045 | 0.758668 | 0.996834076 | 56.24 (37.97, 74.5) |
| hsa-miR-216b | 2.423964067 | 2.580196166 | 1.114372915 | 0.761938 | 0.996834076 | 48.75 (30.19, 67.32) |
| hsa-miR-489 | 2.005520292 | 2.150126752 | 1.105429072 | 0.764528 | 0.996834076 | 53.51 (35.09, 71.94) |
| hsa-miR-186-5p | 4.597934876 | 4.354784235 | 1.1835746 | 0.767095 | 0.996834076 | 57.6 (39.63, 75.56) |
| hsa-miR-631 | 6.769368497 | 6.876847691 | 1.077344159 | 0.774825 | 0.996834076 | 49.43 (31.29, 67.58) |
| hsa-miR-302b-3p | 5.704246106 | 5.999582003 | 1.227170602 | 0.777445 | 0.996834076 | 53.06 (34.63, 71.49) |
| hsa-miR-548aa | 3.744032696 | 4.102374394 | 1.281951515 | 0.778539 | 0.996834076 | 57.82 (39.73, 75.92) |
| hsa-miR-652-3p | 2.772649599 | 2.594903064 | 1.131115721 | 0.782187 | 0.996834076 | 61 (43.09, 78.91) |
| hsa-miR-1285-3p | 3.344816956 | 3.062094539 | 1.216488276 | 0.782778 | 0.996834076 | 63.04 (45.18, 80.9) |
| hsa-miR-302d-3p | 8.604243192 | 8.525896773 | 1.055307207 | 0.793789 | 0.996834076 | 57.37 (39.41, 75.33) |
| hsa-miR-30e-5p | 8.938101393 | 8.831890655 | 1.076397346 | 0.797944 | 0.996834076 | 54.88 (36.75, 73) |
| hsa-miR-378e | 9.971547907 | 9.90300378 | 1.048657913 | 0.798384 | 0.996834076 | 50.79 (32.51, 69.07) |
| hsa-miR-2117 | 3.101292385 | 3.267840089 | 1.122369495 | 0.799186 | 0.996834076 | 48.3 (29.77, 66.83) |
| hsa-miR-1827 | 4.513224326 | 4.67710345 | 1.120295346 | 0.80128 | 0.996834076 | 51.47 (32.76, 70.19) |
| hsa-miR-197-3p | 5.828470549 | 6.060261839 | 1.174292078 | 0.807774 | 0.996834076 | 50.34 (31.99, 68.69) |
| hsa-miR-4531 | 2.942977952 | 2.743673747 | 1.148144484 | 0.80901 | 0.996834076 | 61.9 (44.34, 79.47) |
| hsa-miR-548q | 2.899253028 | 2.7198341 | 1.132427687 | 0.813173 | 0.996834076 | 61.68 (44.05, 79.3) |
| hsa-miR-454-3p | 3.220396019 | 3.031684916 | 1.139745019 | 0.814855 | 0.996834076 | 54.88 (36.72, 73.03) |
| hsa-miR-185-5p | 9.588145329 | 9.685891741 | 1.070100586 | 0.815781 | 0.996834076 | 52.61 (34.63, 70.58) |
| hsa-miR-30b-5p | 8.810793802 | 8.643342532 | 1.123072661 | 0.820802 | 0.996834076 | 53.97 (35.82, 72.11) |
| hsa-miR-514b-5p | 4.065835965 | 4.227142113 | 1.118299136 | 0.828657 | 0.996834076 | 50.34 (32.32, 68.36) |
| hsa-miR-485-3p | 2.582026554 | 2.72738064 | 1.10600207 | 0.829999 | 0.996834076 | 50.57 (32.48, 68.66) |
| hsa-miR-580 | 2.238566268 | 2.10249165 | 1.098911053 | 0.830568 | 0.996834076 | 56.92 (38.73, 75.1) |
| hsa-miR-941 | 2.840288345 | 2.993389905 | 1.111957432 | 0.842178 | 0.996834076 | 61.9 (43.7, 80.11) |
| hsa-miR-627 | 3.449040503 | 3.29368285 | 1.113697676 | 0.842972 | 0.996834076 | 58.73 (40.79, 76.67) |
| hsa-miR-25-3p | 11.13261955 | 11.2161741 | 1.059625557 | 0.850995 | 0.996834076 | 52.15 (33.57, 70.74) |
| hsa-miR-192-5p | 6.17140045 | 6.087373875 | 1.059972308 | 0.85153 | 0.996834076 | 54.42 (36.46, 72.39) |
| hsa-miR-548ai | 4.14284467 | 4.422964564 | 1.214295793 | 0.855489 | 0.996834076 | 54.42 (36.34, 72.5) |
| hsa-miR-374a-5p | 10.48193066 | 10.37253765 | 1.078774262 | 0.857539 | 0.996834076 | 55.1 (37.19, 73.01) |
| hsa-miR-942 | 3.089149686 | 2.927286581 | 1.118730942 | 0.859653 | 0.996834076 | 58.28 (40.45, 76.1) |
| hsa-miR-1252 | 2.686655159 | 2.791346651 | 1.07526443 | 0.8605 | 0.996834076 | 44.9 (26.03, 63.76) |
| hsa-miR-297 | 1.545578864 | 1.621226244 | 1.053833817 | 0.861361 | 0.996834076 | 55.78 (37.24, 74.33) |
| hsa-miR-487a | 2.656305636 | 2.548103956 | 1.077883816 | 0.866809 | 0.996834076 | 57.82 (39.9, 75.75) |
| hsa-miR-26a-5p | 10.17441552 | 10.27953529 | 1.075583683 | 0.868268 | 0.996834076 | 57.14 (39.04, 75.25) |
| hsa-miR-29c-3p | 6.908813495 | 7.034093467 | 1.090719379 | 0.870736 | 0.996834076 | 54.65 (36.64, 72.66) |
| hsa-miR-519b-5p + hsa-miR-519c-5p | 4.072545076 | 4.237777395 | 1.121346635 | 0.87275 | 0.996834076 | 47.85 (29.61, 66.08) |
| hsa-miR-1537 | 2.50265974 | 2.58799252 | 1.060932433 | 0.87667 | 0.996834076 | 46.26 (27.68, 64.84) |
| hsa-miR-579 | 6.510531519 | 6.463415115 | 1.033197749 | 0.878321 | 0.996834076 | 53.06 (34.98, 71.15) |
| hsa-miR-375 | 5.941039255 | 6.079026659 | 1.100369002 | 0.878959 | 0.996834076 | 50.11 (31.86, 68.37) |
| hsa-miR-93-5p | 10.73907797 | 10.80518263 | 1.04688623 | 0.882345 | 0.996834076 | 48.3 (30.08, 66.52) |
| hsa-miR-548an | 2.584625029 | 2.495584535 | 1.063662528 | 0.889373 | 0.996834076 | 61.22 (43.53, 78.92) |
| hsa-miR-302e | 1.654697787 | 1.728142919 | 1.052226385 | 0.891141 | 0.996834076 | 58.28 (39.81, 76.74) |
| hsa-miR-29b-3p | 7.901772106 | 8.004615995 | 1.073888262 | 0.894647 | 0.996834076 | 59.41 (41.41, 77.41) |

TABLE 9-continued

MiRNA expression in Malignant (N = 21) versus Benign (N = 21) IPMN cases

| miRNA ID | Mean expression malignant cases | Mean expression benign cases | Fold-Change | P | False Discovery Rate | AUC (95% CI) |
|---|---|---|---|---|---|---|
| hsa-miR-1909-3p | 1.735070659 | 1.800146253 | 1.046139754 | 0.896469 | 0.996834076 | 59.64 (40.99, 78.28) |
| hsa-miR-144-3p | 11.12536058 | 11.04642075 | 1.056241571 | 0.89941 | 0.996834076 | 49.89 (31.69, 68.08) |
| hsa-miR-483-3p | 3.074929073 | 2.980551599 | 1.067604635 | 0.90534 | 0.996834076 | 57.82 (39.86, 75.78) |
| hsa-miR-1283 | 2.755860662 | 2.6587311 | 1.069643143 | 0.91552 | 0.996834076 | 57.37 (39.2, 75.54) |
| hsa-miR-2116-5p | 3.938884341 | 3.849961376 | 1.06357588 | 0.924722 | 0.996834076 | 43.76 (25.66, 61.87) |
| hsa-miR-644a | 3.435497628 | 3.348938191 | 1.061834879 | 0.926184 | 0.996834076 | 61.9 (43.95, 79.86) |
| hsa-miR-16-5p | 13.39920769 | 13.35316208 | 1.032431176 | 0.928528 | 0.996834076 | 54.65 (36.25, 73.05) |
| hsa-miR-1286 | 2.353067246 | 2.39897386 | 1.03233171 | 0.930227 | 0.996834076 | 56.92 (38.1, 75.74) |
| hsa-miR-20a-5p + hsa-miR-20b-5p | 10.33698635 | 10.37678015 | 1.027966891 | 0.930243 | 0.996834076 | 46.94 (28.91, 64.97) |
| hsa-miR-548z | 4.023611603 | 4.104783787 | 1.057877213 | 0.930261 | 0.996834076 | 44.67 (26.52, 62.82) |
| hsa-miR-4516 | 5.255182651 | 5.206561957 | 1.03427562 | 0.93686 | 0.996834076 | 50.11 (31.92, 68.31) |
| hsa-miR-15b-5p | 11.25727487 | 11.21434518 | 1.030203744 | 0.938165 | 0.996834076 | 54.42 (36.33, 72.51) |
| hsa-miR-95 | 1.57943031 | 1.614876557 | 1.024873783 | 0.939958 | 0.996834076 | 58.96 (40.81, 77.1) |
| hsa-miR-548aj-3p | 2.454456398 | 2.496723465 | 1.029730686 | 0.945902 | 0.996834076 | 54.88 (36.55, 73.2) |
| hsa-miR-1225-5p | 1.805566379 | 1.774806251 | 1.021550219 | 0.949197 | 0.996834076 | 59.18 (40.78, 77.58) |
| hsa-miR-421 | 2.126777928 | 2.159630406 | 1.023032854 | 0.949346 | 0.996834076 | 56.92 (38.6, 75.23) |
| hsa-miR-330-5p | 1.7563051 | 1.731674993 | 1.017218853 | 0.961125 | 0.996834076 | 60.09 (42, 78.18) |
| hsa-miR-1260b | 3.300520497 | 3.262513356 | 1.026694628 | 0.966503 | 0.996834076 | 57.6 (39.39, 75.8) |
| hsa-let-7g-5p | 11.95697546 | 11.94017645 | 1.011712242 | 0.970112 | 0.996834076 | 52.61 (34.52, 70.7) |
| hsa-miR-647 | 1.695577265 | 1.677652928 | 1.012501705 | 0.970807 | 0.996834076 | 55.56 (37.54, 73.57) |
| hsa-miR-548al | 7.515115326 | 7.483156786 | 1.022399149 | 0.971989 | 0.996834076 | 60.54 (42.44, 78.65) |
| hsa-miR-518c-3p | 1.811948853 | 1.795002991 | 1.011815231 | 0.972713 | 0.996834076 | 57.14 (38.82, 75.46) |
| hsa-miR-520h | 2.89411999 | 2.874606357 | 1.013617707 | 0.97275 | 0.996834076 | 47.62 (29.32, 65.92) |
| hsa-let-7b-5p | 10.99090937 | 11.00523262 | 1.009977569 | 0.973133 | 0.996834076 | 51.7 (33.39, 70.01) |
| hsa-let-7i-5p | 8.797476785 | 8.781816025 | 1.010914344 | 0.979788 | 0.996834076 | 58.05 (39.65, 76.45) |
| hsa-miR-614 | 1.881240144 | 1.871365465 | 1.006868084 | 0.980362 | 0.996834076 | 59.64 (41.77, 77.5) |
| hsa-miR-4508 | 2.944305798 | 2.9611139 | 1.01171862 | 0.981551 | 0.996834076 | 49.89 (31.79, 67.98) |
| hsa-miR-22-3p | 10.06059719 | 10.05543513 | 1.003584475 | 0.98907 | 0.996834076 | 53.06 (35.03, 71.09) |
| hsa-miR-3934 | 2.386905365 | 2.381627584 | 1.003664979 | 0.991045 | 0.996834076 | 60.77 (42.29, 79.26) |
| hsa-miR-150-5p | 8.975382521 | 8.978884461 | 1.002430308 | 0.995193 | 0.996834076 | 53.97 (36.02, 71.92) |
| hsa-let-7c | 3.271043481 | 3.267934067 | 1.002157606 | 0.996341 | 0.996834076 | 44.44 (25.83, 63.06) |
| hsa-miR-876-3p | 1.950449012 | 1.948221418 | 1.001545243 | 0.996834 | 0.996834076 | 57.14 (38.78, 75.51) |

D. IPMN Tumors Tissue and Paired Plasma have Distinct miRNA Expression Profiles

To address whether circulating miRNA expression reflects miRNA expression in corresponding IPMN tumor tissue, we evaluated matched plasma and tissue specimens from 12 IPMN cases. Of a total of 160 miRNA probes that were evaluated in both specimen types, expression levels of only 3 (1.9%) were significantly positively correlated (r>0.60, p<0.05) in matched tissue and plasma, and included miR-484 (r=0.70, p=0.015), miR-330 (r=0.63, p=0.026), and miR-574-3p (r=0.64, p=0.030) (Table 10). Of these three miRNA probes, one (miR-574-3p) was represented in the 5-miRNA signature that differentiated between malignant and benign IPMNs. For the miRNAs that were ranked as the most highly expressed in the plasma of IPMN cases versus controls (i.e., miR-146a-5p, miR-340-5p, and miR-181a-5p), correlations with tissue miRNA expression were small (r<0.60) (Table 10). Overall, our data suggest plasma and tissue samples from patients with IPMNs can have distinct miRNA expression profiles.

TABLE 10

Correlation between Paired Tissue and Plasma MiRNA Expression in 12 Individuals with IPMNs

| Tissue MiRNA Probe | Plasma MiRNA Probe | Spearman Correlation | P Value | IPMN vs Control 30 miRNA Signature | Malignant vs Benign 5 miRNA Signature |
|---|---|---|---|---|---|
| hsa-miR-876-5p-002205 (FAM, NFQ) | hsa-miR-876-3p | −0.75267378 | 0.004727878 | | |
| hsa-miR-219-000522 (FAM, NFQ) | hsa-miR-219-5p | −0.740561791 | 0.005872143 | | |
| hsa-miR-484-001821 (FAM, NFQ) | hsa-miR-484 | 0.699300699 | 0.014539312 | | |
| hsa-miR-219-000522 (FAM, NFQ) | hsa-miR-219-1-3p | −0.657352601 | 0.020182953 | | |
| hsa-miR-330-000544 (FAM, NFQ) | hsa-miR-330-5p | 0.633818534 | 0.026890701 | | |
| hsa-miR-574-3p-002349 (FAM, NFQ) | hsa-miR-574-3p | 0.636363636 | 0.030114265 | | Yes |
| hsa-miR-34c-000428 (FAM, NFQ) | hsa-miR-34c-5p | 0.565925895 | 0.055108369 | | |
| hsa-miR-338-3p-002252 (FAM, NFQ) | hsa-miR-338-3p | 0.542266968 | 0.068541125 | | |
| hsa-miR-361-000554 (FAM, NFQ) | hsa-miR-361-3p | −0.545454545 | 0.070678905 | | |
| hsa-miR-375-000564 (FAM, NFQ) | hsa-miR-375 | −0.545454545 | 0.070678905 | | |
| hsa-miR-136-000592 (FAM, NFQ) | hsa-miR-136-5p | −0.533892354 | 0.073792459 | | |
| hsa-miR-324-3p-002161 (FAM, NFQ) | hsa-miR-324-5p | 0.531468531 | 0.079302939 | | |
| hsa-miR-330-5p-002230 (FAM, NFQ) | hsa-miR-330-5p | −0.514021118 | 0.087341289 | | |
| hsa-miR-548d-5p-002237 (FAM, NFQ) | hsa-miR-548d-3p | −0.507054827 | 0.092464184 | | |
| hsa-miR-579-002398 (FAM, NFQ) | hsa-miR-579 | 0.51048951 | 0.09360538 | | |
| hsa-miR-223-002295 (FAM, NFQ) | hsa-miR-223-3p | 0.496503497 | 0.104092833 | yes | |
| hsa-miR-197-000497 (FAM, NFQ) | hsa-miR-197-3p | 0.496503497 | 0.104092833 | | |

TABLE 10-continued

Correlation between Paired Tissue and Plasma MiRNA Expression in 12 Individuals with IPMNs

| Tissue MiRNA Probe | Plasma MiRNA Probe | Spearman Correlation | P Value | IPMN vs Control 30 miRNA Signature | Malignant vs Benign 5 miRNA Signature |
|---|---|---|---|---|---|
| hsa-miR-21-000397 (FAM, NFQ) | hsa-miR-21-5p | 0.482517483 | 0.115373605 | | |
| hsa-miR-431-001979 (FAM, NFQ) | hsa-miR-431-5p | −0.468126376 | 0.124825063 | | |
| hsa-miR-188-3p-002106 (FAM, NFQ) | hsa-miR-188-5p | −0.465971464 | 0.126806857 | | |
| hsa-miR-125a-5p-002198 (FAM, NFQ) | hsa-miR-125a-5p | 0.461538462 | 0.133836316 | | |
| hsa-miR-155-002623 (FAM, NFQ) | hsa-miR-155-5p | −0.461538462 | 0.133836316 | | |
| hsa-miR-98-000577 (FAM, NFQ) | hsa-miR-98 | 0.41604595 | 0.178556865 | yes | |
| hsa-miR-423-5p-002340 (FAM, NFQ) | hsa-miR-423-5p | 0.412587413 | 0.184480685 | yes | |
| hsa-miR-148a-000470 (FAM, NFQ) | hsa-miR-148a-3p | 0.405594406 | 0.192612184 | yes | |
| hsa-miR-548d-001605 (FAM, NFQ) | hsa-miR-548d-3p | 0.399404112 | 0.198348249 | | |
| hsa-miR-342-3p-002260 (FAM, NFQ) | hsa-miR-342-3p | −0.391608392 | 0.209564352 | | |
| hsa-miR-660-001515 (FAM, NFQ) | hsa-miR-660-5p | 0.391608392 | 0.209564352 | | |
| hsa-miR-888-002212 (FAM, NFQ) | hsa-miR-888-5p | −0.387333548 | 0.213511553 | | |
| hsa-miR-142-5p-002248 (FAM, NFQ) | hsa-miR-142-3p | −0.377622378 | 0.227443132 | | |
| hsa-miR-152-000475 (FAM, NFQ) | hsa-miR-152 | 0.370629371 | 0.236732214 | | |
| hsa-miR-216b-002326 (FAM, NFQ) | hsa-miR-216b | −0.365768413 | 0.242300452 | | |
| hsa-miR-454-002323 (FAM, NFQ) | hsa-miR-454-3p | −0.356643357 | 0.256012537 | | |
| hsa-miR-23a-000399 (FAM, NFQ) | hsa-miR-23a-3p | 0.348054616 | 0.267575666 | yes | |
| hsa-let-7e-002406 (FAM, NFQ) | hsa-let-7e-5p | 0.342657343 | 0.276230513 | | |
| hsa-miR-367-000555 (FAM, NFQ) | hsa-miR-367-3p | −0.336252705 | 0.285226087 | | |
| hsa-miR-192-000491 (FAM, NFQ) | hsa-miR-192-5p | 0.335664336 | 0.286690914 | | |
| hsa-miR-10a-000387 (FAM, NFQ) | hsa-miR-10a-5p | −0.335664336 | 0.286690914 | | |
| hsa-miR-125a-3p-002199 (FAM, NFQ) | hsa-miR-125a-5p | 0.322242175 | 0.307014179 | | |
| hsa-miR-107-000443 (FAM, NFQ) | hsa-miR-107 | 0.321678322 | 0.308312361 | yes | |
| hsa-miR-24-000402 (FAM, NFQ) | hsa-miR-24-3p | 0.321678322 | 0.308312361 | yes | |
| hsa-miR-483-5p-002338 (FAM, NFQ) | hsa-miR-483-3p | −0.321678322 | 0.308312361 | | |
| hsa-let-7a-000377 (FAM, NFQ) | hsa-let-7a-5p | 0.314685315 | 0.319471913 | yes | |
| hsa-miR-891a-002191 (FAM, NFQ) | hsa-miR-891a | 0.3117829 | 0.323864452 | | |
| hsa-miR-489-002358 (FAM, NFQ) | hsa-miR-489 | 0.311734278 | 0.323943941 | | |
| hsa-miR-325-000540 (FAM, NFQ) | hsa-miR-325 | −0.305699203 | 0.333893136 | | |
| hsa-miR-450b-3p-002208 (FAM, NFQ) | hsa-miR-450b-5p | −0.305699203 | 0.333893136 | | |
| hsa-miR-219-2-3p-002390 (FAM, NFQ) | hsa-miR-219-5p | −0.305699203 | 0.333893136 | | |
| hsa-miR-516a-5p-002416 (FAM, NFQ) | hsa-miR-516a-5p | −0.305699203 | 0.333893136 | | |
| hsa-miR-133b-002247 (FAM, NFQ) | hsa-miR-133b | −0.275368456 | 0.386340424 | | |
| mmu-miR-93-001090 (FAM, NFQ) | hsa-miR-93-5p | 0.26970269 | 0.396580033 | | |
| hsa-miR-127-5p-002229 (FAM, NFQ) | hsa-miR-127-3p | −0.266269408 | 0.402851144 | | |
| hsa-miR-185-002271 (FAM, NFQ) | hsa-miR-185-5p | 0.265734266 | 0.403976659 | | |
| hsa-miR-106b-000442 (FAM, NFQ) | hsa-miR-106b-5p | 0.258741259 | 0.416938427 | | |
| hsa-miR-26b-000407 (FAM, NFQ) | hsa-miR-26b-5p | 0.258741259 | 0.416938427 | | |
| hsa-let-7c-000379 (FAM, NFQ) | hsa-let-7c | −0.258741259 | 0.416938427 | | |
| hsa-miR-382-000572 (FAM, NFQ) | hsa-miR-382-5p | 0.257333899 | 0.419403871 | | |
| hsa-miR-146a-000468 (FAM, NFQ) | hsa-miR-146a-5p | −0.251748252 | 0.430115289 | yes | |
| hsa-let-7f-000382 (FAM, NFQ) | hsa-let-7f-5p | 0.237762238 | 0.457102207 | yes | |
| hsa-miR-199a-000498 (FAM, NFQ) | hsa-miR-199a-5p | −0.237762238 | 0.457102207 | | |
| hsa-miR-199a-3p-002304 (FAM, NFQ) | hsa-miR-199a-5p | −0.237762238 | 0.457102207 | | |
| hsa-miR-150-000473 (FAM, NFQ) | hsa-miR-150-5p | 0.237762238 | 0.457102207 | | |
| hsa-miR-143-002249 (FAM, NFQ) | hsa-miR-143-3p | −0.237762238 | 0.457102207 | | |
| hsa-miR-212-000515 (FAM, NFQ) | hsa-miR-212-3p | −0.237762238 | 0.457102207 | | |
| hsa-miR-518b-001156 (FAM, NFQ) | hsa-miR-518b | −0.233939909 | 0.464282613 | | |
| hsa-miR-590-5p-001984 (FAM, NFQ) | hsa-miR-590-5p | 0.230769231 | 0.470905694 | | |
| hsa-miR-186-002285 (FAM, NFQ) | hsa-miR-186-5p | −0.230769231 | 0.470905694 | | |
| hsa-miR-99b-000436 (FAM, NFQ) | hsa-miR-99b-5p | 0.230769231 | 0.470905694 | | |
| hsa-let-7d-002283 (FAM, NFQ) | hsa-let-7d-5p | 0.223776224 | 0.48491114 | yes | |
| hsa-miR-219-2-3p-002390 (FAM, NFQ) | hsa-miR-219-1-3p | −0.218356573 | 0.49536676 | | |
| hsa-miR-450b-5p-002207 (FAM, NFQ) | hsa-miR-450b-5p | −0.218356573 | 0.49536676 | | |
| hsa-miR-181a-000480 (FAM, NFQ) | hsa-miR-181a-5p | −0.216783217 | 0.499114748 | yes | |
| hsa-miR-335-000546 (FAM, NFQ) | hsa-miR-335-5p | 0.216783217 | 0.499114748 | yes | |
| hsa-miR-425-5p-001516 (FAM, NFQ) | hsa-miR-425-5p | −0.213660573 | 0.504912688 | | |
| hsa-miR-191-002299 (FAM, NFQ) | hsa-miR-191-5p | 0.20979021 | 0.513512513 | yes | |
| hsa-miR-324-5p-000539 (FAM, NFQ) | hsa-miR-324-5p | 0.20979021 | 0.513512513 | | |
| hsa-miR-127-000452 (FAM, NFQ) | hsa-miR-127-3p | −0.20979021 | 0.513512513 | | |
| hsa-miR-654-3p-002239 (FAM, NFQ) | hsa-miR-654-3p | 0.208022975 | 0.516479059 | | |
| hsa-miR-331-000545 (FAM, NFQ) | hsa-miR-331-3p | −0.204230416 | 0.524324327 | | |
| hsa-miR-221-000524 (FAM, NFQ) | hsa-miR-221-3p | 0.192644779 | 0.548602519 | | |
| hsa-miR-29c-000587 (FAM, NFQ) | hsa-miR-29c-3p | 0.188811189 | 0.557827775 | yes | |
| hsa-miR-16-000391 (FAM, NFQ) | hsa-miR-16-5p | 0.188811189 | 0.557827775 | | |
| hsa-miR-423-5p-002340 (FAM, NFQ) | hsa-miR-423-3p | 0.181818182 | 0.572958221 | | |
| hsa-miR-487b-001285 (FAM, NFQ) | hsa-miR-487b | 0.176060704 | 0.58414053 | | |
| hsa-miR-302b-000531 (FAM, NFQ) | hsa-miR-302b-3p | 0.176060704 | 0.58414053 | | |
| hsa-miR-32-002109 (FAM, NFQ) | hsa-miR-32-5p | −0.174825175 | 0.588259895 | | |
| hsa-miR-130a-000454 (FAM, NFQ) | hsa-miR-130a-3p | 0.167832168 | 0.603727651 | | |
| hsa-miR-570-002347 (FAM, NFQ) | hsa-miR-570-3p | −0.166642584 | 0.604712895 | | |
| hsa-miR-515-3p-002369 (FAM, NFQ) | hsa-miR-515-5p | −0.165221074 | 0.607841489 | | |
| hsa-miR-23b-000400 (FAM, NFQ) | hsa-miR-23b-3p | 0.160839161 | 0.619356169 | | |
| hsa-miR-652-002352 (FAM, NFQ) | hsa-miR-652-3p | 0.160839161 | 0.619356169 | | |

TABLE 10-continued

Correlation between Paired Tissue and Plasma MiRNA Expression in 12 Individuals with IPMNs

| Tissue MiRNA Probe | Plasma MiRNA Probe | Spearman Correlation | P Value | IPMN vs Control 30 miRNA Signature | Malignant vs Benign 5 miRNA Signature |
|---|---|---|---|---|---|
| hsa-miR-30b-000602 (FAM, NFQ) | hsa-miR-30b-5p | 0.153846154 | 0.635139955 | yes | |
| hsa-miR-200a-000502 (FAM, NFQ) | hsa-miR-200a-3p | 0.153846154 | 0.635139955 | | Yes |
| hsa-miR-363-001271 (FAM, NFQ) | hsa-miR-363-3p | 0.146853147 | 0.651073351 | | |
| hsa-miR-219-l-3p-002095 (FAM, NFQ) | hsa-miR-219-l-3p | 0.145140315 | 0.652662819 | | |
| hsa-miR-340-002258 (FAM, NFQ) | hsa-miR-340-5p | 0.13986014 | 0.667150536 | yes | |
| hsa-miR-25-000403 (FAM, NFQ) | hsa-miR-25-3p | 0.13986014 | 0.667150536 | | |
| hsa-miR-486-3p-002093 (FAM, NFQ) | hsa-miR-486-3p | −0.13525273 | 0.675137513 | | |
| hsa-miR-126-002228 (FAM, NFQ) | hsa-miR-126-3p | 0.132867133 | 0.683365534 | yes | |
| mmu-miR-140-001187 (FAM, NFQ) | hsa-miR-140-5p | −0.132867133 | 0.683365534 | | |
| hsa-miR-487a-001279 (FAM, NFQ) | hsa-miR-487a | 0.131013944 | 0.684848714 | | |
| hsa-miR-520f-001120 (FAM, NFQ) | hsa-miR-520f | −0.131013944 | 0.684848714 | | |
| hsa-miR-18a-002422 (FAM, NFQ) | hsa-miR-18a-5p | −0.125874126 | 0.699712221 | yes | |
| hsa-let-7b-002619 (FAM, NFQ) | hsa-let-7b-5p | 0.125874126 | 0.699712221 | | |
| hsa-miR-222-002276 (FAM, NFQ) | hsa-miR-222-3p | −0.125874126 | 0.699712221 | | |
| hsa-miR-141-000463 (FAM, NFQ) | hsa-miR-141-3p | −0.125874126 | 0.699712221 | | |
| hsa-miR-494-002365 (FAM, NFQ) | hsa-miR-494 | 0.123269343 | 0.702704573 | | |
| hsa-miR-145-002278 (FAM, NFQ) | hsa-miR-145-5p | −0.1210156 | 0.707927241 | yes | |
| hsa-miR-92a-000431 (FAM, NFQ) | hsa-miR-92a-3p | −0.118881119 | 0.716184327 | | |
| hsa-miR-219-l-3p-002095 (FAM, NFQ) | hsa-miR-219-5p | 0.112886912 | 0.726858861 | | |
| hsa-miR-27a-000408 (FAM, NFQ) | hsa-miR-27a-3p | 0.111888112 | 0.732775446 | yes | |
| hsa-miR-29b-000413 (FAM, NFQ) | hsa-miR-29b-3p | 0.111888112 | 0.732775446 | | |
| hsa-miR-376c-002122 (FAM, NFQ) | hsa-miR-376c | 0.111888112 | 0.732775446 | | |
| hsa-miR-548a-001538 (FAM, NFQ) | hsa-miR-548a-3p | −0.109171957 | 0.735558555 | | |
| hsa-miR-142-3p-000464 (FAM, NFQ) | hsa-miR-142-3p | −0.10507897 | 0.745176622 | yes | |
| hsa-miR-15b-000390 (FAM, NFQ) | hsa-miR-15b-5p | 0.104895105 | 0.749479043 | yes | |
| hsa-miR-95-000433 (FAM, NFQ) | hsa-miR-95 | 0.104895105 | 0.749479043 | | |
| hsa-miR-125b-000449 (FAM, NFQ) | hsa-miR-125b-5p | 0.090909091 | 0.78319691 | | |
| hsa-miR-28-000411 (FAM, NFQ) | hsa-miR-28-3p | −0.083916084 | 0.800197518 | | |
| hsa-miR-149-002255 (FAM, NFQ) | hsa-miR-149-5p | −0.079762516 | 0.80536501 | | |
| hsa-miR-140-3p-002234 (FAM, NFQ) | hsa-miR-140-5p | 0.076234077 | 0.817283291 | | |
| hsa-let-7g-002282 (FAM, NFQ) | hsa-let-7g-5p | 0.06993007 | 0.834447145 | yes | |
| hsa-miR-28-3p-002446 (FAM, NFQ) | hsa-miR-28-5p | −0.06993007 | 0.834447145 | | |
| hsa-miR-410-001274 (FAM, NFQ) | hsa-miR-410 | −0.06993007 | 0.834447145 | | |
| hsa-miR-19b-000396 (FAM, NFQ) | hsa-miR-19b-3p | 0.066550014 | 0.837187854 | | |
| hsa-miR-486-001278 (FAM, NFQ) | hsa-miR-486-3p | 0.062937063 | 0.851681911 | | |
| hsa-miR-574-3p-002349 (FAM, NFQ) | hsa-miR-574-5p | −0.062937063 | 0.851681911 | | |
| hsa-miR-627-001560 (FAM, NFQ) | hsa-miR-627 | −0.055984961 | 0.862798664 | | |
| hsa-miR-450a-002303 (FAM, NFQ) | hsa-miR-450a-5p | 0.055073691 | 0.865013709 | | |
| hsa-miR-28-3p-002446 (FAM, NFQ) | hsa-miR-28-3p | −0.055944056 | 0.868980339 | | |
| hsa-miR-376a-000565 (FAM, NFQ) | hsa-miR-376a-3p | 0.055944056 | 0.868980339 | | |
| hsa-miR-485-3p-001277 (FAM, NFQ) | hsa-miR-485-3p | 0.055944056 | 0.868980339 | | |
| hsa-miR-409-5p-002331 (FAM, NFQ) | hsa-miR-409-3p | −0.043671315 | 0.892800448 | | |
| hsa-miR-29a-002112 (FAM, NFQ) | hsa-miR-29a-3p | −0.041958042 | 0.903738836 | | |
| hsa-miR-15a-000389 (FAM, NFQ) | hsa-miR-15a-5p | −0.034965035 | 0.921184083 | | |
| hsa-miR-19a-000395 (FAM, NFQ) | hsa-miR-19a-3p | −0.034965035 | 0.921184083 | | |
| hsa-miR-122-002245 (FAM, NFQ) | hsa-miR-122-5p | −0.029123216 | 0.928410573 | | |
| mmu-miR-495-001663 (FAM, NFQ) | hsa-miR-495 | 0.028169713 | 0.930749393 | | |
| hsa-miR-337-5p-002156 (FAM, NFQ) | hsa-miR-337-3p | 0.028169713 | 0.930749393 | | |
| hsa-miR-370-002275 (FAM, NFQ) | hsa-miR-370 | −0.020802297 | 0.948836372 | | |
| hsa-miR-26a-000405 (FAM, NFQ) | hsa-miR-26a-5p | 0.020979021 | 0.956169155 | yes | |
| hsa-miR-361-000554 (FAM, NFQ) | hsa-miR-361-5p | 0.020979021 | 0.956169155 | | |
| hsa-miR-28-000411 (FAM, NFQ) | hsa-miR-28-5p | −0.020979021 | 0.956169155 | | |
| hsa-miR-598-001988 (FAM, NFQ) | hsa-miR-598 | 0.020979021 | 0.956169155 | | |
| hsa-miR-22-000398 (FAM, NFQ) | hsa-miR-22-3p | −0.017513162 | 0.956918824 | yes | |
| hsa-miR-515-5p-001112 (FAM, NFQ) | hsa-miR-515-5p | −0.016126702 | 0.960326954 | | |
| hsa-miR-331-5p-002233 (FAM, NFQ) | hsa-miR-331-3p | −0.013986014 | 0.973693904 | | |
| hsa-miR-337-5p-002156 (FAM, NFQ) | hsa-miR-337-5p | 0 | 1 | yes | |
| hsa-miR-27b-000409 (FAM, NFQ) | hsa-miR-27b-3p | 0 | 1 | | |
| hsa-miR-148b-000471 (FAM, NFQ) | hsa-miR-148b-3p | 0 | 1 | | |
| hsa-miR-503-001048 (FAM, NFQ) | hsa-miR-503 | NA | NA | | |
| hsa-miR-891b-022210 (FAM, NFQ) | hsa-miR-891b | NA | NA | | |
| hsa-miR-518c-002401 (FAM, NFQ) | hsa-miR-518c-3p | NA | NA | | |
| hsa-miR-342-5p-002147 (FAM, NFQ) | hsa-miR-342-3p | NA | NA | | |
| hsa-miR-654-001611 (FAM, NFQ) | hsa-miR-654-3p | NA | NA | | |
| hsa-miR-548a-5p-002412 (FAM, NFQ) | hsa-miR-548a-3p | NA | NA | | |
| hsa-miR-876-3p-002225 (FAM, NFQ) | hsa-miR-876-3p | NA | NA | | |
| hsa-miR-485-5p-001036 (FAM, NFQ) | hsa-miR-485-3p | NA | NA | | |
| hsa-miR-384-000574 (FAM, NFQ) | hsa-miR-384 | NA | NA | | |
| hsa-miR-448-001029 (FAM, NFQ) | hsa-miR-448 | NA | NA | | |

This is the first report to interrogate plasma miRNA expression levels exclusively in individuals newly-diagnosed with IPMNs and healthy controls. We used highly sensitive and specific NCOUNTER™ technology for miRNA quantitation and implemented an extensive quality control and data analysis pipeline to account for pre-analytical and technical factors that can affect circulating miRNA levels and result in biases that do not reflect the underlying biology of the samples. This study demonstrates the feasibility of evaluating plasma miRNAs using NCOUNTER™ technology, and our results suggest that miRNAs circulating in plasma warrant further evaluation as minimally invasive biomarkers for the detection of PDAC precursors and as possible targets for chemoprevention efforts.

We show that a 30-miRNA gene signature can discriminate IPMN cases from non-diseased healthy controls ((AUC)=74.4 (95% CI: 62.3-86.5, p=0.002)). Fortunately, a number of the miRNAs highlighted in this signature (let-7a-5p, let-7d-5p, miR-1260b, miR-142-3p, and miR-146a-5p, miR-23a-3p) have been shown to be unaffected by hemolysis (63,65), which minimizes red blood cell contamination as a potential source of confounding. The miRNAs represented in the signature had 2-4-fold higher expression in cases compared to controls, and included miRNAs previously shown to be up-regulated in PDAC versus normal tissues (i.e., miR-107, miR-145, miR-146a, miR-15b, miR-181a, and miR-24) (75) and miRNAs shown to be down-regulated in PDAC versus normal tissues (i.e., miR-142, miR-148a) (75). Noteworthy, several identified miRNAs (miR-145-5p and miR-335) may be involved in inhibiting cancer stem cell properties of pancreatic cancers by targeting the transcription factor, OCT4 (76,77). Candidate miRNAs such as miR-1260b and miR-4454 are novel and also of interest because validated targets include key players in pancreatic carcinogenesis, SMAD4 (78) and NF-κβ (79), respectively. Collectively, the biological plausibility of findings was enhanced by in silico pathway-based exploratory analysis which predicted that the 30 differentially expressed circulating miRNAs may affect critical pathways involved in PDAC initiation and progression.

Li et al. (48) recently reported on their efforts to identify miRNA levels in sera that could distinguish patients with early-stage PDAC from healthy controls. miR-1290 had the best diagnostic performance for subjects with PDAC (n=41) relative to healthy controls (n=19), and serum miR-1290 levels were also significantly higher than controls among 20 patients with IPMNs (AUC=0.76). Although miR-1290 was evaluated as part of the NCOUNTER miRNA codeset, expression levels of this miRNA were not analyzed because 93% of the 69 samples had values below background levels. Two miRNAs from our 30-miRNA gene signature, miR-24 and miR-146a, were among the miRNAs that distinguished sera of patients with PDAC from healthy controls with AUCs>0.70 in the study by Li et al. (48), but comparisons of these levels in IPMNs versus healthy controls were not reported. None of the circulating miRNAs identified in our study overlapped with three miRNAs (miR-642b, miR-885, 5-p, miR-22) highlighted in a small study of plasma miRNA expression in early PDAC patients versus controls by Ganepola and colleagues (58).

We also conducted exploratory analysis and discovered a 5-miRNA signature (comprising miR-200a-3p, miR-1185-5p, miR-33a-5p, miR-574-3p, and miR-663b) that can discriminate between malignant and benign IPMNs (AUC=73.2 (95% CI: 57.6-88.9)). These miRNAs had 2-3 fold lower expression in the plasma of malignant as opposed to benign cases. Consistent with our findings of reduced miR-200a expression in malignant IPMNs, miR-200a down-regulation has been implicated in epithelial-to-mesenchymal transition and early metastasis (75). On the other hand, miR-200a was previously shown to be hypomethylated and overexpressed in PDAC (compared to normal) tissue and in the sera of PDAC patients versus controls (80). Another miRNA in the signature, miR-574-3p, has been shown to act as a tumor suppressor and to regulate cell signaling pathways in prostate and gastric cancer cells (81,82), suggesting low levels of miR-574-3p may regulate key oncogenes that promote malignant IPMN status. Although the identified circulating miRNAs may play a role in differentiating between malignant and benign IPMNs, larger studies that account for clinical and radiologic factors are needed to confirm and expand upon these findings.

Based on our observation that candidate plasma miRNA levels were not strongly correlated with paired tissue miRNA expression in a subset of IPMN cases, it will also be necessary to further explore the origin of circulating miRNAs in IPMN patients. Discrepancies between plasma and tumor miRNA profiles have been reported previously (72, 83), challenging the popular hypothesis that the origin of circulating miRNAs is from tumors as a result of cell death and lysis. Alternative explanations for the origin of circulating miRNAs include the following: blood cell contamination; normal cell contamination; tumor cells release miRNAs into the tumor microenvironment where they enter newly formed blood vessels and make their way into circulation; heterogeneity of the primary tumor; dietary sources; and locoregional inflammation that reflects a systematic response of the host microenvironment to the disease (64, 84-86). It is also possible that certain miRNA sequences could be more easily degraded and/or or more easily released from cells, affecting differential expression. Taken together, this data suggests that biomarker discovery of circulating miRNAs seems to warrant a genome-wide approach rather than relying on differentially expressed miRNAs identified through tissue-based studies.

With archived plasma available from a total of 42 cases and 24 controls we had at least 85% power to detect a miRNA expression difference of 2-fold and above, assuming a set of 800 miRNAs, a standard deviation of 1, and a 15% FDR. Technical validation of the Nanostring assay and external validation of findings in a large, independent study population may be done. Further, a large-scale prospective investigation of serial plasma miRNA measurements (pre- and post-surgery or during surveillance) may be done for individuals newly-diagnosed with various types of pancreatic cysts (including IPMNs, MCNs, and benign, non-mucinous cysts) and early-stage PDAC and those at high genetic risk for developing PDAC. To increase diagnostic accuracy and improve outcomes, it will also be necessary to integrate novel classes of molecular markers and/or imaging techniques to improve sensitivity and specificity of the miRNA-based assay in conjunction with clinical characteristics.

In summary, our methodologically-sound study is the first of its kind to support the development of a plasma miRNA assay to detect IPMNs using NCOUNTER™ technology. Future large-scale studies with rigorous designs are needed to further explore the exciting potential for circulating miRNAs to be utilized clinically as novel biomarkers for IPMNs and possibly other PDAC precursors.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. American Cancer Society. Cancer Facts and Figures 2013. Atlanta: American Cancer Society. 2013.
2. Hruban R H, Maitra A, Kern S E, Goggins M. Precursors to pancreatic cancer. Gastroenterol Clin North Am. 2007; 36:831-49, vi.
3. Allen P J. The management of intraductal papillary mucinous neoplasms of the pancreas. Surg Oncol Clin N Am. 2010; 19:297-310.
4. Sachs T, Pratt W B, Callery M P, Vollmer C M, Jr. The incidental asymptomatic pancreatic lesion: nuisance or threat? J Gastrointest Surg. 2009; 13:405-15.
5. Matthaei H, Schulick R D, Hruban R H, Maitra A. Cystic precursors to invasive pancreatic cancer. Nat Rev Gastroenterol Hepatol. 2011; 8:141-50.
6. Yachida S. et al. Distant metastasis occurs late during the genetic evolution of pancreatic cancer. Nature. 2010; 467:1114-7.
7. Sahani D V. et al. Multidisciplinary approach to diagnosis and management of intraductal papillary mucinous neoplasms of the pancreas. Clin Gastroenterol Hepatol. 2009; 7:259-69.
8. Tanaka M. et al. International consensus guidelines 2012 for the management of IPMN and MCN of the pancreas. Pancreatology. 2012; 12:183-97.
9. Maker A V, Lee L S, Raut C P, Clancy T E, Swanson R S. Cytology from pancreatic cysts has marginal utility in surgical decision-making. Ann Surg Oncol. 2008; 15:3187-92.
10. Correa-Gallego C, Ferrone C R, Thayer S P, Wargo J A, Warshaw A L, Fernandez-Del Castillo C. Incidental pancreatic cysts: do we really know what we are watching? Pancreatology. 2010; 10:144-50.
11. Pelaez-Luna M. et al. Do consensus indications for resection in branch duct intraductal papillary mucinous neoplasm predict malignancy? A study of 147 patients. Am J Gastroenterol. 2007; 102:1759-64.
12. Wong J. et al. High-Grade Dysplasia and Adenocarcinoma Are Frequent in Side-Branch Intraductal Papillary Mucinous Neoplasm Measuring Less than 3 cm on Endoscopic Ultrasound. J Gastrointest Surg. 2012.
13. Hines O J, Reber H A. Pancreatic surgery. Curr Opin Gastroenterol. 2008; 24:603-11.
14. Goggins M. Identifying molecular markers for the early detection of pancreatic neoplasia. Semin Oncol. 2007; 34:303-10.
15. Medina P P, Slack F J. microRNAs and cancer: an overview. Cell Cycle. 2008; 7:2485-92.
16. Xi Y. et al. Systematic analysis of microRNA expression of RNA extracted from fresh frozen and formalin-fixed paraffin-embedded samples. Rna. 2007; 13:1668-74.
17. Cortez M A, Bueso-Ramos C, Ferdin J, Lopez-Berestein G, Sood A K, Calin G A. MicroRNAs in body fluids—the mix of hormones and biomarkers. Nat Rev Clin Oncol. 2011; 8:467-77.
18. Szafranska A E. et al. MicroRNA expression alterations are linked to tumorigenesis and non-neoplastic processes in pancreatic ductal adenocarcinoma. Oncogene. 2007; 26:4442-52.
19. Ryu J K, Hong S M, Karikari C A, Hruban R H, Goggins M G, Maitra A. Aberrant MicroRNA-155 expression is an early event in the multistep progression of pancreatic adenocarcinoma. Pancreatology. 10:66-73.
20. Habbe N. et al. MicroRNA miR-155 is a biomarker of early pancreatic neoplasia. Cancer Biol Ther. 2009; 8:340-6.
21. MiRbase: The MicroRNA sequence database. Available at: world wide website: microrna.sanger.ac.uk. Accessed February 7.
22. Adsay N V F N. et al, Intraductal Papillary Mucinous Neoplasm of the Pancreas. In: Bosman F T, Carneiro F, Hruban R H, Theise N D, editors. WHO classification of tumors of the digestive system. Lyon: WHO Press; 2010. p. 304-313.
23. Schmittgen T D, Livak K J. Analyzing real-time PCR data by the comparative C(T) method. Nat Protoc. 2008; 3:1101-8.
24. Storey J D, Tibshirani R. Statistical significance for genomewide studies. Proc Natl Acad Sci USA. 2003; 100:9440-5.
25. Xiao F, Zuo Z, Cai G, Kang S, Gao X, Li T. miRecords: an integrated resource for microRNA-target interactions. Nucleic Acids Res. 2009; 37:D105-10.
26. Vergoulis T. et al. TarBase 6.0: capturing the exponential growth of miRNA targets with experimental support. Nucleic Acids Res. 2012; 40:D222-9.
27. Fenstermacher D A, Wenham R M, Rollison D E, Dalton W S. Implementing personalized medicine in a cancer center. Cancer J. 2011; 17:528-36.
28. Matthaei H. et al. miRNA biomarkers in cyst fluid augment the diagnosis and management of pancreatic cysts. Clin Cancer Res. 2012; 18:4713-24.
29. Lubezky N. et al. MicroRNA expression signatures in intraductal papillary mucinous neoplasm of the pancreas. Surgery. 2013; 153:663-72.
30. Sun D. et al. miR-99 family of MicroRNAs suppresses the expression of prostate-specific antigen and prostate cancer cell proliferation. Cancer Res. 2011; 71:1313-24.
31. Jiao L R. et al. MicroRNAs targeting oncogenes are down-regulated in pancreatic malignant transformation from benign tumors. PLoS One. 2012; 7:e32068.
32. Frampton A E, Krell J, Jacob J, Stebbing J, Castellano L, Jiao L R. Loss of miR-126 is crucial to pancreatic cancer progression. Expert Rev Anticancer Ther. 2012; 12:881-4.
33. Li B H. et al. Reduced miR-100 expression in cervical cancer and precursors and its carcinogenic effect through targeting PLK1 protein. Eur J Cancer. 2011; 47:2166-74.
34. Liu J, Lu K H, Liu Z L, Sun M, De W, Wang Z X. MicroRNA-100 is a potential molecular marker of non-small cell lung cancer and functions as a tumor suppressor by targeting polo-like kinase 1. BMC Cancer. 2012; 12:519.
35. Wang H. et al. MicroRNA-342 inhibits colorectal cancer cell proliferation and invasion by directly targeting DNA methyltransferase 1. Carcinogenesis. 2011; 32:1033-42.
36. Weichert W. et al. Overexpression of Polo-like kinase 1 is a common and early event in pancreatic cancer. Pancreatology. 2005; 5:259-65.
37. Zhang J J. et al. Association of increased DNA methyltransferase expression with carcinogenesis and poor prognosis in pancreatic ductal adenocarcinoma. Clin Transl Oncol. 2012; 14:116-24.

38. Song B. et al. Plk1 phosphorylation of orc2 and hbo1 contributes to gemcitabine resistance in pancreatic cancer. Mol Cancer Ther. 2013; 12:58-68.
39. Bergmann U, Funatomi H, Kornmann M, Beger H G, Korc M. Increased expression of insulin receptor substrate-1 in human pancreatic cancer. Biochem Biophys Res Commun. 1996; 220:886-90.
40. Greenbaum D, Colangelo C, Williams K, Gerstein M. Comparing protein abundance and mRNA expression levels on a genomic scale. Genome Biol. 2003; 4:117.
41. Van der Auwera I, Limame R, van Dam P, Vermeulen P B, Dirix L Y, Van Laere S J. Integrated miRNA and mRNA expression profiling of the inflammatory breast cancer subtype. Br J Cancer. 2010; 103:532-41.
42. Vasudevan S, Tong Y, Steitz J A. Switching from repression to activation: microRNAs can up-regulate translation. Science. 2007; 318:1931-4.
43. Park Y G. et al. [MicroRNA expression pattern in intraductal papillary mucinous neoplasm]. Korean J Gastroenterol. 2011; 58:190-200.
44. Caponi S. et al. The good, the bad and the ugly: a tale of miR-101, miR-21 and miR-155 in pancreatic intraductal papillary mucinous neoplasms. Ann Oncol. 2013; 24:734-41.
45. Zhang D X, Dai Y D, Yuan S X, Tao L. Prognostic factors in patients with pancreatic cancer. Exp Ther Med. 2012; 3:423-32.
46. Mitchell P S. et al. Circulating microRNAs as stable blood-based markers for cancer detection. Proc Natl Acad Sci USA. 2008; 105:10513-8.
47. Henry J C, Bassi C, Giovinazzo F, Bloomston M. MicroRNA from Pancreatic Duct Aspirate Differentiates Cystic Lesions of the Pancreas. Ann Surg Oncol. 2013.
48. Li A. et al. MicroRNA Array Analysis Finds Elevated Serum miR-1290 Accurately Distinguishes Patients with Low-Stage Pancreatic Cancer from Healthy and Disease Controls. Clin Cancer Res. 2013.
49. Nissim S, Idos G E, Wu B. Genetic markers of malignant transformation in intraductal papillary mucinous neoplasm of the pancreas: a meta-analysis. Pancreas. 2012; 41:1195-205.
50. Wu J. et al. Recurrent GNAS mutations define an unexpected pathway for pancreatic cyst development. Sci Transl Med. 2011; 3:92ra66.
51. American Cancer Society. Cancer Facts and Figures 2014. Atlanta: American Cancer Society. 2014.
52. Berman J J, Albores-Saavedra J, Bostwick D, Delellis R, Eble J, Hamilton S R, et al. Precancer: a conceptual working definition—results of a Consensus Conference. Cancer detection and prevention. 2006; 30:387-94.
53. Canto M I, Harinck F, Hruban R H, Offerhaus G J, Poley J W, Kamel I, et al. International Cancer of the Pancreas Screening (CAPS) Consortium summit on the management of patients with increased risk for familial pancreatic cancer. Gut. 2013; 62:339-47.
54. Permuth-Wey J C Y, Fisher K, McCarthy S, Qu X, Lloyd M, Kasprzak A, Fournier M, Williams V L, Ghia K M, Yoder S, Hall L, Georgeades C, Olaoye F, Yeatman T, Centeno B, Klapman J, Coppola D, Malafa M. Genome-wide microRNA expression analysis identifies biologically-meaningful miRNAs that may aid in differentiating between high-risk and low-risk intraductal papillary mucinous neoplasms of the pancreas (in press, PLos One).
55. Wang J, Chen J, Chang P, LeBlanc A, Li D, Abbruzzesse J L, et al. MicroRNAs in plasma of pancreatic ductal adenocarcinoma patients as novel blood-based biomarkers of disease. Cancer Prev Res (Phila). 2009; 2:807-13.
56. Liu R, Chen X, Du Y, Yao W, Shen L, Wang C, et al. Serum microRNA expression profile as a biomarker in the diagnosis and prognosis of pancreatic cancer. Clin Chem. 2012; 58:610-8.
57. Schultz N A, Dehlendorff C, Jensen B V, Bjerregaard J K, Nielsen K R, Bojesen S E, et al. MicroRNA biomarkers in whole blood for detection of pancreatic cancer. JAMA. 2014; 311:392-404.
58. Ganepola G A, Rutledge J R, Suman P, Yiengpruksawan A, Chang D H. Novel blood-based microRNA biomarker panel for early diagnosis of pancreatic cancer. World journal of gastrointestinal oncology. 2014; 6:22-33.
59. Geiss G K, Bumgarner R E, Birditt B, Dahl T, Dowidar N, Dunaway D L, et al. Direct multiplexed measurement of gene expression with color-coded probe pairs. Nat Biotechnol. 2008; 26:317-25.
60. Blondal T, Jensby Nielsen S, Baker A, Andreasen D, Mouritzen P, Wrang Teilum M, et al. Assessing sample and miRNA profile quality in serum and plasma or other biofluids. Methods. 2013; 59:164-9.
61. Farina N H, Wood M E, Perrapato S D, Francklyn C S, Stein G S, Stein J L, et al. Standardizing analysis of circulating microRNA: clinical and biological relevance. Journal of cellular biochemistry. 2014; 115:805-11.
62. Abdalla M L B, Simkin M., et al. Effect of RNA Isolation Method on microRNA Quantity and Quality in Plasma: A Comparative Study. Norgen Biotek Corporation Application Note 49: RNA Sample Preparation (2011).
63. Blondal T, Jensby Nielsen S, Baker A, Andreasen D, Mouritzen P, Wrang Teilum M, et al. Assessing sample and miRNA profile quality in serum and plasma or other biofluids. Methods. 2013; 59:S1-6.
64. Pritchard C C, Kroh E, Wood B, Arroyo J D, Dougherty K J, Miyaji M M, et al. Blood cell origin of circulating microRNAs: a cautionary note for cancer biomarker studies. Cancer Prev Res (Phila). 2012; 5:492-7.
65. Kirschner M B, Edelman J J, Kao S C, Vallely M P, van Zandwijk N, Reid G. The Impact of Hemolysis on Cell-Free microRNA Biomarkers. Front Genet. 2013; 4:94.
66. Reis P P, Waldron L, Goswami R S, Xu W, Xuan Y, Perez-Ordonez B, et al. mRNA transcript quantification in archival samples using multiplexed, color-coded probes. BMC Biotechnol. 2011; 11:46.
67. Huang Z, Huang D, Ni S, Peng Z, Sheng W, Du X. Plasma microRNAs are promising novel biomarkers for early detection of colorectal cancer. Int J Cancer. 2010; 127:118-26.
68. Zhao H, Shen J, Medico L, Wang D, Ambrosone C B, Liu S. A pilot study of circulating miRNAs as potential biomarkers of early stage breast cancer. PLoS One. 2010; 5:e13735.
69. Smyth G K. Linear models and empirical bayes methods for assessing differential expression in microarray experiments. Stat Appl Genet Mol Biol. 2004; 3:Article3.
70. Chen D T, Hsu Y L, Fulp W J, Coppola D, Haura E B, Yeatman T J, et al. Prognostic and predictive value of a malignancy-risk gene signature in early-stage non-small cell lung cancer. Journal of the National Cancer Institute. 2011; 103:1859-70.
71. Chen D T, Nasir A, Culhane A, Venkataramu C, Fulp W, Rubio R, et al. Proliferative genes dominate malignancy-risk gene signature in histologically-normal breast tissue. Breast cancer research and treatment. 2010; 119:335-46.
72. Suryawanshi S, Vlad A M, Lin H M, Mantia-Smaldone G, Laskey R, Lee M, et al.

Plasma microRNAs as novel biomarkers for endometriosis and endometriosis-associated ovarian cancer. Clin Cancer Res. 2013; 19:1213-24.
73. Fourie N H, Peace R M, Abey S K, Sherwin L B, Rahim-Williams B, Smyser P A, et al. Elevated circulating miR-150 and miR-342-3p in patients with irritable bowel syndrome. Experimental and molecular pathology. 2014.
74. Hu J, Wang Z, Liao B Y, Yu L, Gao X, Lu S, et al. Human miR-1228 as a stable endogenous control for the quantification of circulating microRNAs in cancer patients. Int J Cancer. 2014.
75. Tang S, Bonaroti J, Unlu S, Liang X, Tang D, Zeh H J, et al. Sweating the small stuff: microRNAs and genetic changes define pancreatic cancer. Pancreas. 2013; 42:740-59.
76. Kapoor S. miR-145 and its influence on tumor growth in systemic malignancies. Eur J Cancer Prev. 2014; 23:233.
77. Gao L, Yang Y, Xu H, Liu R, Li D, Hong H, et al. miR-335 functions as a tumor suppressor in pancreatic cancer by targeting OCT4. Tumour biology: the journal of the International Society for Oncodevelopmental Biology and Medicine. 2014; 35:8309-18.
78. Hirata H, Hinoda Y, Shahryari V, Deng G, Tanaka Y, Tabatabai Z L, et al. Genistein downregulates onco-miR-1260b and upregulates sFRP1 and Smad4 via demethylation and histone modification in prostate cancer cells. Br J Cancer. 2014; 110:1645-54.
79. Zhou F, Wang W, Xing Y, Wang T, Xu X, Wang J. NF-kappaB target microRNAs and their target genes in TNFalpha-stimulated HeLa cells. Biochimica et biophysica acta. 2014; 1839:344-54.
80. Li A, Omura N, Hong S M, Vincent A, Walter K, Griffith M, et al. Pancreatic cancers epigenetically silence SIP1 and hypomethylate and overexpress miR-200a/200b in association with elevated circulating miR-200a and miR-200b levels. Cancer Res. 2010; 70:5226-37.
81. Chiyomaru T, Yamamura S, Fukuhara S, Hidaka H, Majid S, Saini S, et al. Genistein up-regulates tumor suppressor microRNA-574-3p in prostate cancer. PLoS One. 2013; 8:e58929.
82. Su Y, Ni Z, Wang G, Cui J, Wei C, Wang J, et al. Aberrant expression of microRNAs in gastric cancer and biological significance of miR-574-3p. International immunopharmacology. 2012; 13:468-75.
83. Tsujiura M, Ichikawa D, Komatsu S, Shiozaki A, Takeshita H, Kosuga T, et al. Circulating microRNAs in plasma of patients with gastric cancers. Br J Cancer. 102:1174-9.
84. Chin L J, Slack F J. A truth serum for cancer—microRNAs have major potential as cancer biomarkers. Cell research. 2008; 18:983-4.
85. Berger F, Reiser M F. Micro-RNAs as potential new molecular biomarkers in oncology: have they reached relevance for the clinical imaging sciences? Theranostics. 2013; 3:943-52.
86. Neelakandan K, Babu P, Nair S. Emerging roles for modulation of microRNA signatures in cancer chemoprevention. Curr Cancer Drug Targets. 2012; 12:716-40.

We claim:

1. A method of treating and/or delaying onset of the development of pancreatic cancer in a subject, the method comprising:
   (a) detecting the level of expression of let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, miR-98, miR-200a-3p, miR-1185-5p, miR-33a-5p, miR-574-3p, miR-663b, miR-99b, miR-342-3p, miR-126, miR-888, miR-130a, let-7c, miR-296, and miR-302a in a blood sample from the subject;
   (b) comparing the detected expression level to a reference expression level, wherein a differential expression of let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, miR-98, miR-200a-3p, miR-1185-5p, miR-33a-5p, miR-574-3p, miR-663b, miR-99b, miR-342-3p, miR-126, miR-888, miR-130a, let-7c, miR-296, and miR-302a in the blood sample, as compared to the reference expression level, is indicative of the presence of pancreatic cancer, or a higher risk of developing pancreatic cancer, versus the absence of pancreatic cancer, or a lower risk of developing pancreatic cancer, respectively; and
   (c) administering a therapy to treat and/or delay onset of the pancreatic cancer to the subject identified as having the pancreatic cancer, or at a higher risk of developing pancreatic cancer; wherein the therapy comprises surgical resection, pancreatoduodenectomy (Whipple procedure), chemotherapy, radiation, immunotherapy, or a combination of two or more of the foregoing.

2. The method of claim 1, wherein a differential expression of let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, miR-98, miR-200a-3p, miR-1185-5p, miR-33a-5p, miR-574-3p, miR-663b, miR-99b, miR-342-3p, miR-126, miR-888, miR-130a, let-7c, miR-296, and miR-302a in the blood sample, as compared to the reference expression level, is indicative of a pancreatic cancer precursor (such as intraductal papillary mucinous neoplasm (IPMN)) versus non-IPMN (normal cells).

3. A method of treating and/or delaying onset of pancreatic cancer in a subject, comprising measuring the level of expression of let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, miR-98, miR-200a-3p, miR-1185-5p, miR-33a-5p, miR-574-3p, miR-663b, miR-99b, miR-342-3p, miR-126, miR-888, miR-130a, let-7c, miR-296, and miR-302a in a blood sample obtained from the subject; and administering a treatment for the pancreatic cancer; wherein the treatment comprises surgical resection, pancreatoduodenectomy (Whipple procedure), chemotherapy, radiation, immunotherapy, or a combination of two or more of the foregoing.

4. A composition of matter comprising:
(a) a microarray chip corresponding to a profile of miRNAs that are differentially expressed in a blood sample of an individual having pancreatic cancer, or having a high risk of developing pancreatic cancer, as compared to the corresponding blood sample of an individual having no risk or low risk of developing pancreatic cancer, the microarray chip consisting essentially of oligonucleotides corresponding to let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, miR-98, miR-200a-3p, miR-1185-5p, miR-33a-5p, miR-574-3p, miR-663b, miR-99b, miR-342-3p, miR-126, miR-888, miR-130a, let-7c, miR-296, and miR-302a; or (b) a microarray chip corresponding to a profile of miRNAs that are differentially expressed in a blood sample of an individual having a pancreatic lesion and having high risk of developing pancreatic cancer compared to the corresponding blood sample of an individual having the pancreatic lesion and having no risk or low risk of developing pancreatic cancer, the microarray chip consisting essentially of oligonucleotides corresponding to let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, miR-98, miR-200a-3p, miR-1185-5p, miR-33a-5p, miR-574-3p, miR-663b, miR-99b, miR-342-3p, miR-126, miR-888, miR-130a, let-7c, miR-296, and miR-302a; or (c) a microarray chip corresponding to a profile of miRNAs that are differentially expressed in a blood sample of an individual having a pancreatic cancer precursor (such as intraductal papillary mucinous neoplasm (IPMN)) as compared to a non-IPMN (normal cells), the microarray chip consisting essentially of oligonucleotides corresponding to let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, miR-98, miR-200a-3p, miR-1185-5p, miR-33a-5p, miR-574-3p, miR-663b, miR-99b, miR-342-3p, miR-126, miR-888, miR-130a, let-7c, miR-296, and miR-302a; or (d) a microarray chip corresponding to a profile of miRNAs that are differentially expressed in a blood sample of an individual having a malignant intraductal papillary mucinous neoplasm (IPMN) as compared to a benign IPMN, the microarray chip consisting essentially of oligonucleotides corresponding to let-7a-5p, let-7d-5p, let-7f-5p, let-7g-5p, let-7i-5p, miR-107, miR-1260b, miR-126-3p, miR-142-3p, miR-145-5p, miR-146a-5p, miR-148a-3p, miR-15b-5p, miR-181a-5p, miR-191-5p, miR-199b-3p, miR-20a-5p, miR-20b-5p, miR-22-3p, miR-23a-3p, miR-24-3p, miR-26a-5p, miR-27a-3p, miR-29c-3p, miR-335-5p, miR-337-5p, miR-340-5p, miR-423-5p, miR-4454, miR-593-3p, miR-98, miR-200a-3p, miR-1185-5p, miR-33a-5p, miR-574-3p, miR-663b, miR-99b, miR-342-3p, miR-126, miR-888, miR-130a, let-7c, miR-296, and miR-302a.

* * * * *